(12) United States Patent
Coleman et al.

(10) Patent No.: US 9,886,493 B2
(45) Date of Patent: Feb. 6, 2018

(54) SYSTEMS AND METHODS FOR SENSORY AND COGNITIVE PROFILING

(71) Applicants: The Regents of the University of California, Oakland, CA (US); The Salk Institute for Biological Studies, La Jolla, CA (US)

(72) Inventors: Todd Prentice Coleman, La Jolla, CA (US); Rui Ma, San Diego, CA (US); Sanggyun Kim, San Diego, CA (US); Cheolsoo Park, San Diego, CA (US); Ricardo Gil Da Costa, San Diego, CA (US); Raynard Fung, La Jolla, CA (US); Diego Mesa, La Jolla, CA (US)

(73) Assignees: The Regents of the University of California, Oakland, CA (US); The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 14/431,734

(22) PCT Filed: Sep. 27, 2013

(86) PCT No.: PCT/US2013/062491
§ 371 (c)(1),
(2) Date: Mar. 26, 2015

(87) PCT Pub. No.: WO2014/052938
PCT Pub. Date: Apr. 3, 2014

(65) Prior Publication Data
US 2015/0248470 A1   Sep. 3, 2015

Related U.S. Application Data

(60) Provisional application No. 61/707,613, filed on Sep. 28, 2012.

(51) Int. Cl.
A61B 5/0482 (2006.01)
G06F 17/30 (2006.01)
(Continued)

(52) U.S. Cl.
CPC ...... *G06F 17/30598* (2013.01); *A61B 5/0482* (2013.01); *A61B 5/0484* (2013.01);
(Continued)

(58) Field of Classification Search
None
See application file for complete search history.

(56) References Cited

U.S. PATENT DOCUMENTS 4,092,981 A   6/1978 Ertl
4,987,903 A   1/1991 Keppel et al.
(Continued)

FOREIGN PATENT DOCUMENTS

CN   101296554 A   10/2008
CN   101500471 A   8/2009
(Continued)

OTHER PUBLICATIONS

International Search Report and Written Opinion of PCT/US2013/062491 mailed by the Korean Intellectual Property Office dated Jan. 17, 2014 (20 pages).
(Continued)

*Primary Examiner* — Jacqueline Cheng
*Assistant Examiner* — Jairo Portillo
(74) *Attorney, Agent, or Firm* — Perkins Coie LLP

(57) ABSTRACT

Methods, devices, and systems are disclosed for producing cognitive and/or sensory profiles. In one aspect, a method to provide a cognitive or sensory assessment of a subject includes selecting a profile category from among a cognitive performance profile, a sensory performance profile, and a cognitive and sensory performance profile, presenting a
(Continued)

sequence of stimuli to a subject, the sequence of stimuli based on the selected profile category, acquiring physiological signals of the subject before, during, and after the presenting the sequence of stimuli to produce physiological data, and processing the physiological data to generate an information set including one or more quantitative values associated with the selected profile category.

17 Claims, 23 Drawing Sheets

(51) Int. Cl.
- *A61B 5/0484* (2006.01)
- *G06F 19/00* (2011.01)
- *A61B 5/0488* (2006.01)
- *A61B 5/16* (2006.01)
- *A61B 5/00* (2006.01)

(52) U.S. Cl.
CPC ........ *G06F 17/3053* (2013.01); *G06F 19/363* (2013.01); *A61B 5/0488* (2013.01); *A61B 5/04842* (2013.01); *A61B 5/04845* (2013.01); *A61B 5/04847* (2013.01); *A61B 5/165* (2013.01); *A61B 5/167* (2013.01); *A61B 5/168* (2013.01); *A61B 5/4011* (2013.01); *A61B 5/4017* (2013.01); *A61B 5/6814* (2013.01)

(56) References Cited

U.S. PATENT DOCUMENTS

| | | | |
|---|---|---|---|
| RE34,015 E | 8/1992 | Duffy | |
| 5,406,956 A | 4/1995 | Farwell | |
| 6,032,065 A * | 2/2000 | Brown | A61B 5/04085 600/383 |
| 6,061,593 A | 5/2000 | Fischell et al. | |
| 6,463,328 B1 | 10/2002 | John | |
| 6,832,110 B2 | 12/2004 | Sohmer et al. | |
| 6,947,790 B2 | 9/2005 | Gevins et al. | |
| 7,130,673 B2 | 10/2006 | Tolvanen-Laakso et al. | |
| 7,338,455 B2 | 3/2008 | White et al. | |
| D597,676 S | 8/2009 | Copeland et al. | |
| 7,986,691 B2 | 7/2011 | Park et al. | |
| 7,986,991 B2 | 7/2011 | Prichep | |
| 8,221,330 B2 | 7/2012 | Sarkela et al. | |
| 2003/0013981 A1* | 1/2003 | Gevins | A61B 5/0484 600/544 |
| 2003/0032870 A1 | 2/2003 | Farwell | |
| 2003/0073921 A1* | 4/2003 | Sohmer | A61B 5/04842 600/544 |
| 2004/0002635 A1 | 1/2004 | Hargrove et al. | |
| 2005/0021104 A1 | 1/2005 | Dilorenzo | |
| 2005/0143629 A1 | 6/2005 | Farwell | |
| 2005/0273017 A1 | 12/2005 | Gordon | |
| 2006/0183981 A1* | 8/2006 | Skinner | A61B 5/0484 600/301 |
| 2006/0293608 A1 | 12/2006 | Rothman et al. | |
| 2007/0100214 A1 | 5/2007 | Steinert | |
| 2007/0106169 A1 | 5/2007 | Fadem | |
| 2007/0191727 A1 | 8/2007 | Fadem | |
| 2008/0221422 A1 | 9/2008 | Rantala | |
| 2008/0249430 A1 | 10/2008 | John et al. | |
| 2009/0214060 A1 | 8/2009 | Chuang et al. | |
| 2009/0216091 A1 | 8/2009 | Arndt | |
| 2009/0220425 A1 | 9/2009 | Moxon et al. | |
| 2009/0227889 A2 | 9/2009 | John et al. | |
| 2010/0009325 A1* | 1/2010 | Afanasiev | G09B 19/00 434/236 |
| 2010/0010336 A1 | 1/2010 | Pettegrew et al. | |
| 2010/0041962 A1 | 2/2010 | Causevic et al. | |
| 2010/0099954 A1 | 4/2010 | Dickinson et al. | |
| 2010/0274152 A1 | 10/2010 | McPeck et al. | |
| 2011/0109879 A1 | 5/2011 | Palti-Wasserman et al. | |
| 2012/0041330 A1 | 2/2012 | Prichep et al. | |
| 2012/0071781 A1 | 3/2012 | Fadem | |
| 2012/0077160 A1* | 3/2012 | DeGutis | G09B 7/02 434/236 |
| 2012/0094315 A1 | 4/2012 | Fryar-Williams | |
| 2012/0150545 A1 | 6/2012 | Simon | |
| 2012/0191000 A1 | 7/2012 | Adachi et al. | |
| 2012/0221075 A1 | 8/2012 | Bentwich | |
| 2012/0253163 A1 | 10/2012 | Afanasewicz et al. | |
| 2013/0127708 A1 | 5/2013 | Jung et al. | |
| 2013/0172721 A1 | 7/2013 | McPeck et al. | |
| 2015/0305686 A1 | 10/2015 | Coleman et al. | |
| 2015/0313498 A1 | 11/2015 | Coleman et al. | |

FOREIGN PATENT DOCUMENTS

| | | |
|---|---|---|
| EP | 1468646 A2 | 10/2004 |
| JP | 2008503261 A | 2/2008 |
| JP | 2009521246 A | 6/2009 |
| JP | 2009542276 A | 12/2009 |
| JP | 2010-526379 A | 7/2010 |
| JP | 2011-186667 A | 9/2011 |
| KR | 1020060085543 | 7/2006 |
| KR | 1020120111030 | 10/2012 |
| WO | WO-2009044271 A2 | 4/2009 |
| WO | 2011109716 | 9/2011 |
| WO | WO-2011160222 A1 | 12/2011 |

OTHER PUBLICATIONS

Byun, S. C., Authorized Officer, Korean Intellectual Property Office, International Search Report and Written Opinion, International Application No. PCT/US2013/062491, dated Jan. 17, 2014, 22 pages.

Kim, D.-H. et al., "Epidermal Electronics", Science, vol. 333, 2011, pp. 838-843.

Kim, S. et al., "Efficient Bayesian Inference Methods via Convex Optimization and Optimal Transport", Information Theory Proceedings (ISIT), 2013 IEEE International Symposium, pp. 2259-2263.

Liao, L.-D. et al., "Biosensor technologies for augmentedbrain-computer interfaces in the next decades," Proc. IEEE, vol. 100, 2012, pp. 1553-1566.

Ma, R. et al., "Generalizing the Posterior Matching Scheme to Higher Dimensions via Optimal Transportation", Allerton Conference on Communication, Control, and Computing, Sep. 2011, 7 pages.

Makeig, S. et al., "Evolving signal processing for brain-computer interfaces," Proc. IEEE, vol. 100, 2012, pp. 1567-1584.

Oh, E. G., Authorized Officer, Korean Intellectual Property Office, International Search Report and Written Opinion, International Patent Application No. PCT/US2013/069520, dated Feb. 24, 2014, 15 pages.

Omar, C. et al., "A Feedback Information-Theoretic Approach to the Design of Brain-Computer Interfaces", International Journal on Human-Computer Interaction, 27(1), Jan. 2011, pp. 5-23.

Rissanen, J., "Hypothesis selection and testing by the MDL principle," The Computer Journal, vol. 42, No. 4, 1999, pp. 260-269.

Sellers, E. W. et al., "A P300-based brain-computer interface: Initial tests by ALS patients", Clinical Neurophysiology 117 (2006) 538-548.

Shayevitz, O. et al., "Optimal Feedback Communication via Posterior Matching", IEEE Transactions on Information Theory, vol. 57, No. 3, Mar. 2011, pp. 1186-1222.

Shin, J. C., Authorized Officer, Korean Intellectual Property Office, International Search Report and Written Opinion, International Patent Application No. PCT/US2013/064892, dated Apr. 11, 2014, 14 pages.

Ward, D. et al., "Fast Hands-free Writing by Gaze Direction", Nature, vol. 418, Aug. 22, 2002, p. 838.

Ward, D.J. et al., "Dasher—a Data Entry Interface Using Continuous Gestures and Language Models.", In proceedings UIST 2000, 10 pages.

(56) References Cited

OTHER PUBLICATIONS

Zander, T.O. et al., "Towards passive brain-computer interfaces: applying brain-computer interface technology to human-machine systems in general", J. Neural Eng. 8, 2011, pp. 1-5

Coleman et al., "Epidermal electronics capture of event-related brain potentials (ERP) signal in a 'real-world' target detection task", poster presentation at Society for Neuroscience Annual Meeting, Oct. 14, 2012, 1 page.

Garrido et al. "The mismatch negativity: A review of underlying mechanisms," Clinical Neurophysiology, Mar. 2009, 120, pp. 453-463.

Gil Da Costa, et al. "Support for a non-human primate model of schizophrenia: acute subanesthetic ketamine reduces mismatch negativity (MMN) and P3", Nov. 13, 2011, 2 pages—Presentation Abstract accessed Mar. 1, 2017 from http://www.abstractsonline.com/Plan/ViewAbstract.aspx?sKey=564343a3-b57a-4e7f-ab80-3ff7e55f35c2&cKey=bdc176e5-a1 c2-40c8-bb95-38edac34b11e &mKey=%7b8334BE29-8911-4991-8C31-32B32DD5E6C8%7d.

Heekeren et al. "Mismatch negativity generation in the human 5HT2A agonist and NMDA antagonist model of psychosis." Psychopharmacology (Berl). Jul. 2008; 199(1): pp. 77-88.

Huang et al. "Stimulus dependency and mechanisms of surround modulation in cortical area MT," Journal of Neuroscience Dec. 17, 2008, 28 (51) pp. 13889-13906.

Javitt, et al. "Demonstration of mismatch negativity in the monkey," Aug. 1992 Electroencephalography and Clinical Neurophysiology. 83, pp. 87-90.

Johnstone, et al. "Predicting schizophrenia: findings from the Edinburgh High-Risk Study," The British Journal of Psychiatry, Jan. 2005, 186 (1), pp. 18-25.

Lieberman, J. A. et al., "Effectiveness of antipsychotic drugs in patients with chronic schizophrenia," The New England Journal of Medicine, Sep. 2005, 353, pp. 1209-1223.

Näätänen, R. et al. "'Primitive intelligence' in the auditory cortex," TRENDS in Neurosciences, Jun. 2001, 24, pp. 283-288.

Näätänen, R. et al., "The mismatch negativity (MMN)—A unique window to disturbed central auditory processing in ageing and different clinical conditions," Clinical Neurophysiology 2012, vol. 123, pp. 424-458.

Sutton et al., "Evoked-potentials correlates of stimulus uncertainty," Science, Nov. 26, 1965, vol. 150, No. 3700, pp. 1187-1188.

Toomey, et al., "Why do children with ADHD discontinue their medication?" Clinical Pediatrics, 2012, 51(8), pp. 763-769.

Umbricht, D. et al., "Ketamine-induced deficits in auditory and visual context-dependent processing in healthy volunteers: implications for models of cognitive deficits in schizophrenia," Arch Gen Psychiatry, Dec. 2000; 57(12): pp. 1139-1147.

Van Der Stelt, et al. "Application of electroencephalography to the study of cognitive and brain functions in schizophrenia," Schizophrenia Bulletin, Jul. 2007; 33(4): pp. 955-970.

Vecchio, et al. "The Use of Auditory Event-Related Potentials in Alzheimer's Disease Diagnosis," International Journal of Alzheimer's Disease vol. 2011 (2011), Article ID 653173, 8 pages.

Wynn, et al., "Mismatch negativity, social cognition, and functioning in schizophrenia patients," Biological Psychiatry 2010; 67, pp. 940-947.

International Search Report and Written Opinion issued in PCT/US2013/062491 by the Korean Intellectual Property Office dated Jan. 17, 2014, 22 pages.

International Search Report and Written Opinion issued in PCT/US2013/069520 by the Korean Intellectual Property Office dated Feb. 24, 2014, 15 pages.

International Search Report and Written Opinion issued in PCT/US2013/064892 by the Korean Intellectual Property Office dated Apr. 11, 2014, 9 pages.

Extended European Search Report for European Application No. 13845002.8; dated Apr. 28, 2016, 9 pages.

Extended European Search Report for European Application No. 13842699.4; dated May 24, 2016, 7 pages.

Extended European Search Report for European Application No. 13852926.8; dated Sep. 28, 2016, 11 pages.

Chinese Office Action for Chinese Application No. 201380058415.8; dated Dec. 8, 2016, 14 pages.

"Statistics: Any Disorder Among Adults". National Institute of Mental Health. National Institutes of Health. http://www.nimh.nih.gov/statistics/1ANYDIS_ADULT_shtml.

"What is Schizophrenia?". National Institute of Mental Health. Sep. 8, 2009. National Institutes of Health. http://www.nimh.nih.gov/health/publications/schizophrenia/what-is-schizophrenia.shtml.

Breggin, P.R., A misdiagnosis, anywhere. The New York Times. http://www.nytimes.com/roomfordebate/2011/10/12/are-americans-more-prone-to-adhd/adhd-is-a-misdiagnosis.

Pilgreen, KL, "Physiologic, medical, and cognitive correlates of electroencephalography." In P. L. Nunez (Ed.), Neocortical dynamics and EEG rhythms, pp. 195-248. New York: Oxford University Press, 1995.

Partial Supplementary European Search Report for European Application No. 13852926.8; dated Jun. 6, 2016.

Chinese Office Action for Chinese Application No. 201380058185.5; dated Mar. 3, 2017.

Chinese Office Action for Chinese Application No. 201380060011.2; dated Oct. 8, 2016.

Chinese Office Action for Chinese Application No. 201380060011.2; dated May 19, 2017.

Japanese Office Action for Japanese Application No. 2015-534783, dated Aug. 3, 2017.

Japanese Office Action for Japanese Application No. 2015-541992, dated Sep. 1, 2017.

\* cited by examiner

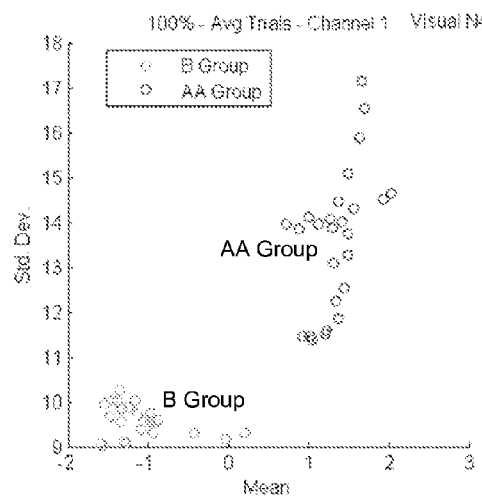 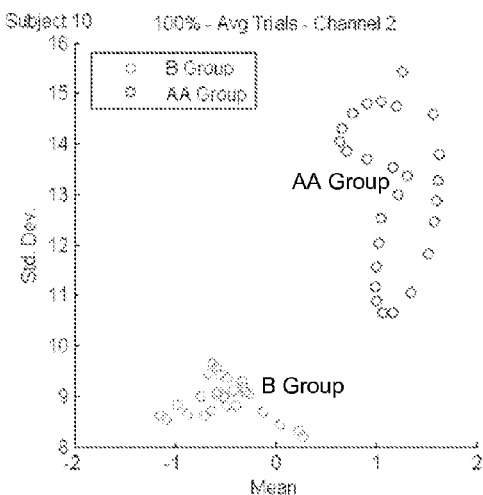
FIG. 5A                    FIG. 5B
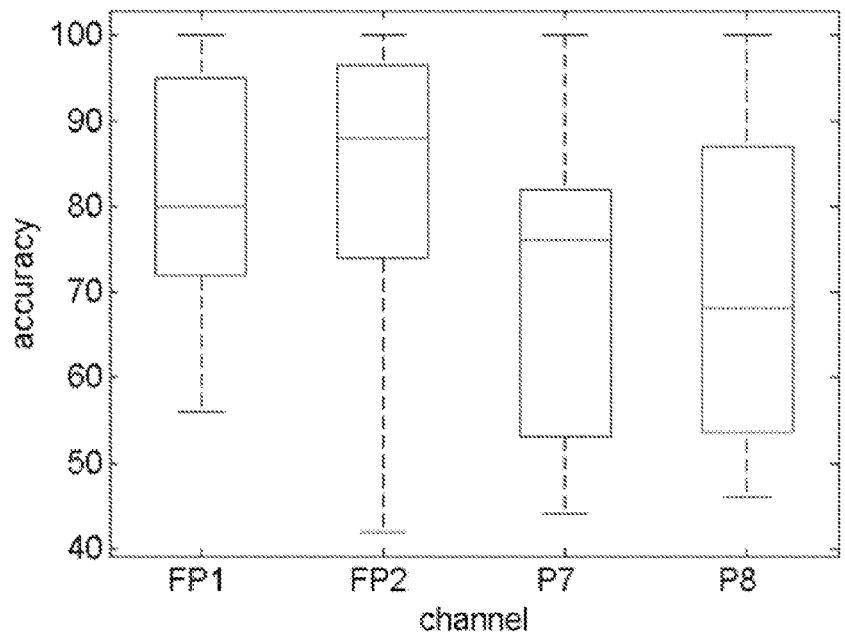
FIG. 6

Exemplary Guided Classification Algorithm
*(Nonparametric Statistical Test)*

| Electrode | FP1 | FP2 | P7 | P8 |
|---|---|---|---|---|
| accuracy | 80 | 77 | 70 | 68 |

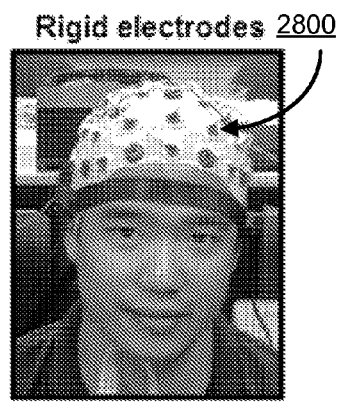
FIG. 28A
Example Existing ERP Analysis Software
2801
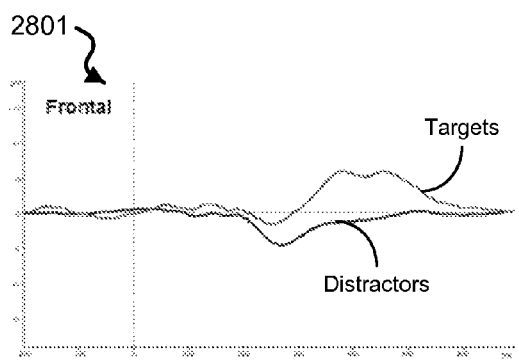
2802
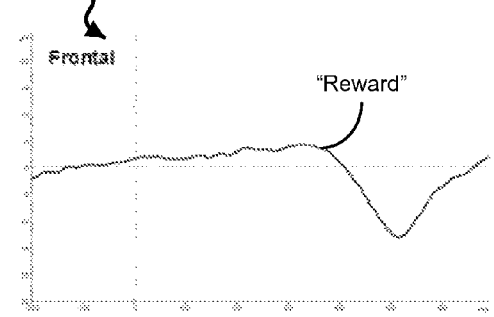
Exemplary Pre-Processing ERP Analysis Code of the Disclosed Technology
2811
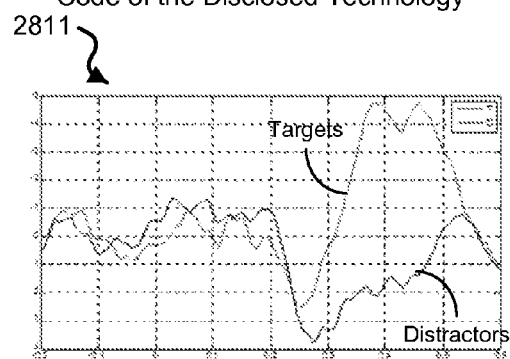
2812
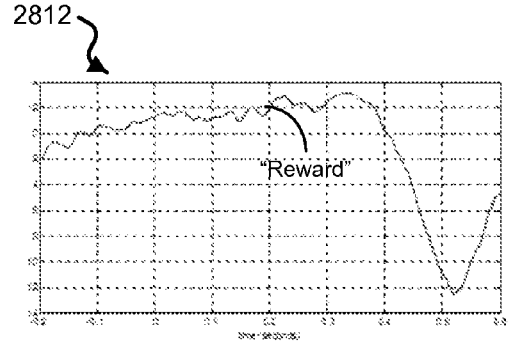
FIG. 28B

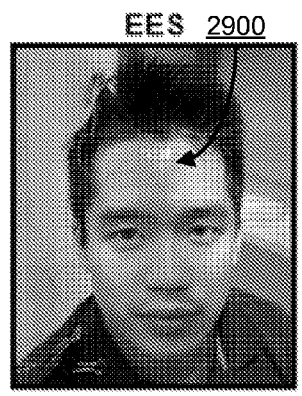
FIG. 29A
Example Existing ERP Analysis Software
2901
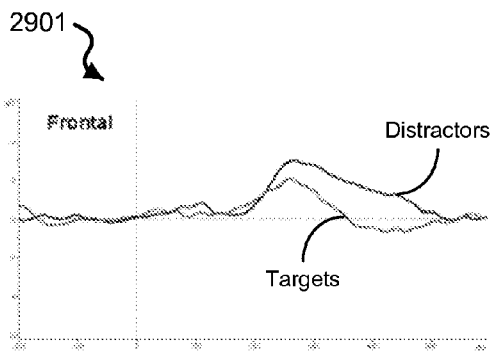
Exemplary Pre-Processing ERP Analysis Code of the Disclosed Technology
2911
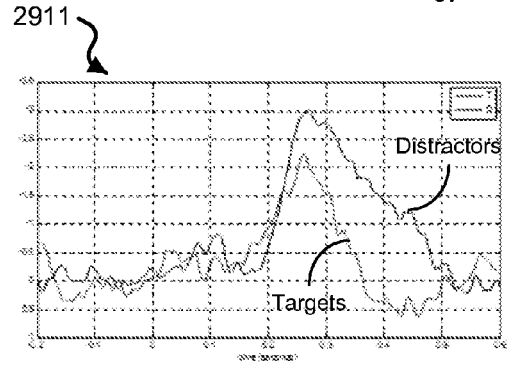
2902
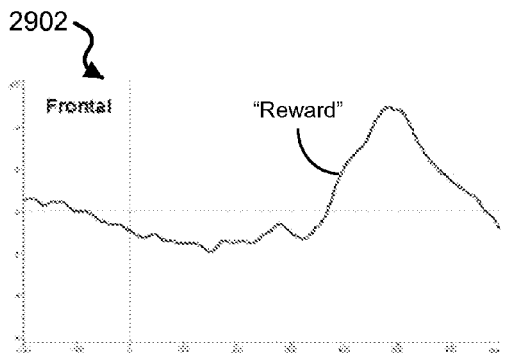
2912
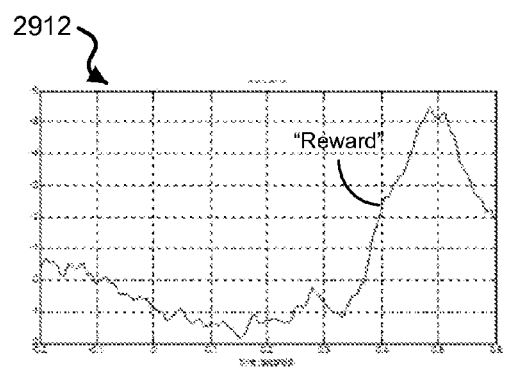
FIG. 29B

SYSTEMS AND METHODS FOR SENSORY AND COGNITIVE PROFILING

CROSS REFERENCE TO RELATED APPLICATIONS

This patent document claims the benefit of priority of U.S. Provisional Patent Application No. 61/707,613, entitled "METHOD AND APPARATUS FOR ACQUISITION, ANALYSIS AND EVALUATION OF BRAIN SIGNALS AND CORRELATED INDIVIDUAL KNOWLEDGE AND/OR STATE OF AWARENESS PROFILE" filed on Sep. 28, 2012. The entire content of the aforementioned patent application is incorporated by reference as part of the disclosure of this application.

TECHNICAL FIELD

This patent document relates to systems, devices, and processes for analyzing brain function.

BACKGROUND

Electroencephalography (EEG) is the recording of electrical activity exhibited by the brain using electrodes positioned on a subject's scalp, forming a spectral content of neural signal oscillations that comprise an EEG data set. For example, the electrical activity of the brain that is detected by EEG techniques can include voltage fluctuations, e.g., resulting from ionic current flows within the neurons of the brain. In some contexts, EEG refers to the recording of the brain's spontaneous electrical activity over a short period of time, e.g., less than an hour. EEG can be used in clinical diagnostic applications including epilepsy, coma, encephalopathies, brain death, and other diseases and defects, as well as in studies of sleep and sleep disorders. In some instances, EEG has been used for the diagnosis of tumors, stroke and other focal brain disorders.

One example of an EEG technique includes recording of event-related potentials (ERPs), which refer to EEG recorded brain responses that are correlated with a given event (e.g., simple stimulation and complex processes). For example, an ERP includes an electrical brain response—a brain wave—related to the sensory, motor, and/or cognitive processing. ERPs are associated with brain measures of perception (e.g., visual, auditory, etc.) and cognition (e.g., attention, language, decision making, etc.). A typical ERP waveform includes a temporal evolution of positive and negative voltage deflections, termed components. For example, typical components are classified using a letter (N/P: negative/positive) and a number (indicating the latency, in milliseconds from the stimulus event), for which this component arises.

SUMMARY

Disclosed are methods, systems, and devices for using specialized stimuli presentation structures (e.g., including images and sounds) for eliciting physiological data (e.g., brain signals) and/or behavioral data to infer and generate a unique set of information pertaining to individual and/or group mental abilities (e.g., cognitive and/or sensory performance), psychological states (e.g., awareness levels), and behavioral preferences.

In one aspect, a method to provide a cognitive or sensory assessment of a subject includes selecting a profile category from among a cognitive performance profile, a sensory performance profile, and a cognitive and sensory performance profile, presenting a sequence of stimuli to a subject, the sequence of stimuli based on the selected profile category, acquiring physiological signals of the subject before, during, and after the presenting the sequence of stimuli to produce physiological data, and processing the physiological data to generate an information set including one or more quantitative values associated with the selected profile category.

Implementations of the method can optionally include one or more of the following exemplary features. In some examples, the acquiring can be implemented without a behavioral response performed by the subject. For example, the sequence of stimuli can include at least one of a visual, auditory, olfactory, tactile, or gustatory stimulating medium based on the selected profile category. For example, the one or more quantitative values can include a quantitative score depicting a level of one or both of cognitive and sensory performance based on at least one of the subject's attention, memory, learning ability, confabulation characteristics, pattern integration ability, semantic integration ability, target detection ability, emotional valence, or preference, in which the quantitative score depicts the level at a particular time. For example, the one or more quantitative values can include a quantitative score depicting a level or state of awareness of the subject at a particular time. In some implementations of the method, the processing can include identifying a time interval associated with the physiological signals based on the presented stimuli and the selected profile category, grouping the physiological data corresponding to the time interval into one or more grouped data sets, and providing a statistical measure of a relationship across or within the grouped data sets to generate the one or more quantitative values for the selected profile category. For example, in some implementations, the method can further include processing the physiological data to increase a signal-to-noise ratio of the grouped data sets. For example, the grouping can be determined based on at least one of a pre-assigned category of the individual stimulus or an associative relationship of consecutive stimuli. In some implementations of the method, the processing can include identifying a time interval associated with the physiological signals based on the presented stimuli and the selected profile category, grouping the physiological data corresponding to the time interval into one or more grouped data sets, and providing a statistical measure of a relationship across or within the grouped data sets using previous physiological data acquired from the subject or other subjects to generate the one or more quantitative values for the selected profile category. In some implementations of the method, the processing can include identifying a time interval associated with the physiological signals based on the presented stimuli and the selected profile category, grouping the physiological data corresponding to the time interval into one or more initial grouped data sets, classifying each stimulus of the sequence of stimuli presented to the subject using a statistical test involving the initial grouped data sets, based on the classified stimuli, re-grouping the physiological data corresponding to the time interval into one or more grouped data sets, and providing a statistical measure of a relationship across or within the grouped data sets to generate the one or more quantitative values for the selected profile category. For example, in some implementations, the method can further include forming a modified sequence of stimuli using the generated information set for the subject, and presenting the modified sequence of stimuli to the subject. For example, in some implementations, the method can further include acquiring physiological signals of the subject before, during, and after the presenting the modified sequence of stimuli to produce new physiological data, and processing the new physiological data to generate an augmented information set including one or more augmented quantitative values associated with the selected profile category. For example, in some implementations, the method can further include creating an initial sequence of stimuli for each of the profile categories. In some examples, the acquiring the physiological signals can include recording electroencephalogram (EEG) signals generated by the subject. For example, the recording the EEG signals can include using one or more flexible EEG electrode sensor devices worn on the subject's scalp to measure and transmit the recorded EEG signals to a remote processing unit. In some examples, the acquiring the physiological signals can include recording electromyogram (EMG) signals generated by the subject. For example, in some implementations, the method can further include, prior to the processing, filtering the physiological signals to increase a signal-to-noise ratio of the physiological signals. For example, in some implementations, the method can further include, prior to the processing, pre-processing the physiological data including one or more of segmenting the physiological data or identifying characteristics from the physiological data. For example, in some implementations, the method can further include, based on the generated information set for the subject, generating an interaction between a machine and the subject. For example, in some implementations, the method can further include acquiring baseline physiological signals of the subject before the presenting the sequence of stimuli to produce baseline physiological data. In some examples, the sequence of stimuli presented to the subject can include environmental stimuli to passively stimulate a brain response of a subject. For example, in some implementations, the method can further include acquiring behavioral signals of the subject before, during, and after the presenting the sequence of stimuli to produce physiological data, and processing the behavioral data with the physiological data to generate the information set including one or more quantitative values associated with the selected profile category.

In another aspect, a computer program product comprising a computer-readable storage medium having code stored thereon, the code, when executed, causing a processor of a computer or computer system in a communication network to implement a method for providing a cognitive or sensory assessment of a subject, in which the computer program product is operated by the computer or computer system to implement the method. The computer implemented method includes providing a prompt to a subject to select a profile category including a cognitive performance profile, a sensory performance profile, and a cognitive and sensory performance profile, controlling a sequence of stimuli presented to a subject via a device, the sequence of stimuli based on the selected profile category, receiving physiological data representing physiological signals acquired from the subject before, during, and after the presenting the sequence of stimuli, and processing the physiological data to generate an information set including one or more quantitative values associated with the selected profile category.

Implementations of the computer program product can optionally include one or more of the following exemplary features. For example, in the computer program product, the processing step of the method can include identifying a time interval associated with the physiological signals based on the presented stimuli and the selected profile category, grouping the physiological data corresponding to the time interval into one or more grouped data sets, and providing a statistical measure of a relationship across or within the grouped data sets to generate the one or more quantitative values for the selected profile category. In some implementations, the computer implemented method of the computer program product can further include processing the physiological data to increase a signal-to-noise ratio of the grouped data sets. For example, the grouping is determined based on at least one of a pre-assigned category of the individual stimulus or an associative relationship of consecutive stimuli. For example, in the computer program product, the processing step of the method can include identifying a time interval associated with the physiological signals based on the presented stimuli and the selected profile category, grouping the physiological data corresponding to the time interval into one or more grouped data sets, and providing a statistical measure of a relationship across or within the grouped data sets using previous physiological data acquired from the subject or other subjects to generate the one or more quantitative values for the selected profile category. For example, in the computer program product, the processing step of the method can include identifying a time interval associated with the physiological signals based on the presented stimuli and the selected profile category, grouping the physiological data corresponding to the time interval into one or more initial grouped data sets, classifying each stimulus of the sequence of stimuli presented to the subject using a statistical test involving the initial grouped data sets, based on the classified stimuli, re-grouping the physiological data corresponding to the time interval into one or more grouped data sets, and providing a statistical measure of a relationship across or within the grouped data sets to generate the one or more quantitative values for the selected profile category. In some implementations, the computer implemented method of the computer program product can further include forming a modified sequence of stimuli using the generated information set for the subject, and controlling the modified sequence of stimuli presented to the subject via the device. In some implementations, the computer implemented method of the computer program product can further include receiving new physiological data representing physiological signals acquired from the subject before, during, and after the presenting the modified sequence of stimuli, and processing the new physiological data to generate an augmented information set including one or more augmented quantitative values associated with the selected profile category.

In another aspect, a system for providing a cognitive or sensory assessment includes a sensor device interfaced to a subject to detect physiological signals exhibited by the subject before, during, and after a presentation of a sequence of stimuli to the subject, the sequence of stimuli based on a cognitive-sensory profile category including a cognitive performance profile, a sensory performance profile, and a cognitive and sensory performance profile, and a data processing system in communication with the sensor device and structured to include one or more memory units and one or more processors configured to process the physiological signals as physiological data to generate an information set including one or more quantitative values associated with the cognitive-sensory profile category.

Implementations of the system can optionally include one or more of the following exemplary features. In some examples, the physiological signals detected by the sensor device does not involve a behavioral response by the subject. In some implementations, for example, the system can further include a stimulus delivery device to produce the sequence of stimuli that is presented to the subject, in which the stimuli can include at least one of a visual, auditory, olfactory, tactile, or gustatory stimulating medium. For example, the stimulus delivery device can include a display screen to generate a sequence of images. For example, the stimulus delivery device can include a speaker to generate a sequence of sounds. For example, stimulus delivery device can include an actuator to generate a sequence of at least one of olfactory, tactile, or gustatory stimuli. In some implementations, the stimulus delivery device can be configured to be in communication with the data processing system, in which the data processing system is configured to produce a machine procedure based on the generated information set, and in which the machine procedure produced by the data processing unit causes the stimulus delivery device to modify the sequence of stimuli for a next presentation to the subject. For example, the stimulus delivery device can include a desktop computer, a laptop computer, or a mobile communications device, e.g., such as a smartphone or tablet. For example, the data processing system can be configured in the mobile communications device. For example, the data processing system can be configured to produce a machine procedure based on the generated information set, in which the machine procedure actuates another device or system to perform a function derived from information contained within the generated information set. For example, the one or more quantitative values can include a quantitative score depicting a level of one or both of cognitive and sensory performance based on at least one of the subject's attention, memory, learning ability, confabulation characteristics, pattern integration ability, semantic integration ability, target detection ability, emotional valence, preference, or awareness, and in which the quantitative score depicts the level at a particular time. In some implementations of the system, for example, the sensor device can include a flexible substrate, sensor electrodes on the flexible substrate, and a transmitter unit in electrical communication with the electrodes and on the flexible substrate, in which the sensor device is configured as one or more wearable patches worn on the subject's scalp to record electroencephalogram (EEG) signals and transmit the recorded EEG signals to at least one of the data processing unit or a remote computer system. In some implementations of the system, for example, the sensor device can include electrodes attachable to the subject to receive electrical signals from the subject. For example, the sensor device can include an imaging device that captures images of the subject indicating a motion or movement of the subject. In some examples, the imaging device captures eye movement of the subject. For example, in some implementations of the system, the data processing system can include a local computer located proximate and in communication with the sensor device to receive the detected physiological signals from the sensor device, the local computer configured to conduct initial processing of the detected physiological signals to produce initial physiological signal data, and a remote computer in communication with the local computer via a communication network or link to receive the initial physiological signal data from the local computer and to process the initial physiological signal data to generate the information set including one or more quantitative values associated with the cognitive-sensory profile category. For example, the local computer can be configured to produce initial physiological signal data as individual data specific to the subject, and the remote computer can be configured to process the initial physiological signal data to produce the information set that is individualized to the subject. In some implementations, for example, the system can further include a stimulus delivery device at a location of the subject and configured to produce the sequence of stimuli that is presented to the subject, in which the stimuli includes at least one of a visual, auditory, olfactory, tactile, or gustatory stimulating medium, as well as a stimulus presentation computer in communication with the remote computer to receive data associated with or derived from the information set including one or more quantitative values associated with the cognitive-sensory profile category to modify the sequence of stimuli to the subject to produce a modified sequence of stimuli that is individualized with respect to the subject, the stimulus presentation computer coupled to the stimulus delivery device to cause the modified sequence of stimuli to be applied to the subject. In some implementations, for example, the remote computer can be configured to access physiological signal data of other subjects in one or more groups of subjects and use the physiological signal data of other subjects in processing of the initial physiological signal data to produce the information set that is individualized to the subject. For example, in some implementations, the system can further include a brain-machine interface module configured between the remote computer and the stimulus presentation computer and configured to convert the information set that is individualized to the subject into adaptive change or adjustment that is used by the stimulus presentation computer to modify the sequence of stimuli to the subject in producing the modified sequence of stimuli that is individualized with respect to the subject.

In another aspect, a method to provide a cognitive or sensory assessment of a subject includes processing one or both of physiological data and behavioral data of an individual in response to a presentation of a sequence of stimuli created based on a cognitive-sensory profile category, in which the processing generates an information set including one or more quantitative values that characterize a cognitive performance level, a sensory performance level, or a cognitive and sensory performance level of the individual. The processing includes selecting time intervals of interest within the physiological data and/or behavioral data based on the presented stimuli and the selected profile category, grouping, into one or more grouped data sets, the physiological data and/or behavioral data corresponding to the selected time intervals of interest, and providing a statistical measure of a relationship across or within the grouped data sets to generate the one or more quantitative values.

Implementations of the method can optionally include one or more of the following exemplary features. In some implementations of the method, for example, the providing the statistical measure can include using previous physiological data and/or behavioral data acquired from the individual or other individuals in one or more groups to generate the one or more quantitative values. In some implementations, for example, the method can further include forming a modified sequence of stimuli using the generated information set for the individual.

In another aspect, a system to provide a cognitive or sensory assessment of a subject includes one or more computers in communication with a remote computer device via a communication network or link. The one or more computers are configured to generate an information set including one or more quantitative values that characterize a cognitive performance level, a sensory performance level, or a cognitive and sensory performance level of an individual by processing one or both of physiological data and behavioral data acquired from the individual in response to a presentation of a sequence of stimuli created based on a cognitive-sensory profile category. The one or more computers are configured to provide the generated information set to the remote computer device.

Implementations of the system can optionally include one or more of the following exemplary features. For example, the one or more computers can process the one or both physiological and behavioral data to generate an information set, in which the processing includes selecting time intervals of interest within the physiological data and/or behavioral data based on the presented stimuli and the selected profile category, grouping, into one or more grouped data sets, the physiological data and/or behavioral data corresponding to the selected time intervals of interest, and providing a statistical measure of a relationship across or within the grouped data sets to generate the one or more quantitative values.

In another aspect, a method to provide a cognitive or sensory assessment of a subject includes selecting a cognitive-sensory profile category indicative of one or more aspects of cognitive or sensory functions, presenting a sequence of stimuli to a subject, the sequence of stimuli based on the selected cognitive-sensory profile category, acquiring physiological signals of the subject before, during, and after the presenting the sequence of stimuli to produce physiological data, and processing the physiological data to generate an information set including one or more quantitative values associated with the selected cognitive-sensory profile category.

Implementations of the method can optionally include one or more of the following exemplary features. For example, the sequence of stimuli can include at least one of a visual, auditory, olfactory, tactile, or gustatory stimulating medium based on the selected cognitive-sensory profile category. For example, the one or more quantitative values include a quantitative score depicting a cognitive and/or sensory performance level based on at least one of the subject's attention, memory, learning ability, confabulation characteristics, pattern integration ability, semantic integration ability, target detection ability, emotional valence, preference, or awareness state, in which the quantitative score depicts the level at a particular time. In some implementations of the method, for example, the processing can include identifying a time interval associated with the physiological signals based on the presented stimuli and the selected cognitive-sensory profile category, grouping the physiological data corresponding to the time interval into one or more grouped data sets, and providing a statistical measure of a relationship across or within the grouped data sets to generate the one or more quantitative values for the selected cognitive-sensory profile category. In some implementations, for example, the method can further include processing the physiological data to increase a signal-to-noise ratio of the grouped data sets. For example, the grouping can be determined based on at least one of a pre-assigned category of the individual stimulus or an associative relationship of consecutive stimuli. In some implementations of the method, for example, the processing can include identifying a time interval associated with the physiological signals based on the presented stimuli and the selected cognitive-sensory profile category, grouping the physiological data corresponding to the time interval into one or more grouped data sets, and providing a statistical measure of a relationship across or within the grouped data sets using previous physiological data acquired from the subject or other subjects to generate the one or more quantitative values for the selected cognitive-sensory profile category. In some implementations of the method, for example, the processing can include identifying a time interval associated with the physiological signals based on the presented stimuli and the selected cognitive-sensory profile category, grouping the physiological data corresponding to the time interval into one or more initial grouped data sets, classifying each stimulus of the sequence of stimuli presented to the subject using a statistical test involving the initial grouped data sets, based on the classified stimuli, re-grouping the physiological data corresponding to the time interval into one or more grouped data sets, and providing a statistical measure of a relationship across or within the grouped data sets to generate the one or more quantitative values for the selected cognitive-sensory profile category. In some implementations, for example, the method can further include forming a modified sequence of stimuli using the generated information set for the subject, and presenting the modified sequence of stimuli to the subject. In some implementations, for example, the method can further include acquiring physiological signals of the subject before, during, and after the presenting the modified sequence of stimuli to produce new physiological data, and processing the new physiological data to generate an augmented information set including one or more augmented quantitative values associated with the selected cognitive-sensory profile category. In some implementations, for example, the method can further include creating an initial sequence of stimuli for each of the cognitive-sensory profile categories. In some implementations, for example, the method can further include, based on the generated information set for the subject, generating an interaction between a machine and the subject.

BRIEF DESCRIPTION OF THE DRAWINGS

FIGS. 5A and 5B show data plots showing the means and standard deviations of an individual exemplary subject from two exemplary electrode channels under two different visual stimulus conditions.

FIG. 6 shows a data plot and corresponding table depicting the exemplary performance of the subject-supervised classifier for the visual stimulus paradigm.

FIGS. 28A and 28B show images and data plots of exemplary results from implementation of the exemplary method using an exemplary rigid electrode EEG system.

FIGS. 29A and 29B show images and data plots of exemplary results from implementation of the exemplary method using an exemplary flexible electronics sensors EEG system.

DETAILED DESCRIPTION

Figure 1A:
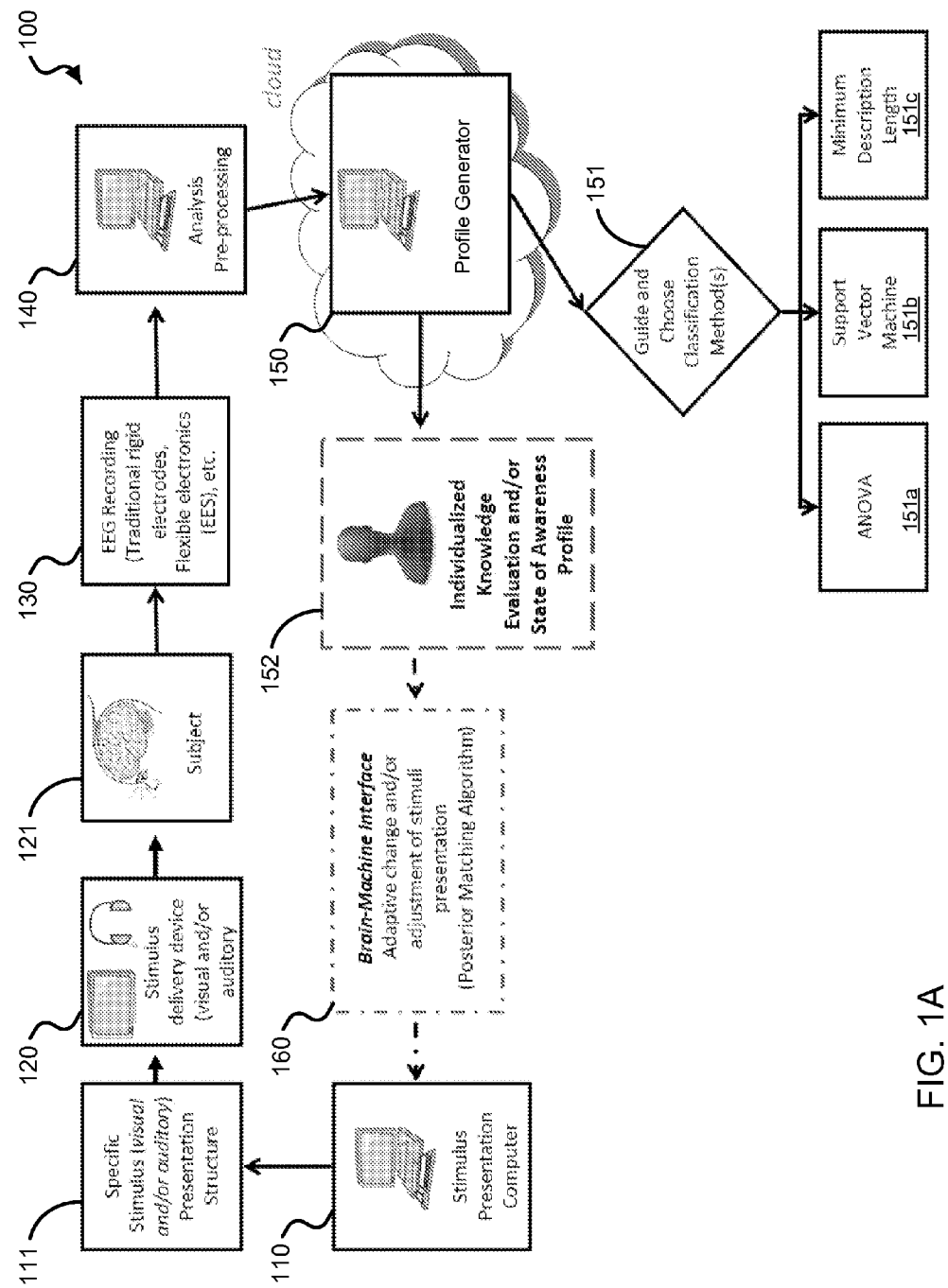
FIG. 1A shows a diagram of an exemplary system of the disclosed technology for acquisition, analysis, and evaluation of physiological signals to produce an individual or group knowledge and/or state of awareness profile.

Establishing a reliable correlation between one's brain signals and his/her cognitive/psychological states (e.g., thoughts) is a valuable and desired goal for a wide variety of applications. These correlations, extensively explored in fundamental sciences, have been the focus of various translational attempts into specialized applications such as assessment of cognitive impairment and enabling the physically impaired to communicate.

Some systems to characterize cognitive and psychological states have relied upon various behavioral and brain imaging techniques, e.g., such as functional resonance magnetic imaging (fMRI) and electroencephalography (EEG). For example, fMRI is an indirect measure of brain function by correlated metabolic function (e.g., oxygen consumption in the blood flow), whereas EEG is a direct measure of brain activity by recording changes of the electrical fields present at the scalp, deriving from electrical activity produced by neural cells. Existing techniques typically focus on one type of "brain reading", and as such, are designed only for that purpose.

Independent of the specific brain imaging system used, current techniques infer individual cognitive information mostly using a methodological framework that relies on the tested subject "operant behavior" (e.g., the subject is requested to produce a behavioral response to the presented stimuli) and infer knowledge based on, and limited to, a priori tested specific knowledge categories for which "brain response templates" are created by a mathematical algorithm. Such techniques are limiting in several ways, including requiring an active participation and collaboration from the subject, evaluating the knowledge by the types and number of categories for which the mathematical algorithm was "trained" on, and using a subject-specific template (i.e., only applicable to a single subject).

For determining sensory and/or cognitive information about a subject, the methodology should consider the type of stimuli used to evoke a subject's response (e.g., for visual stimuli: images, written words, etc.; for auditory stimuli: spoken words, animal vocalizations, synthesized sounds, etc.), duration, inter-stimuli interval, number of repetitions of each presentation, sound or brightness or contrast levels, digital marker associated with the onset of presentation of each stimuli, the recording sensors and systems. Also, the physiological parameter(s) of use (e.g., voltage, power, frequency, etc.), the related time window for analysis, and the analysis structure can affect the brain signal recordings and correlated cognitive evaluation. Deviations or mistakes from one or multiple of these parameters can make the difference between a useful or artifact driven, useless method.

Disclosed are methods, systems, and devices for using physiological (e.g., brain signals) and/or behavioral information to generate cognitive and/or sensory profiles pertaining to individual and/or group cognitive and/or sensory performance, psychological states, and behavioral preferences.

For example, the disclosed methods and systems can be used for assessing and inferring individual conceptual knowledge (e.g., how someone classifies different information and what knowledge they may have on a specific topic), state of awareness (e.g., how conscious, or not an individual might be without showing any overt behavior) and psychological and behavioral preferences (e.g., individual personal increased attention and/or preferences for certain items, such as shoes, cars, books, etc., amongst others). For example, the disclosed technology can be used in a variety of education, health, entertainment, and marketing applications.

In some implementations, for example, stimuli-elicited electroencephalography (EEG) signal data and behavioral response data are used together to generate a novel and specialized set of testing and analysis methods (e.g., including, but not limited to, visual and auditory stimulation, machine learning and other statistical algorithms, etc.) to correlate individual brain signals with cognitive information and to potentially guide brain-machine interfaces.

The disclosed methods can employ brain markers that are common for every person. For example, the described methods and systems can use presentation stimuli that are not subject- or category-specific. Implementations of the disclosed technology can allow for inference of knowledge and awareness state that is not limited to a priori categories, can be generalized across every person, and can extract information in a completely passive way (e.g., not requiring the person's compliance or any kind of overt behavioral response). This method can be used for both direct assessment/evaluation of an individual's sensory and cognitive performance and state of awareness, as well as a drive for brain-machine interface systems. For example, implementation of the disclosed systems and methods can provide personalized cognitive and/or sensory performance evaluations, and in some implementations, group cognitive and/or sensory performance assessments.

The disclosed technology is scalable and applicable to a wide range of applications and can provide a solution for 'non-tangible' brain reading or evaluation cases (e.g., where individuals are not able or willing to produce overt behavioral responses). For example, the disclosed systems and methods can be used in a clinical setting on a patient in a coma or otherwise nonresponsive, e.g., including instances of patients on life support systems, to provide a profile on the patient's state of awareness and/or cognitive abilities.

The disclosed systems and methods can be effectively used by non-experts to provide a cognitive and/or sensory profile of a subject or subjects, e.g., such as users whom are neither neuroscientists, psychologists, nor specialized physicians. For example, the disclosed systems can be used by general consumers, with safety and accuracy, allowing for the freedom to use in a wide variety of contexts and locations, significantly reducing the cost and requirements of use. For example, the non-expert users can implement the disclosed systems and methods to obtain awareness and mental information profiles of the evaluated person(s), e.g., either themselves or others.

Exemplary Embodiments of the Disclosed Methods and Systems

FIG. 1A shows a diagram of an exemplary modular system 100 of the disclosed technology for acquisition, analysis and evaluation of physiological signals to produce an individual or group cognitive and/or sensory profile. For example, the system can be implemented to provide a cognitive performance profile, a sensory performance profile, and a cognitive and sensory performance profile indicative of a subject's cognitive and/or sensory ability at the time of the assessment. For example, the type of cognitive and/or sensory profile can be selected by the user (e.g., such as the subject or a system operator) to provide a set of information including a quantitative level of cognitive and/or sensory performance, e.g., including, but not limited to attention, memory, learning, confabulation, pattern integration, semantic integration, target detection, emotional valence, preference, and state of awareness. The system allows an operator to select the type of profile to be produced.

In some implementations, the system can be implemented to provide the cognitive and/or sensory profile using only physiological data acquired from the subject, e.g., with no overt behavioral response elicited from the subject. In other implementations, the system can be implemented to provide the cognitive and/or sensory profile using behavioral data or both physiological and behavioral data from the subject. In some implementations, the system can be implemented to provide the cognitive and/or sensory profile including previously acquired physiological and/or behavioral data from the subject, or other subjects (e.g., group data). The system can thereby, for example, be implemented to provide a cognitive and/or sensory profile about a group.

As shown in FIG. 1A, the system 100 is configured to include independent modular units or devices that can be configured in a variety of different embodiments.

The system 100 includes a stimulus presentation module 110 to configure a specific stimulus presentation structure 111 to effectuate a presentation of a stimulus or a sequence of stimuli to a subject 121. In some examples, the stimulus presentation module 110 is embodied in a computing device, e.g., including a processor and memory unit. For example, the stimuli can include any stimulus type, including a visual, auditory, olfactory, tactile, or gustatory stimulating medium. The specific stimulus presentation structure 111 can be configured to include, but is not limited to, a particular type or types of stimuli, the duration of presentation of the stimuli, an inter-stimuli interval, a number of repetitions (if any) of each presentation, magnitude and/or frequency parameters associated with type of stimuli (e.g., intensity of sound or brightness or contrast level of light), a digital marker associated with the presentation of each stimuli, and a label or category of the stimuli (e.g., target or non-target).

The system 100 can include a stimulus delivery module 120 in communication with the stimulus presentation module 110 to present the stimulus or the sequence of stimuli to the subject 121, e.g., based on the stimulus presentation structure 111. For example, the stimulus delivery module 120 can include at least one of a visual display, an auditory speaker, and an actuator to provide an olfactory, tactile, and/or gustatory stimulus. In some implementations, for example, the stimulus presentation module 110 and the stimulus delivery module 120 can be configured in the same device, e.g., such as a computer or mobile communication and/or computing device.

The system 100 includes a physiological and/or behavioral data acquisition module 130 to acquire physiological signals and/or behavioral signals of the subject 121 before, during, and/or after the presentation of the stimuli or sequence of stimuli via the stimulus delivery module 120. For example, the physiological and/or behavioral data acquisition module 130 can include, but is not limited to, an electroencephalography (EEG) system, an electrocardiography (ECG) system, an electromyography (EMG) system, an electrochemical sensing system, and an eye tracking system, among others. In some implementations, for example, the physiological and/or behavioral data acquisition module 130 can include physiological sensors, e.g., EEG, ECG, EMG, electrochemical, or other types of sensor devices, coupled to a signal acquisition device, e.g., such as an analog or digital amplifier coupled to a memory. For example, the physiological and/or behavioral data acquisition module 130 can be configured in a standard EEG system with rigid electrodes or a portable EEG system using flexible electronics that can be worn on the subject 121. For example, the physiological and/or behavioral data acquisition module 130 can be configured in a standard EMG system with rigid electrode or a portable EMG system using flexible electronics that can be worn on the subject 121, e.g., capable of detecting movements associated with drowsiness or facial expressions.

The system 100 includes an analysis pre-processing module 140 to receive the acquired physiological signals and/or behavioral signals as data, and in some implementations, to perform pre-processing analysis techniques on the acquired data. For example, the analysis pre-processing module 140 can be implemented to identify exemplary onset markers in the physiological data (e.g., EEG data), segment the physiological data, filter raw signal data to increase signal to noise, etc. In some implementations, for example, the analysis pre-processing 140 can be embodied in a computer device in communication with an exemplary device or system embodying the physiological and/or behavioral data acquisition module 130. In some implementations, for example, the analysis pre-processing 140 can be configured in the same exemplary device or system that embodies the physiological and/or behavioral data acquisition module 130.

The system 100 includes a profile generation module 150 to process the physiological and/or behavioral data to provide a cognitive or sensory assessment of the subject 121, or in some examples, of a group. For example, the profile generation module 150 processes the physiological and/or behavioral data to generate an information set 152 that includes one or more quantitative values that are associated with the selected profile category, e.g., such as a knowledge evaluation or state of awareness profile. For example, the information set 152 provides more than a measure of psychological and neurophysiological natural events. For example, the profile can provide an individual (or group) assessment of one's (or group's) level of knowledge of specific issues (e.g., determination of a given person knowledge about a specific topic, event, learned skill or even preference) and/or state of conscious (or unconscious) awareness.

Figure 1B:
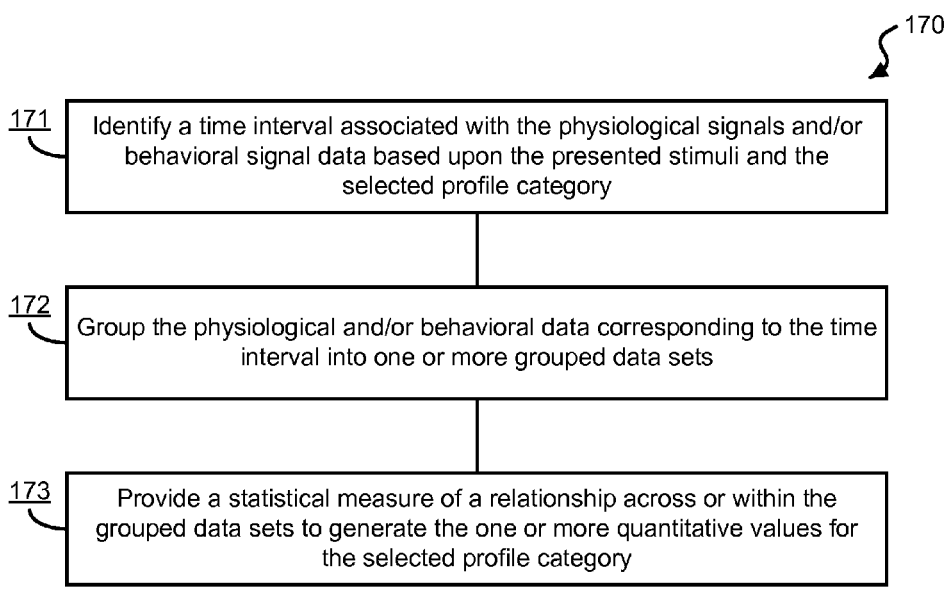
FIGS. 1B-1D show process diagrams of exemplary methods to generate a quantitative information set of an exemplary cognitive and/or sensory profile.

FIG. 1B shows a process diagram of an exemplary method 170 to generate the information set associated with the cognitive and/or sensory profile, e.g., implemented by the profile generation module 150. The method 170 can include a process 171 to identify a time interval associated with the physiological signals and/or behavioral signal data based upon the presented stimuli and the selected profile category. For example, a time interval can include contiguous, discontinuous, continuous, discrete, or single time points. The method 170 can include a process 172 to group the data (e.g., physiological and/or behavioral) corresponding to the time interval into one or more grouped data sets. For example, the process 172 can include grouping the physiological and/or behavioral data based on a pre-assigned category of the individual stimulus and/or an associative relationship of consecutive stimuli. The method 170 can include a process 173 to provide a statistical measure of a relationship across or within the grouped data sets to generate the one or more quantitative values for the selected profile category. In some implementations, for example, the method 170 can include a process to enhance the signal of the physiological and/or behavioral data in the grouped data sets.

Figure 1C:
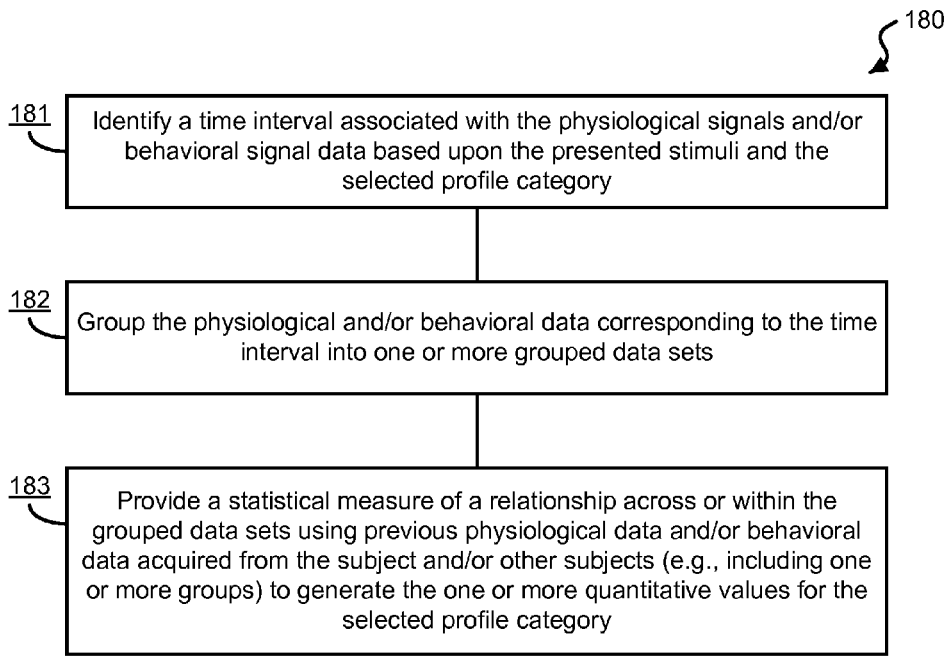

FIG. 1C shows a process diagram of an exemplary method 180 to generate the information set associated with the cognitive and/or sensory profile using previous individual and/or group information, e.g., implemented by the profile generation module 150. The method 180 can include a process 181 to identify a time interval associated with the physiological signals and/or behavioral signal data based upon the presented stimuli and the selected profile category. The method 180 can include a process 182 to group the data (e.g., physiological and/or behavioral) corresponding to the time interval into one or more grouped data sets. For example, the process 182 can include grouping the physiological and/or behavioral data based on a pre-assigned category of the individual stimulus and/or an associative relationship of consecutive stimuli. The method 180 can include a process 182 to provide a statistical measure of a relationship across or within the grouped data sets using previous physiological data and/or behavioral data acquired from the subject and/or other subjects (e.g., including one or more groups) to generate the one or more quantitative values for the selected profile category.

Figure 1D:
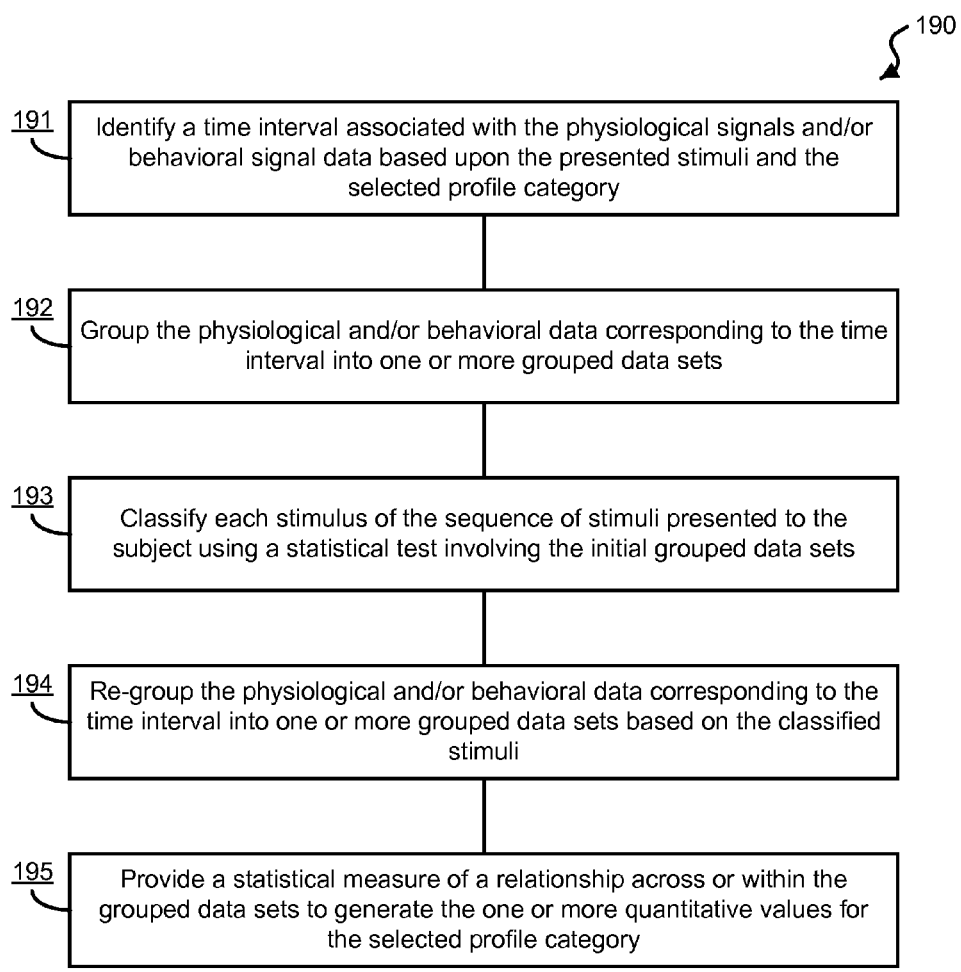

FIG. 1D shows a process diagram of an exemplary method 190 to generate the information set associated with the cognitive and/or sensory profile using a guided classification technique, e.g., implemented by the profile generation module 150. The method 190 can include a process 191 to identify a time interval associated with the physiological signals and/or behavioral signal data based upon the presented stimuli and the selected profile category. The method 190 can include a process 192 to group the data (e.g., physiological and/or behavioral) corresponding to the time interval into one or more initial grouped data sets. The method 190 can include a process 193 to classify each stimulus of the sequence of stimuli presented to the subject using a statistical test involving the initial grouped data sets. The method 190 can include a process 194 to re-group the physiological and/or behavioral data corresponding to the time interval into one or more grouped data sets based on the classified stimuli. The method 190 can include a process 195 to provide a statistical measure of a relationship across or within the grouped data sets to generate the one or more quantitative values for the selected profile category.

In some examples, the profile generation module 150 can implement guided classification algorithms with context specific parameters to guide and choose from a variety of classification and statistical methods, e.g., including, but not limited to, ANOVA based techniques 151a, support vector machine based techniques 151b, and minimum description length techniques 151c, among others. In some implementations, the profile generation module 150 can be embodied on a computer system or communication network (referred to as 'the cloud') that includes one or more remote computational processing devices (e.g., servers in the cloud).

The system 100 includes a brain-machine interface module 160 to refine the generated cognitive and/or sensory profiles and/or actuate an interaction between a user and a machine. In one example, the brain-machine interface module 160 can provide a feedback delivery of a new stimulus or multiple stimuli to the stimulus presentation module 110 based on the cognitive and/or sensory profile of an individual subject or group subject that has been generated from the profile generation module 150, e.g., from an on-going implementation of the system 100 or a previously generated profile by the system 100. For example, the brain-machine interface module 160 can adaptively change or design stimuli paradigms that optimally extract information from the subject that is analytically processed to maximize a desired objective. For example, some implementations of the brain-machine interface module 160 can include, but are not limited to, assisted-learning and target detection applications.

In some implementations of the system 100, the profile generation module 150, the stimulus presentation module 110, the stimulus delivery module 120, and the brain-machine interface module 160 (and in some instances, the data acquisition module 130) can be embodied in a single computing system, e.g., a desktop computer, a laptop computer, or a mobile communications device including a smartphone or tablet. In other implementations, the modules 150, 110, 120, and 160 can be configured in two or more computing devices in communication with each other and including various combinations of the modules 150, 110, 120, and 160.

In some implementations, the system 100 can be configured to just include the physiological and/or behavioral data acquisition module 130 and the profile generation module 150. In such exemplary implementations, the system 100 can use environmental stimuli (e.g., light, sounds, smells, tastes, and/or tactile contacts) that are presently available in the subject's surroundings. In such examples, the system 100 can be embodied on a single computing device, e.g., where the module 130 is configured to receive behavioral responses from the subject and/or record physiological data via inputs of the device.

Exemplary Implementations of the Disclosed Methods and Systems

Described are exemplary implementations of the disclosed methods and systems for providing a cognitive and/or sensory assessment of a subject, e.g., including at least one of the following exemplary profile categories: cognitive performance profile, a sensory performance profile, a cognitive and sensory performance profile, and/or a state of awareness profile. The described exemplary implementations include eliciting and extracting various brain ERPs (e.g., N400 and P300) measured by EEG recordings using visual stimuli and auditory stimuli to produce an information set providing quantitative values corresponding to the cognitive performance, sensory performance, and/or awareness state profile. In some examples of the disclosed methods and systems, eye tracking data can be used in addition to or alternatively to the exemplary EEG recording physiological data.

For example, specific stimuli sets are presented while recording EEG signals from the subject to elicit event-related potentials of interest, as well as correlated neural frequency oscillations. The exemplary ERPs used in the exemplary implementations include, but are not limited to, the N400 and the P300, as well as ERP responses identified by us in relation to the cognitive processing of a feeling/notion of reward. As described in the sections below, exemplary applications of the disclosed methods and systems use these three ERPs as illustrative examples to described how the exemplary method can be implemented, e.g., stimuli design and presentation, physiological signal (e.g., EEG) recording, physiological data (e.g., ERP) analysis, and cognitive and/or sensory profile generation (e.g., including inferred cognitive and/or awareness states). In one example, the application of an exemplary cognitive and/or sensory profile generation method is implemented for N400 measures using visual and/or auditory stimuli. In another example, the application of an exemplary cognitive and/or sensory profile generation method is implemented for P300 measures, and an ERP associated with experiencing "reward", using visual and/or auditory stimuli. Additionally, the application of the exemplary cognitive and/or sensory profile generation method is implemented using different EEG recording techniques, e.g., including non-portable conventional systems and wearable electronics systems. Also, the exemplary cognitive and/or sensory profile generation method is applied to a group of people (e.g., as shown in the N400 example implementations) as well as in a single individual (e.g., as shown in the P300 example implementations). The disclosed cognitive and/or sensory profile generation methods and systems can be used to measure brain markers, but in addition, it evaluates and transforms this information into a new type of purposeful data that creates an individual knowledge evaluation and/or state of awareness profile. Moreover, in some implementations, for example, the disclosed methods and systems can use this profile to guide a brain-machine interface system.

Also described are patterns classifiers (e.g., algorithms implemented in computer systems, e.g., using software) in which each feature modulation is guided by the specific task at hand as well as its underlying psychological and physiological mechanisms. These exemplary classifiers class can use identifiable cognitive and physiological parameters to structure the relevant features in a classification methodology to infer brain states from neural signals. For example, the exemplary classifiers can be applied in brain-reading applications as part of a sequential process of providing stimuli, acquiring neural signals, and repeating. The details of how these stimuli are being provided (e.g., context) can affect the cognitive state, which can in turn affect the statistics of the acquired signals. The exemplary classifier can be guided by the context, in which the features can be modulated accordingly.

I. N400

The N400, discovered in humans more than 30 years ago, was identified as a marker for the processing of meaningful relations among perceived items, such as words, pictures, symbols, etc. The label "N400" of this type of brain wave was given due it is negative-going deflection that peaks at approximately 400 millisecond after an item's onset. N400 amplitudes are smaller to items that share a close semantic association than to items that do not (e.g., to "dog" following "cat" than following "table"). As described below, the disclosed methods can be applied to elicit and extract the N400 ERP (e.g., with auditory stimulation, visual stimulation, both, or other stimuli mediums, including, but not limited to olfactory, tactile, or gustatory) and be used to subsequently infer cognitive relevant information.

I.1. N400 with a Visual Stimuli Paradigm

I.1.1. Exemplary Stimuli

In one example implementation, examined were the brain responses from 37 adult subjects to eight categories of images (e.g., including animal bodies, animal faces, human faces, monkey faces, fruits, household objects, laboratory objects and places). For example, there were eighteen stimulus exemplars (e.g., images) used per category for a total of 144 exemplars. Images were divided into twelve presentation blocks, and each subject was presented six randomly chosen blocks. The pool of images was obtained from various resources, and the images were cropped using photo editing software and placed onto a white background measuring 356×356 pixels (13.18°×13.18° visual angle at 57 cm distance from a display monitor). The stimulus was placed onto a full screen, black monitor background at a resolution of 1024×768 pixels.

All stimuli were controlled for luminance using the Weber contrast formula, in which $L_c$ and $L_b$ represent the luminance values of the content and the white background. A computer implemented process used (e.g., programmed using a MATLAB script) the aforementioned formula and adjusted the luminance of the content to a 50% contrast when compared to the white background. For example, the process first separated the content from its white background. In this example, two criteria were used to determine whether a pixel would be identified as part of the background: first, all background pixels were required to have RGB values equal to 255 (e.g., maximum of an 8-bit grayscale image); and second, all background pixels were required to be directly adjacent to an already identified background pixel. All remaining pixels not identified as background were considered as content. The process then calculated the mean luminance of the content and adjusted its value by either adding or subtracting RGB values to every content pixel in order to achieve a 50% contrast.

After controlling for luminance, another computer implemented process (e.g., programmed using a MATLAB script) was used to place a centrally positioned fixation dot on each stimulus exemplar. For example, this helped the subject to maintain fixation and minimize any frequent eye saccades. This exemplary process first measured the dimensions of an uploaded image. It used these measurements to calculate the center of the image and subsequently create a fixation dot using the standard equation of a circle. Pixels within a seven pixels length radius around the center were altered by changing the pixels' red gun to 255, the green gun to 0, and the blue gun to 0.

Lastly, the two exemplary methods were used to create a fixation dot and a blue square stimulus. For example, for the fixation dot, another computer implemented process (e.g., programmed using a MATLAB script) was used to create a black background image (e.g., red gun equal to 0; green gun equal to 0; blue gun equal to 0) with a height and width of 350 pixels. Then, the exemplary script ran a nested for-loop using the standard equation of a circle to alter pixels within a seven pixels length radius to red, e.g., by changing the image's red gun to 255, the green gun to 0, and the blue gun to 0. For example, for the blue square stimulus, imaging software was used to create a 157×157 pixel sized image, e.g., whose red gun was equal 0, green was equal 0, and blue was equal 255.

I.1.2. Subject Preparation for EEG Recording

To prepare the exemplary subjects for EEG recording, each subject was seated in a chair in a recording chamber to begin an EEG capping process. For example, this process involved placing a traditional EEG cap on the subject's head and securing it with an elastic chin strap. In some examples, either a 56 cm or a 58 cm diameter cap was used, based on the estimated size of the subject's head. Next, Signa electrode gel (e.g., from Parker Laboratories) was injected using a curved, plastic syringe under each of the cap's electrodes to create a conductive bridge between the electrode itself and the subject's scalp. Also, for example, wooden Q-tips were used to massage the gel in order to build a stronger conductance by lowering the impedance. For example, use of this technique lowered the impedance levels to <5 kΩ for each electrode, e.g., including the ground and reference. Before starting the exemplary implementation using EEG recordings, subjects were seated in front of the presentation monitor and asked to just maintain visual fixation on a red, central fixation dot throughout the duration of the experiment and restrict their motor movements as much as possible to prevent motion artifacts in the neurophysiological data. Afterwards, the recording room's lights were then dimmed, and the stimulation process and EEG recordings began.

I.1.3. Exemplary Stimuli Presentation Process

The exemplary stimulus presentation paradigm that was used in this example stimuli presentation process was programmed using Cogent 2000, e.g., a MATLAB toolbox designed for presenting stimuli and recording responses with precise timing. The exemplary stimulus presentation structure included 300 pseudo-randomly presented images, e.g., shown serially (twenty-five repetitions per exemplar) per presentation block. For example, each image was presented for 750 ms, followed by a randomly jittered inter-stimulus interval (ISI) of 750 ms to 1000 ms. A red, central fixation dot was present during each stimulus presentation and ISI, e.g., in order to aid the subject in maintaining fixation. To mark each stimulus onset, two triggers were sent from the presentation computer running the exemplary stimulus presentation paradigm via parallel port. For example, the first was sent to the EEG recording computer to mark the stimulus onset relative to the ongoing neurophysiological recording. For example, the second was sent to the ISCAN eye-tracking computer (e.g., ISCAN ETL-200) to mark the stimulus onset, its entire duration, and its offset relative to the eye-tracking recording. Each trigger coded information regarding the object category in which the at-hand stimulus belonged to. For example, after every four to six trials, a blue square was presented to the subject for 1500 ms. At this point, the fixation dot was not displayed. For example, in the case of human subjects, this blue square signaled a "mini-recess/Reward" in which subjects were indicated that they were doing well and allowed to momentarily rest, scratch an itch, adjust their seating position, etc., if they so desired. In the exemplary case of non-human primate (NHP) subjects, this blue square signaled a juice reward. After the offset of the blue square, the fixation dot would return and hold for 750 ms before the start of the next stimulus presentation. For example, this short pause was used to ensure that the stimulation from the onset of the fixation dot would not interfere with the stimulation from the subsequent image exemplar.

The exemplary code of the stimulus presentation process began by randomly permutating the presentation order of the 300 images, e.g., using MATLAB's "randperm( ) function". Then, it randomly calculated the ISI for each stimulus using the "randi( ) function". The display, log file, and parallel port were then initialized and configured. Each stimulus exemplar was loaded into a memory buffer, e.g., including the fixation dot, blue square, and black screen (displayed during the ISI after each stimulus). For example, the stimulus presentation included a loop. First, the exemplar-to-be-presented was calculated by iterating down the permutated presentation order. Then, based on the exemplar's membership to one of the four object categories, the appropriate trigger code was calculated and sent to the EEG recording computer and the ISCAN eye-tracking computer. Visual stimuli were presented using a Sony Trinitron GDM-C520 monitor.

Figure 2:
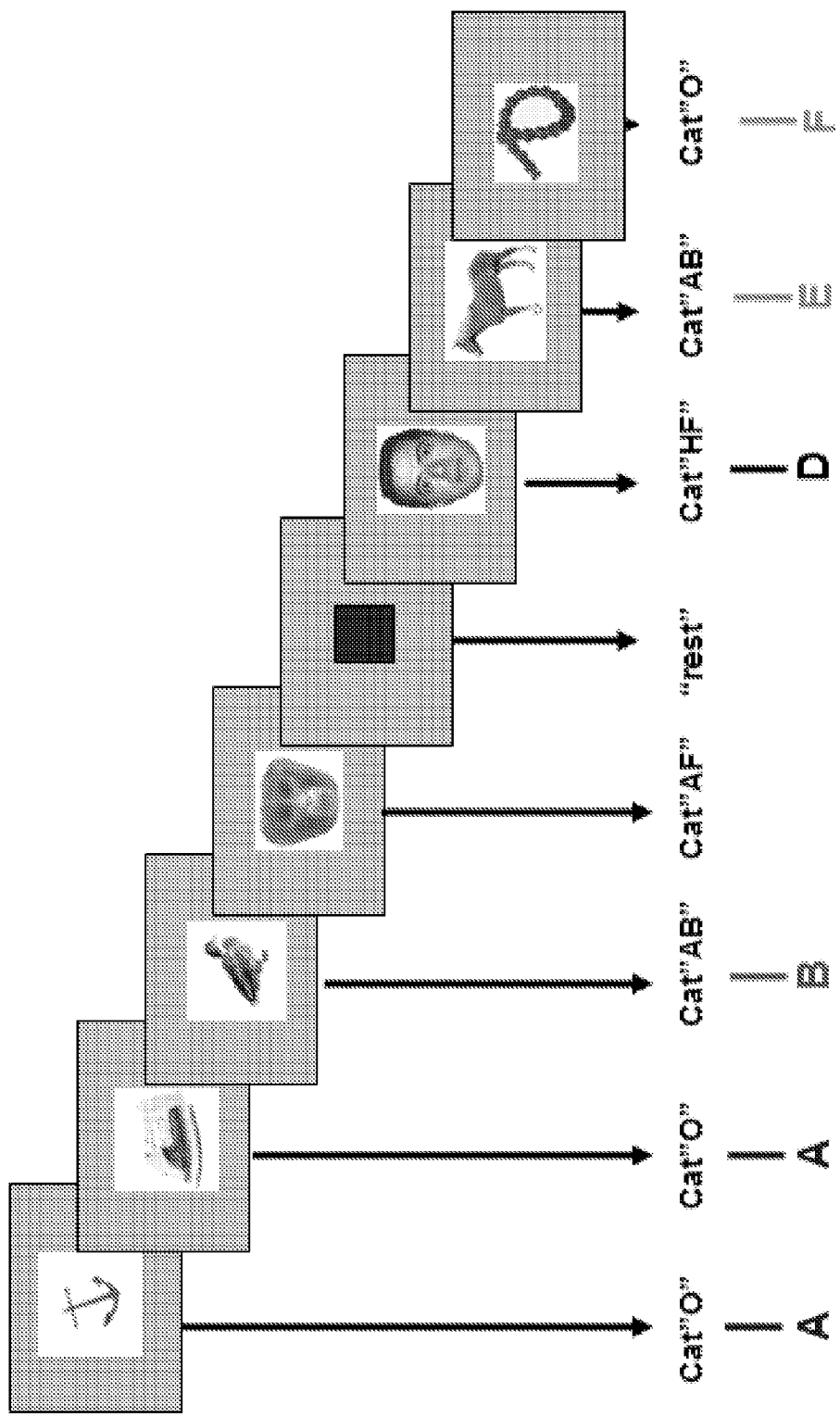
FIG. 2 shows a diagram of an exemplary sequence of presented visual stimuli.

FIG. 2 shows a diagram of an exemplary sequence of presented visual stimuli. This diagram portrays images of specific presented exemplars and the pre-programmed pseudo-randomized order of presentation. Having an adequate stimuli presentation structure for each sensory and cognitive profile of interest is an intrinsic and important part of the disclosed method. In this example, the relevant aspect is to what conceptual category (Cat) does each image belong to, for example, such as: Cat "O"—Objects; Cat "AB"—Animal Bodies; Cat "AF"—Animal Faces; and Cat "HF"—Human Faces. The exemplary stimulus presentation structure can be configured to include repetition of a given category (e.g., AA) and subsequent change in category (e.g., B), which is a primary feature of the stimulus presentation structure and the subsequent analysis techniques, as described in the later in this patent document.

I.1.4. Exemplary Brain Waves (EEG) Recordings

In some implementations, a traditional EEG system with rigid electrodes was used to acquire brain waves. The exemplary EEG system included a BrainAmp DC 32-channel system; BrainVision Recorder; Fast n Easy 32-channel EEG recording cap size 56 cm; Fast n Easy 32-channel EEG recording cap size 58 cm; PCB Ribbon Cable for BrainCap-MR with 5 k resistors; and BrainCap MR Box 1.2.

I.1.5. Exemplary Pre-Processing Analysis Techniques

The exemplary analysis pre-processing techniques of the disclosed methods using a visual stimuli paradigm can include techniques for processing the marker data. For example, after each recording session, the exemplary EEG recordings system produced three files: data file (.eeg), header file (.vhdr), and marker file (.vmrk). The marker files contained the event triggers for each stimulus onset. For human subjects, for example, each object category was labeled with the following marker codes: implementation one—animal bodies="S 1", fruits="S 2", human faces="S 3", human household objects="S 4"; and implementation two—animal faces="S 1", rhesus macaque faces="S 2", places="S 3", lab-related objects="S 4." For NHP subjects, for example, each category was labeled with the following marker codes: NGP implementation one—animal bodies="S 1", fruits="S 2", rhesus macaque faces="S 3", lab-related objects="S 4"; and NHP implementation two—animal faces="S 1", human faces="S 2", places="S 3", household objects="S 4.". The analysis pre-processing techniques includes a first process (e.g., programmed using a MATLAB script) to load in the marker files and examine the first time an exemplar was presented. These trials were re-coded with an "A1" format. For example, the first presented human face exemplar was re-coded as [A1humanface]. Next, because images were presented pseudo-randomly, the marker files produced by EEG recording system were examined using a second process (e.g., programmed using a MATLAB script) to search for cases in which there was a repetition of an object category followed by a change in object category. For example, a possible N400 trial can be [fruit; fruit; human face]. These cases were re-coded by the exemplary MATLAB script using an A, AA, B format (e.g., "A" and "AA" representing exemplars from the same category and "B" representing exemplars from a different category). To continue with the example stated above, [fruit; fruit; human face] would be re-coded as [Afruit; AAfruit; Bhumanface]. Then, a third process (e.g., programmed using a MATLAB script) was implemented to find instances in which there was no repeat of category. For example, a possible case can be [fruit; human face; animal body]. These particular instances would be re-coded by the MATLAB script using a C, D, E format (e.g., "C," "D," and "E" each representing a different object category). In this exemplary case, [fruit; human face; animal body] would be re-coded as [Cfruit; D; human face; Eanimal body].

In examples using eye tracking data, the exemplary analysis pre-processing techniques of the disclosed methods can include techniques for storing and processing the eye data. In such examples, after each recording session, each subject's eye-tracking data can be saved as an ASCII .tda file. These data files can be first processed by a computer implemented process (e.g., programmed using a MATLAB script) that marks the onset and offset of each stimulus using the codes "100" and "101", respectively. Subsequently, the eye-tracking data files can be loaded into ILAB, e.g., which is a [MATLAB toolbox] program for postexperimental eye movement analysis. For each data file, for example, the positioning data values can be calibrated by correlating the resolution coordinates of the ISCAN eye-tracking camera with the resolution coordinates of the presentation monitor. Afterward, the presentation monitor parameters can be inputted, e.g., setting the distance between the monitor and the subject at 57 cm, the monitor width at 40.64 cm, and the monitor height at 30.48 cm. Each subject's eye fixation performance can be calculated by executing a gaze maintenance check within ILAB. For example, a region of interest (ROI) can first be set using a 5°×5° (visual angle) square window centered on the red fixation dot. Using this ROI, subjects can be required to maintain fixation within this window for the entire duration of the stimulus (e.g., 750 ms) for at least 75% of total image presentations. In some examples, subjects who fail to perform at or above this performance level can be excluded from the exemplary EEG/ERP analysis. The gaze maintenance function can include the following steps, e.g., (1) requiring a fixation for the entire duration of the stimulus; (2) selecting the region of interest centered on the central fixation dot; and (3) exporting the gaze maintenance results to a processing unit (e.g., including the MATLAB workspace) to calculate the subject's percentage of accuracy.

The exemplary analysis pre-processing techniques of the disclosed methods include techniques for general group statistical analysis. In the exemplary implementations described herein, a combination of MATLAB and Statsoft Statistica (version 8.0) software was used for statistical analyses. After data processing and analysis, the BrainVision Analyzer of the exemplary EEG recording system exported text files containing data values in regards to condition, subject, trial, electrode channel, peak latency, peak voltage, and mean voltage amplitude. The exported text files were loaded into a computer implemented program (e.g., a MATLAB program) to sort and organize the data in a more accessible format. Specifically, for example, the exemplary computer implemented program allows one to more easily select data by column, e.g., using MATLAB's variable editor. After selecting, data were copied and pasted into Statistica data spreadsheets. In some implementations, for example, repeated measures ANOVAs were performed on each spreadsheet, e.g., comparing the effects of AA versus B, AA versus D, and B versus D across subjects and across object category for each species. For human subjects, for example, each spreadsheet was specific to the following, e.g., (1) experiment: experiment 1, experiment 2, or experiments 1 and 2 combined (using the total number of subjects from experiments 1 and 2); and (2) electrode channel: F3, Fz, F4, P7, P8, Fp1, Fp2, Tp10, F3+Fz+F4 (electrode pool), P7+P8 (electrode pool), or Fp1+Fp2 (electrode pool). Likewise, for NHP subjects, for example, each data spreadsheet was specific to the following, e.g., (1) experiment: experiment 1, experiment 2, or experiments 1 and 2 combined (using the total number of subjects from experiments 1 and 2); and (2) electrode channel: Cz, F1, FT3, O1, O2, Pz, Cz+Pz (electrode pool), Cz+Pz+O1+O2 (electrode pool), O1+O2 (electrode pool). For example, for single electrode channel analyses, one-way (factor 1: condition) repeated measures ANOVAs were performed. For example, for pooled electrodes analyses, two-way repeated measures (factor 1: condition; factor 2: electrode channel) ANOVAs were performed. Subject number was used as a categorical predictor for both subject pools. Statistical analysis of the semantic priming and violation conditions (e.g., "AA", "D", and "B") reflected in the N400/N300 ERP effect (e.g., between 276 and 376 ms) in frontal and parietal electrodes, revealed the following exemplary results. Electrode (Fz) "AA vs B" produced $F(1, 4175)=4.4527$ and a P-value of 0.0349; "AA vs D" produced $F(1, 4018)=6.8894$ and a P-value of 0.0087; electrodes (P7 and P8) "AA vs B" produced $F(1, 4175)=11.669$ and a P-value of 0.00064; "AA vs D" produced $F(1, 4018)=13.297$ and a P-value of 0.00027.

For example, the disclosed methods can 'passively' acquire and analyze physiological data (e.g., including neurophysiological data) of the subject before, during, and after presentation of stimuli. The disclosed methods can be implemented in ways that are unlike traditional approaches to elicit the N400 ERP, such as those that use "operant" paradigms (e.g., operant paradigms that have the subject to perform an active discrimination and behavioral response). For example, in acquiring physiological signal data from a subject using the disclosed method, the subject is not required to provide any overt behavioral response—all he/she may do is passively look at a presentation (display) screen. For example, based in implicit modulation of amplitude of different brain markers (e.g., in this case, N400/N300 visual ERP), the disclosed method can infer how the subject relates different presented stimuli and establishes conceptual categories between them. Specifically, implementation of the disclosed method can determine how the subject associates, or discriminates, different stimuli in a sequence.

Figure 3:
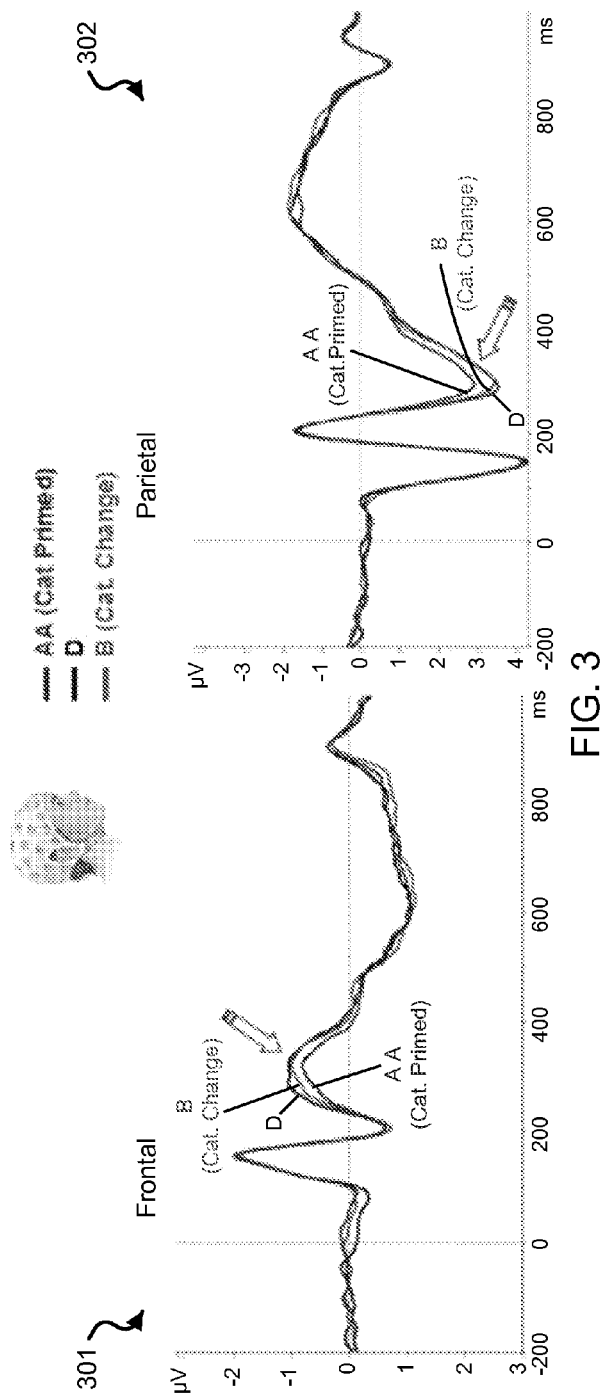
FIG. 3 shows data plots providing exemplary results from a group statistical analysis showing brain patterns of discrimination between conceptual category changes using visual stimuli.

FIG. 3 shows data plots providing exemplary results from a group statistical analysis showing brain patterns of discrimination between conceptual category changes using visual stimuli, e.g., such as the visual stimuli presentation of FIG. 2. In FIG. 3, plot 301 and plot 302 depict brain waveforms (e.g., ERPs) from a frontal and a parietal channel, respectively, (e.g., anterior and posterior anatomical localizations in the scalp, respectively) related to changes in conceptual/semantic categories.

In the example shown in FIG. 3, if, from the subject's perspective (e.g., knowledge), an image is in the same category as the previously presented one, then the brain wave response to this second image (A) will present a lower amplitude than the one to the first previous image (D)—this is a phenomena referred to as "Semantic Priming". However, if the subject then perceives the following stimulus as belonging to a different category than the one previously presented, the resulting brain wave (B) will again have a higher amplitude (e.g., a 'Semantic Violation"). The arrows in plots 301 and 302 of FIG. 3 indicate the effect of interest in the brain wave. This allows us to probe and interpret or infer his/her level of knowledge and/or understanding of the presented stimuli. The particular presentation of the stimuli (e.g., sequentially presenting stimuli in a ubiquitous manner) facilitates the priming and categorical change, which can elicit separable specific brain markers, from which data is extracted that can then be transformed, with the use of the analytical processes of the disclosed method into a sensory and/or cognitive profile, e.g., such as the Individualized Knowledge Evaluation Profile (IKEP).

I.1.6. Exemplary Processing and Guided Classification Techniques (e.g., with Context Specific Parameters)

The exemplary implementations included implementing processing techniques for correlating brain signals and cognitive states of an individual subject using a framework of classification methods that use the acquired physiological signals (e.g., neural signals from the EEG recordings) of an individual subject to provide an information set, e.g., including statistical information, about the conceptual knowledge (e.g., sensory and/or cognitive performance) and/or state of awareness of the subject. These exemplary processing techniques can also be applied to perform group analysis to identify conceptual knowledge, not just on a group, but also on a subject-by-subject basis. Providing this group analysis can be beneficial for identifying how an individual categorizes information, e.g., explicitly identify or exploit individual differences.

For example, the disclosed method can be used to characterize a subject's familiarity with a topic by deliberately providing sequences of stimuli that are sometimes contextually congruent, and sometimes contextually incongruent with respect to the specific knowledge to be probed. Based upon the subject's measured and analyzed brain response, the method can develop a "degree of familiarity" outcome to a human operator that can be expressed in a particular sensory and/or cognitive profile category (e.g., such as the Individual Knowledge Evaluation Profile) or to another process of the disclosed technology that integrates the outcome (information set) to a Brain-Machine Interface (BMI) to provide subsequent feedback to the individual.

The exemplary implementations of the disclosed processing and guided classification techniques using the visual stimuli paradigm, as described below, provide examples using the same data sets as described in the previous sections that illustrate a conceptual knowledge evaluation on a subject-by-subject basis.

For example, a description of the independent variables used in the exemplary visual data set include:
Subject number s, between 1 and 28
Channel number e, between 1 and 31
Condition c, between 1 and 2 (1="AA" for no category change, 2="B" for category change)
Trial number k, between 1 and 120
Time point of interest t within interval, between 1 and T.
For example, let the interval be [352 ms, 452 ms]. The sampling rate was 250 Hz. Then, $T=(0.452-0.352)*250=25$ Thus $y[s,e,c,k,t]$ is a real number representing an EEG voltage. For any subject, we fix s to be a constant. For the purpose of the exemplary analyses in this section, we also fix an electrode location e to be a constant. As such, the starting point for further analysis in this section is $y[c,k,t]$, a real number representing an EEG voltage.

I.1.6.1. Supervised Classifier with Training Data

The example uses a supervised classifier in exploring how individuals, themselves, organize and classify different items, e.g., ideas or concepts. Operating on completely conscious and aware individuals, the supervised classifier is first "trained on" the individual, accounting for any natural variability specific to him/her. This training is performed by first providing the subject with a set of categorically congruent (AA) and incongruent (B) stimulus groups, as explained above. These stimulus groups are carefully constructed so that they are unambiguously belong to either AA or B for all participants.

Once the classifier has been sufficiently trained, a new set of un-labeled stimulus groups are presented. These stimuli represent inputs that might elicit different brain categorizations, depending upon the way in which each subject's brain categorizes information. Each individual has the possibility to deem these groups either congruent or incongruent based on a large variety of factors, e.g., ranging from education level, ethnic background, preferences, creativity, etc. It is this very rich space of variability that can be explored and quantified using the disclosed method, e.g., providing deep insight into how an individual's brain categorizes information.

Exemplary Implementation Procedure of Supervised Classifier

To develop some features of interest for classification, we fix a condition "c" and a time point "t" to calculate the mean and standard deviation of y[c,k,t], over all trials "k". An exemplary method for generation of the average over trials, for a specific time point "t", is shown below. For example, this is analogous to how an event-related potential plot is generated, except this is not averaged over subjects—it is specific to an individual subject.

Figure 4:
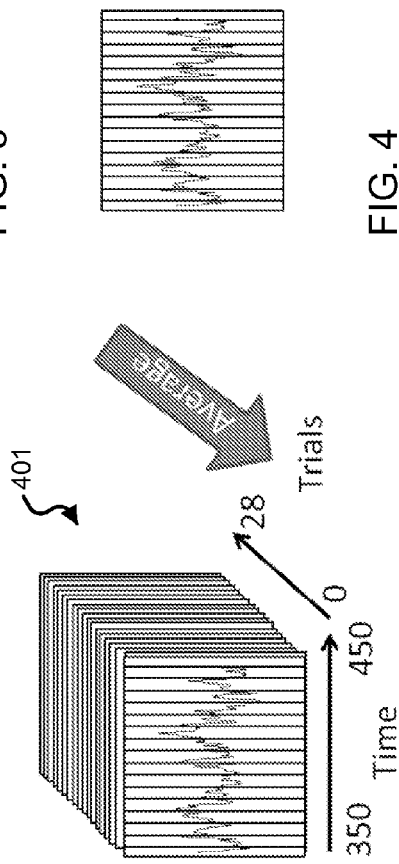
FIG. 4 shows a three dimensional plot showing EEG data on one axis representing the time window of 350 ms to 450 ms collected across multiple trials using visual stimuli.

FIG. 4 shows a three dimensional plot 401 showing EEG data on one axis representing the time window of 350 ms to 450 ms collected across multiple trials, shown in a perpendicular axis. The EEG for time point y[c,k,t] is averaged over all trials k to produce a y[c,t] average voltage for condition c at time point t within the 350 ms to 450 ms interval.

An analogous calculation is implemented to determine the standard deviation of y[c,k,t] over trials k, for a fixed c and t. For two individual channels (e.g., FP1 (channel 1) and FP2 (channel 2)), it is shown in FIGS. 5A and 5B how the most basic features of mean and variance co-vary with condition "AA" as compared to condition "B". For example, each blue and green circle represents an "average, std" feature for a specific time point "c". Blue represents condition "AA" and green represents condition "B".

FIG. 5A shows a feature plot showing the means and standard deviations of an individual subject (e.g., subject 10) from the FP1 (channel 1) electrode under two different stimulus conditions, "AA" and "B". FIG. 5B shows a feature plot showing the means and standard deviations of the individual subject (e.g., subject 10) from the FP2 (channel 2) electrode under the two exemplary different stimulus conditions, "AA" and "B". As shown in the plots of FIGS. 5A and 5B, the features have pronounced clustering which can lead to classification methods with high accuracy. For example, the accuracy with 5-fold cross-validation was 100% for both channel FP1s and FP2.

For example, it is noted that these features cluster in disjoint groups for the different conditions. For example, a support vector machine with Gaussian kernel was implemented in the Matlab statistical toolbox, using the aforementioned exemplary features in different conditions as inputs. A classification percentage was calculated using 5 fold cross-validation, for example:

Split dataset into 1/5-test, and 4/5 to train,
Rotate the test set until you test over all data,
Average your classification.

Exemplary Accuracy Control for the Classifier

In some of the figures described below, exemplary summary statistics of the performance of the support vector machine are shown, e.g., across multiple subjects and channels. In each figure, the x-axis shows different channels, and the y-axis pertains to box plots for that channel, varied across the different subjects. The exemplary classification procedures used the exemplary acquired neural data from individual subjects, e.g., in which the analyzed data is represented in the exemplary summary statistics of the performance, across multiple subject and multiple channels. In each figure, each box-plot represents a five-number summary of the data points. For example, the bottom and top of the box are always the 25th and 75th percentile (the lower and upper quartiles, respectively); the band near the middle of the box is always the 50th percentile (the median); the "whiskers" represent the one standard deviation below and above the mean of the data; and the red "+" marks represent outliers. Below each box plot is a sample table providing the median accuracy.

FIG. 6 shows a plot and corresponding table depicting the performance of the subject-supervised classifier for the visual stimulus paradigm in an exemplary implementation. For each individual channel (e.g., column of the plot), summary statistic information is provided about how the classifier performed for each subject. The box plot of FIG. 6 shows exemplary results representing the classifier accuracy after five-fold cross validation, per electrode position. The table of FIG. 6 lists median accuracy across subjects, when using the exemplary FP1, FP2, P7, or P8 electrodes.

It is noted, for example, that frontal electrodes FP1 and FP2, e.g., which can be used in many applications, demonstrate extremely high classification accuracy, and this is with the simplest possible features and a kernel from MATLAB. In other examples, more sophisticated approaches can provide even higher classification accuracies, across a larger range of subjects.

Exemplary Cognitive and/or Sensory Profile: Individual Knowledge Evaluation Profile (IKEP)

Figure 7:
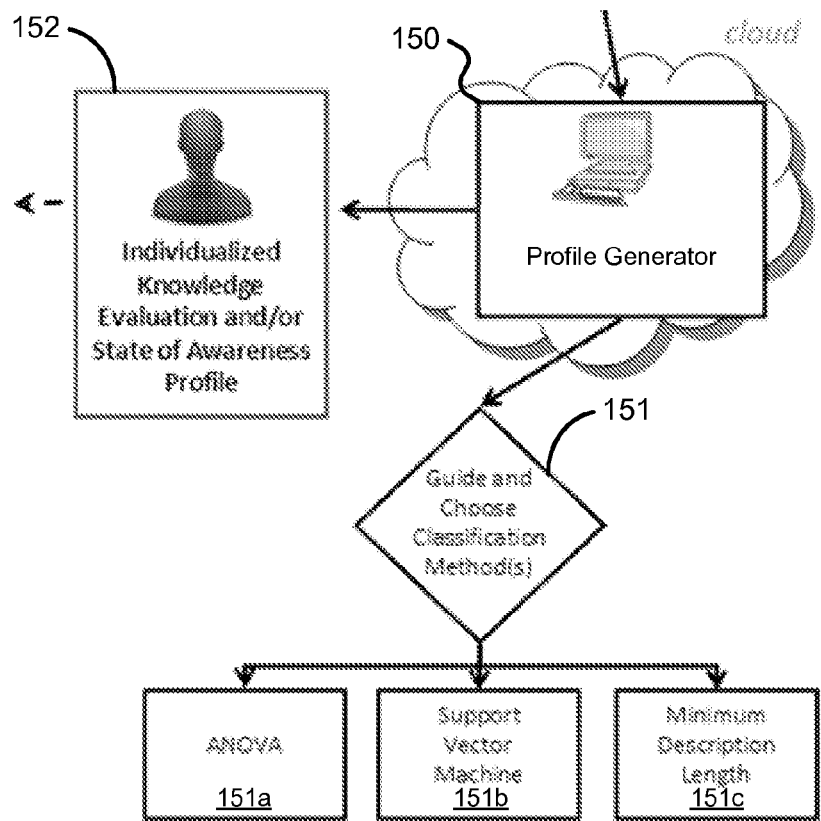
FIG. 7 shows an illustrative diagram depicting an exemplary implementation of the guided classification algorithms and their subsequent summary statistics to provide an individualized knowledge and/or awareness profile.

After providing stimuli to the subject, acquiring physiological data from the subject, and determining statistical information, as described above, the next step in the exemplary technique includes creating a profile of individual knowledge and/or of state of awareness. FIG. 7 shows an illustrative diagram depicting an exemplary implementation of the guided classification algorithms and their subsequent summary statistics to provide an individualized knowledge and/or awareness profile. For example, the exemplary knowledge evaluation and/or state of awareness profile can provide concise summary information about the user's brain response to specific stimuli.

In this first example described, the individual profile is calculated for subject 10 (as in the previous examples) within the context of "knowledge evaluation" with a supervised classifier. Specifically, for example, the features for group B (green circles) and group AA (blue circles), as shown in FIGS. 5A and 5B, are identified.

Figure 8:
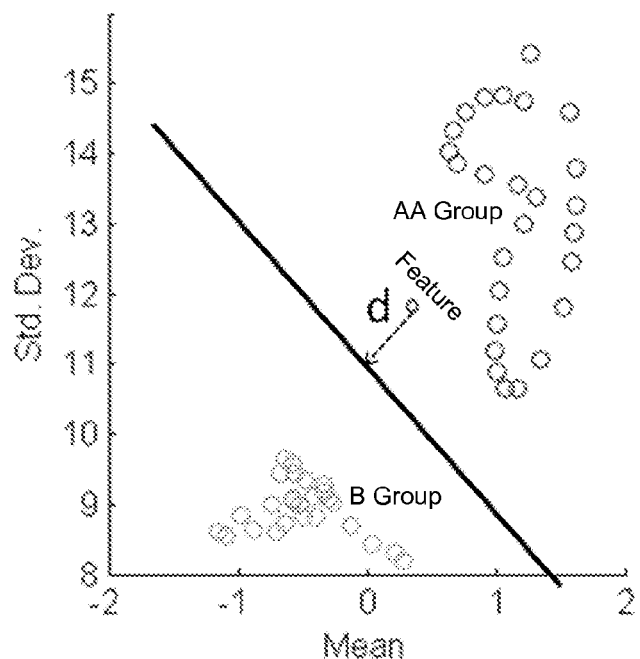
FIG. 8 shows exemplary features for the supervised classifier pertaining to an exemplary electrode channel from an exemplary subject.

FIG. 8 shows exemplary features for the supervised classifier pertaining to the exemplary channel FP2 from subject 10. A supporting hyperplane (e.g., black bold line) serves as the decision boundary. Any feature to be tested (e.g., the red circle in FIG. 8) will be classified as blue (in this case, AA) if on one side of the boundary, and it will be classified as green (in this case B) for the other. The distance "d" to the boundary can serve as a proxy to provide statistical confidence in the classification. The larger the distance is to the boundary, the more confident we are in the classification.

When testing a subject, these features are constructed. If the feature of interest (in this case, the red circle) lies on one side of the decision boundary, we declare "AA", and otherwise we declare "B". Along with a hard decision, also specified is "soft" information that suggests how confident we are in our declaration. The shortest distance between the red point and any point on the decision boundary can serve as the input to a function that specifies the IKEP. More specifically, for example, we can declare, Awareness/Knowledge Probability=$(2-e^{-d})/2$.

For example, if the distance to the boundary is 0, then the discrimination probability is ½, namely chance (e.g., the subject does not have a reliable knowledge of discriminating features between the two tested conditions, or in other words, the subject cannot discriminate items between one and the other). On the other hand, for example, if the distance to the boundary is very large, then the knowledge probability tends to 1, as expected (e.g., the subject knows each of the presented categories and how to distinguish them). As such, the exemplary statistical signal processing framework can additionally provide soft decisions, for example: $P_{sc}$=P(same category)=0.8, $P_{dc}$=P(different category)=0.2).

Figure 9:
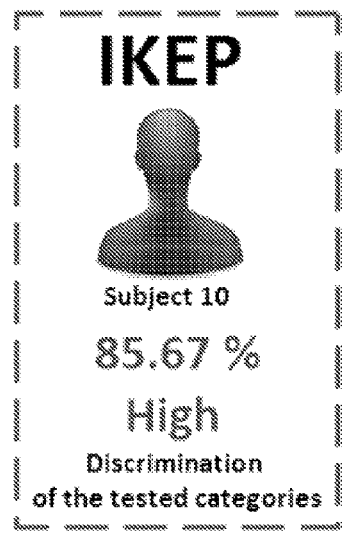
FIG. 9 shows a diagram of an example Individual Knowledge Evaluation Profile (IKEP) for the subject.

So for this example, using the same visual presentation data set as described in the previously, the exemplary IKEP can be determined as follows. Using the exemplary subject (subject 10) as in FIG. 8, suppose that we trained the classifier with the blue and green labels, and now the features for the red dot are obtained and we would like to classify this as "AA" or "B". Note that the feature for red circle is the ordered pair (e.g., 0.75,12). The closest point to the boundary is (0,11). As such, in this example, the distance between these two points is 1.25, and the subsequent IKEP for this subject (e.g., subject 10) is $(2-e^{-1.25})/2$=85.67%. FIG. 9 shows a diagram of this exemplary quantitative data for the Individual Knowledge Evaluation Profile for the exemplary subject 10.

I.1.6.2. Exemplary Unsupervised Classifier with Likelihood Ratio Tests

In examples using the "unsupervised" classifier, the technique does not use any training data to train the classifier. Rather, the classifier takes in a batch of data and then specifies a decision about the likelihood of the brain categorizing information from different stimuli in the same manner, or differently. Here, we deliberately provide a subject with a stimulus that has a known response, e.g., assuming he/she is aware.

Exemplary Implementation Procedure of Unsupervised Classifier

In this example, we first average (y[c,k,t]: k=1, . . . , K) over k to create y[c,t]. The core hypothesis to test is as follows:

H0 (null): the statistics of y[1,t] and of y[2,t] (pertaining to AA and B) are the same.

H1 (alternate): the statistics of y[1,t] and of y[2,t] (pertaining to AA and B) are not the same.

For the exemplary stimulus paradigms, it is assumed that y[1,t]−y[2,t] is Gaussian. Thus under the null hypothesis, this difference has 0 mean and unknown variance. Under the alternate hypothesis, the difference has a non-zero mean and unknown variance (not necessarily the same variance as under H0).

For example, because the variance under H0 and the mean, variance under H1 are unknown, this is a composite hypothesis testing problem, e.g., there are many distributions under each hypothesis.

The exemplary implementations included implementing a group of unsupervised classifiers pertaining to composite hypothesis testing that are theoretically sound in different manners, with different assumptions. First a test statistic is developed, which is a function of the observed data. From this test statistic, a p-value is calculated, or estimated, which is compared to a threshold, e.g., 0.05. In this example, if it exceeds 0.05, the null hypothesis is accepted; otherwise, the null hypothesis is rejected.

Test Statistic. In general, collected are the differences (d[t]=y[1,t]−y[2,t]: t=1:T) and developed is a test statistic u=g(d), which is a function of the observed data and is larger under the alternate hypothesis than under the null hypothesis. Examples of the types of test statistics that can be constructed are as follows:

T.A: a log likelihood ratio with normalized maximum likelihood (NML) estimates of P0 and P1. For example, we model the distribution under P0 (0 mean, unknown variance) and P1 (nonzero mean, unknown variance). The normalized maximum likelihood procedure creates one statistical law pertaining to each hypothesis that performs as well as possible in worst-case with respect to all possible distributions under one of the composite hypotheses. For example, under H0, the mean is unknown and so it combines statistical laws of all normal distributions of 0 mean and unknown variance, to create one statistical law that is as predictive as possible for any distribution in that class. Analogously an estimate is developed for H1, where means and variances are used. The test statistics g(d) is given by $g(d)=2cS_{27}(v)$, where $$v = \frac{\sqrt{28}\,\bar{d}}{s} \text{ and } c = \frac{\sqrt{28}\,|\bar{d}|}{s}.$$

T.B: standard statistical methods, such as an F-score for an ANOVA, based upon estimated means and variances.

P-value. After calculating the test statistic, calculated is the likelihood of observing a test statistic that is at least as extreme as what was observed, under the null hypothesis. Because the null hypothesis has an unknown variance, this is a composite hypothesis testing problem and there is not one specific natural way to calculate a p-value. We develop multiple ways to estimate a p-value:

P.A: Perform a parametric procedure to evaluate the probability expression using an estimate of P0, assuming a Normal distribution with variance estimated from data:

P.A.1: If the distribution of the test statistic, g(d) under H0 is known in closed form (e.g., for t, Z, F, ANOVA tests), then we can directly calculate or use a lookup table in Matlab.

Figure 10:
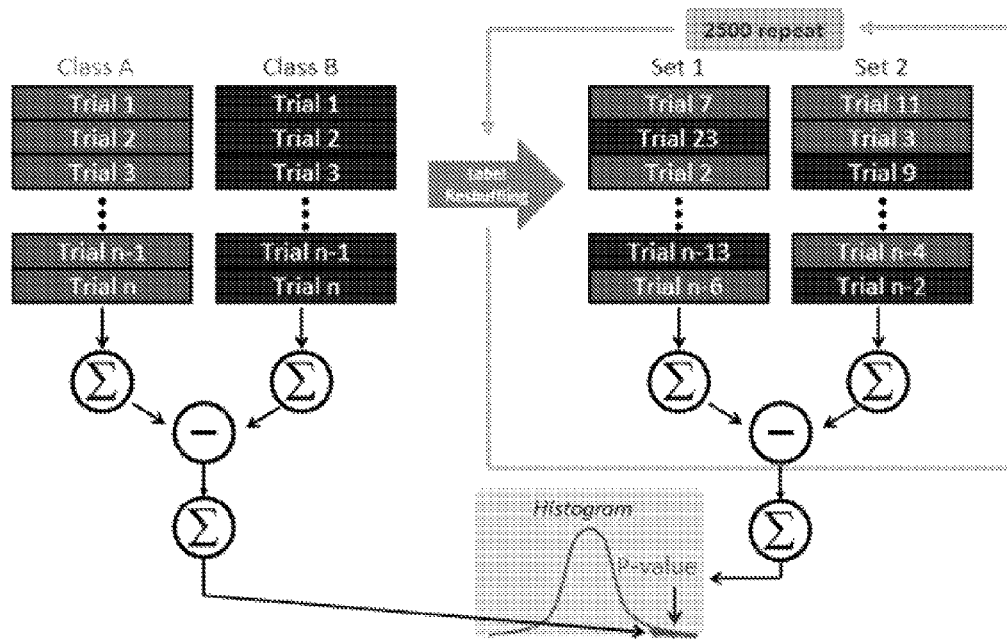
FIG. 10 shows a diagram illustrating a nonparametric procedure for estimating p-values for an exemplary hypothesis test pertaining to specify whether or not data from class A and data from class B come from the same statistical distribution.

P.A.2: If a more sophisticated test statistic (e.g., such as the normalized likelihood ratio) is used, then we implement a Monte Carlo procedure to estimate the probability. Generate a large number of independent, identically distributed samples d[1] . . . d[N] that are drawn under a Normal distribution with 0 mean and variance estimated from the data. Count the fraction of time that g(d[i])>exceeds the test statistic P.B: Perform non-parametric bootstrap procedure. Generate N iid samples d[1] . . . d[N] that are random permutations of y'; so that "in some sense", g(d[i]) is drawn according to g(d) under H0. Count the fraction of time that g(d[i])>t. FIG. 10 illustrates how the non-parametric statistical test is performed when we have two data sets (each with n trials) for two experimental conditions. (1) Collect n trials of the two experimental conditions (A and B) in a single set. (2) Randomly draw as many trials (n trials) from this 'combined' data set as there were trials in condition A and place those trials into subset 1. Then place the remaining trials (n trials) in subset 2. This procedure can be called by a random partition. (3) Calculate the test statistics on this random partition. To calculate the test statistics, the waveforms are averaged across all trials for subsets 1 and 2 during the time of interest, respectively. The average waveform of subset 1 is subtracted from the average waveform of subset 2, and then calculate the test statistics as the summation of all the differences. (4) Repeat the steps 2 and 3, e.g., a large number of times, and construct a histogram of the test statistics. (5) From the test statistic that is actually observed from our original data sets (without random permutation) and the histogram in step 4, calculate the proportion of the random partitions that resulted in a larger test statistic than the observed one. This proportion is called p-value.

FIG. 10 shows a diagram illustrating a nonparametric procedure for estimating p-values for the hypothesis test pertaining to specify whether or not data from class A and data from class B come from the same statistical distribution. Trials of class A and B are randomly permuted to generate test statistics that are drawn from the null hypothesis. From this, a histogram is formed for which the p-value evaluation can be performed.

For example, once a p-value is calculated, if it is below 0.05, then the null hypothesis is rejected; otherwise, it is accepted. In the exemplary implementations, because all the subjects were aware and the exemplary stimuli that was presented were clearly contextually incongruent, congruent, or congruent repeat under those conditions, the null hypothesis should be rejected on most subjects. The performance of this exemplary approach is characterized below, e.g., by quantifying the number of subjects and electrodes for which the null hypothesis is rejected.

Exemplary Results

Figures 11, 12:
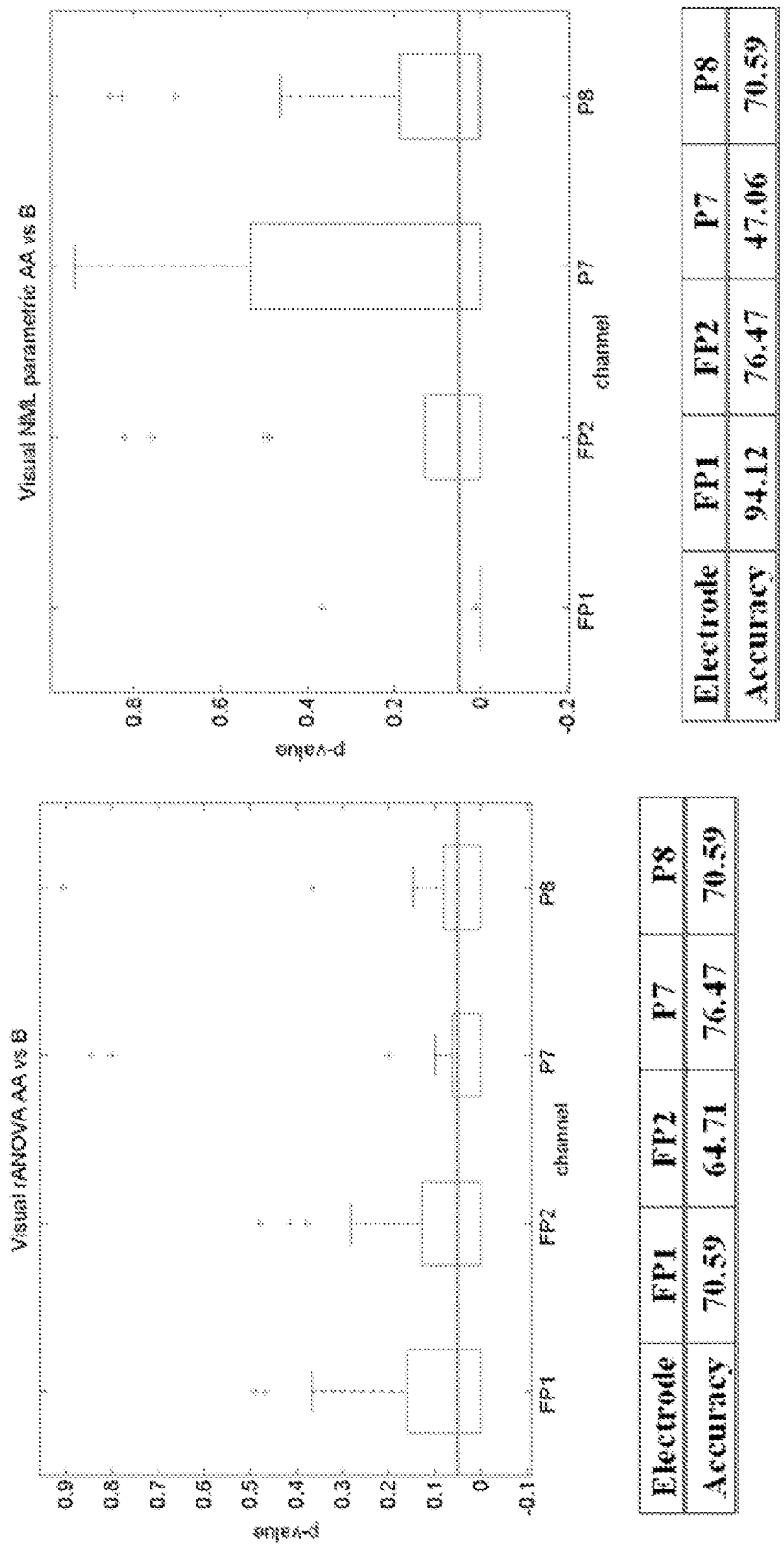
FIG. 11 shows a data plot and corresponding data table for an exemplary rANOVA analysis of AA vs B using visual stimuli.
FIG. 12 shows a data plot and corresponding data table for an exemplary NML parametric analysis of AA vs B using visual stimuli.
Figure 13:
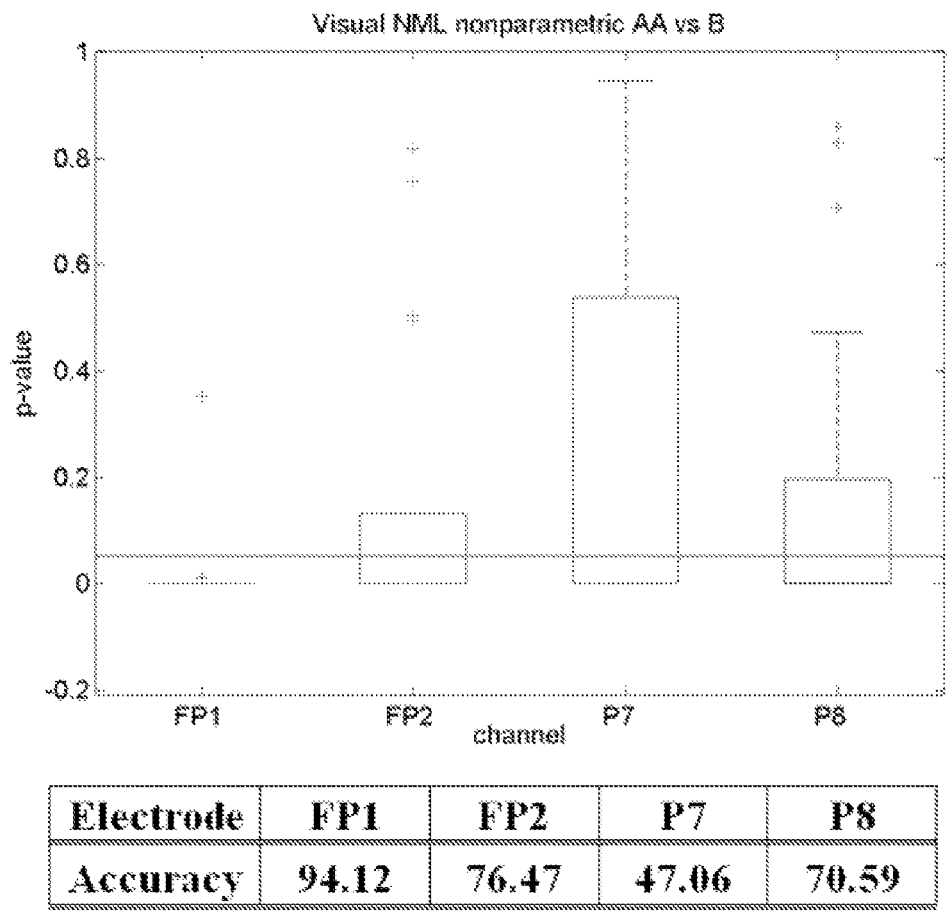
FIG. 13 shows a data plot and corresponding data table for an exemplary NML nonparametric analysis of AA vs B using visual stimuli.

For each of the exemplary stimulus paradigms presented to subjects, the exemplary performance of the different test statistics and methods of calculating p-values are shown in FIGS. 11-13. FIG. 11 shows a data plot and corresponding data table for an exemplary rANOVA analysis of AA vs B using visual stimuli. FIG. 12 shows a data plot and corresponding data table for an exemplary NML parametric analysis of AA vs B using visual stimuli. FIG. 13 shows a data plot and corresponding data table for an exemplary NML nonparametric analysis of AA vs B using visual stimuli.

In FIGS. 11-13, a box-plot of the p-values of the classifier is provided for specific electrode locations of interest, e.g., FP1, FP2, P7, and P8. The box plot provides the median (red line), standard deviation (width), and outlier information. The green horizontal line across each data plot corresponds to the threshold of the p-value being 0.05. All subjects with p-values below are thus classified correctly, and those above are classified incorrectly. Along with each box-plot, there is also a succinct, corresponding table describing the overall fraction of correct classifications (with p-value threshold at 0.05), over all subjects.

In FIGS. 11-13, the nomenclature is as follows:
"AA vs B" denotes that $d[t]=y[1,t]-y[2,t]$: $t=1:T$, where $y[1,t]$ pertains to the AA visual stimulus and $y[2,t]$ pertains to the B visual stimulus.
"NML" is succinct for the normalized maximum likelihood method of calculating a test statistic, section T.A.
"parametric" represents the parametric method of estimating a p-value, described in section P.A by performing Monte-Carlo estimation of the p-value, where the input to the test-statistic was drawn according to a Normal distribution with mean and variance estimated from the samples.
"nonparametric" represents the non-parametric method, P.B, of estimating a p-value
"rANOVA" represents a test statistic and p-value calculation paradigm using a standard repeated measures ANOVA methodology, method P.A.1.

These exemplary analyses were performed individually and then averaged for a group dataset that included 17 subjects. For example, it is noted that, remarkably, for channels FP1 and FP2 (which are frontal and don't require gelling of hair, and therefore can be utilized in a preferred embodiment in some applications), these classification methods have accuracy uniformly in the 80-100% range. These exemplary results suggests that a system with only frontal electrodes can elicit high performance. The disclosed method does not need to always include acquiring frontal activity.

Exemplary Cognitive and/or Sensory Profile: Group Knowledge Evaluation Profile (GKEP) and Individual Knowledge Evaluation Profile (IKEP)

Using this last example of an unsupervised classifier embodiment, and selecting the frontal electrode FP1 to illustrate this profile, the final product of the exemplary implementation of the method can be in the form of a Group Knowledge Evaluation Profile (GKEP) or in the form of an Individual Knowledge Evaluation Profile (IKEP).

Figure 14:
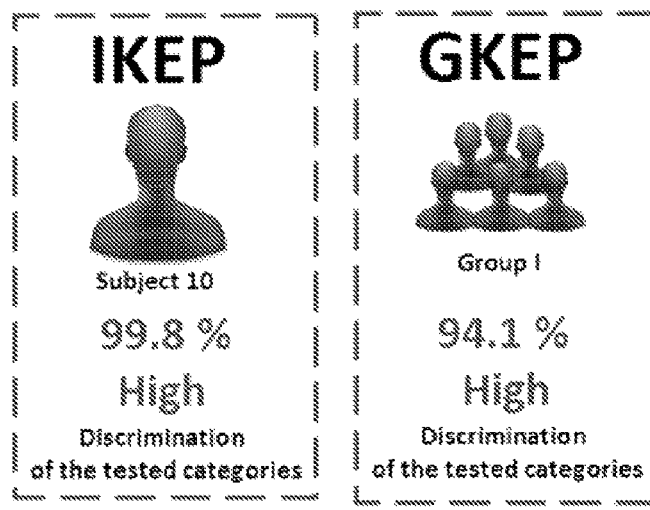
FIG. 14 shows diagrams of examples of Individual Knowledge Evaluation Profile for an individual subject and Group Knowledge Evaluation Profile for a group based subject.

For example, we identify the p-value for any subject and perform 100%-p-value, using the nonparametric likelihood ratio test (as shown in FIG. 13) as a measure of discrimination in tested categories. In the individual case, for the exemplary subject 10, this was 99.8%. At the group level, the median level was 94.1%. These exemplary results are shown in FIG. 14. FIG. 14 shows diagrams of examples of Individual Knowledge Evaluation Profile for an individual subject and Group Knowledge Evaluation Profile for a group based subject.

I.2. N400 with an Auditory Stimuli Paradigm

I.2.1. Exemplary Stimuli

In another example implementation, examined were the neural responses to linguistic stimuli, more precisely modulatory responses to contextual congruencies and incongruences within the English language. For example, Adobe Soundbooth CS5 was used to record a list of twenty words from four speakers (e.g., two male, two female) each for a total of eighty stimulus exemplars. Each speaker recorded the following exemplary words: Action, Birthday, Camera, Candles, Cheese, Crash, Danger, Death, Drink, Drive, Fight, Food, Gifts, Happy, Lights, Murder, Poison, Shoot, Smile, Yummy. Also for example, Adobe Soundbooth CS5 was used to control within and across stimuli using the following steps: (1) normalize each stimulus (e.g., Processed>Normalize), (2) equalize each stimulus (e.g., Processed>Equalize volume levels), (3) equalize volume levels across all stimulus files (e.g., Select all files>Go to Tasks>dragged files to Files to Match>Match to File>selected first file in list). For example, the duration of the stimulus pool ranged from 380 ms to 834 ms, e.g., with an average of 615.675 ms. These exemplary words were then used to construct 90 distinct three-word strings.

These exemplary ninety strings were divided equally into three conditions: congruent (30 strings), incongruent (30), and congruent with repetition (30). In each of the strings, the first two words created a context. The third word either matched (congruent) or did not match (incongruent) the context set by the previous two words. For example, in the congruent with repetition condition, the third word matched the set context by repeating the second word of the string. Moreover, because there were four speakers, for example, there were a total of 360 string exemplars. Within strings, each had a consistent speaker for each of the three words. However, the speaker and gender of the speaker could change between strings. Moreover, for example, only a subset of these strings was used for the final event-related potential and statistical analyses. This subset was controlled for word appearance and frequency across conditions. All other strings were not used for the analyses and instead utilized as "fillers" in order to create a sense of variety for subjects.

Two exemplary methods were implemented to create a fixation dot and a blue square stimulus. For the fixation dot, for example, a computer implemented process (e.g., programmed using a MATLAB script) was used to create a black background image (e.g., red gun equal to 0; green gun equal to 0; blue gun equal to 0) with a height and width of 350 pixels. Then, the exemplary script ran a nested for-loop using the standard equation of a circle to alter pixels within a seven pixels length radius to red by changing the image's red gun to 255, the green gun to 0, and the blue gun to 0. For example, for the blue square stimulus, imaging software (e.g., Adobe Photoshop) was used to create a 157×157 pixel sized image, e.g., whose red gun was equal 0, green was equal 0, and blue was equal 255.

I.2.2. Subject Preparation for EEG Recording

To prepare the exemplary subjects for EEG recording, each subject was seated in a chair in a recording chamber to begin an EEG capping process. For example, this process involved placing a traditional EEG cap on the subject's head and securing it with an elastic chin strap. In some examples, either a 56 cm or a 58 cm diameter cap was used, based on the estimated size of the subject's head. Next, Signa electrode gel (e.g., from Parker Laboratories) was injected using a curved, plastic syringe under each of the cap's electrodes to create a conductive bridge between the electrode itself and the subject's scalp. Also, for example, wooden Q-tips were used to massage the gel in order to build a stronger conductance by lowering the impedance. For example, use of this technique lowered the impedance levels to <5 k$\Omega$ for each electrode, e.g., including the ground and reference. Before starting the exemplary implementation using EEG recordings, subjects were seated in front of the presentation monitor and audio speaker and asked to just maintain visual fixation on a red, central fixation dot throughout the duration of the experiment and restrict their motor movements as much as possible to prevent motion artifacts in the neurophysiological data. In some examples, these points were emphasized by showing the subject the online recording of their raw brain waves, e.g., demonstrating to them what happens to the data when they frequently blink and/or clench their jaw. Afterwards, the recording room's lights were then dimmed, and the stimulation process and EEG recordings began. Measures were taken to completely black out the recording room's windows and seal its cracks to prevent exterior light from entering.

I.2.3. Exemplary Stimuli Presentation Process

The exemplary stimulus presentation paradigm that was used in this example stimuli presentation process was programmed using Cogent 2000. The exemplary stimulus presentation was divided into two blocks based on speakers. For example, block 1 included a total of 180 strings, 90 strings of the male speaker and 90 string of the female speaker. Block 2 included another 180 strings, 90 strings of the other male speaker and 90 strings of the other female speaker. Each of the 180 strings was presented only once per presentation block. After the presentation of each word within a string, an inter-stimulus interval (ISI) of 1000 ms was given. Between each string, an inter-trial interval (ITI) of 2500 ms was given to create an obvious break between each string presentation. For example, after every six to nine strings, a blue square was presented for 2000 ms, which indicated a "mini break" in which the subject could briefly pause, rest, scratch their nose, etc.

Prior to the stimulus presentation, the process (e.g., programmed in a MATLAB script) first randomly permuted the order in which the strings would be presented, e.g., using MATLAB's randperm( ) function. Then, the process randomly determined which trials would be followed by a blue square stimulus using the exemplary randi( ) function. In addition to configuring the display, sound card, and parallel port, a log file was configured and initialized within the Cogent 2000 system. For example, this log file was used to hold information pertaining to stimulus, namely its membership to a particular string. Subsequently, both the audio and visual (e.g., fixation dot, blue square) stimuli were loaded into memory buffers. The aforementioned steps were executed prior to stimulus presentation in order to reduce computational load and increase latency precision.

The exemplary stimulus presentation process used in the exemplary implementations with auditory stimuli included a nested for-loop. For example, within the "outer" loop, a random-without-replacement chosen string was determined and the red, central fixation dot was presented 1000 ms prior to the onset of the first word/call of the string. The fixation dot was displayed throughout the entire presentation of the string and was turned off 1000 ms after the offset of the third word/call. For example, within the "inner" loop, trigger information was calculated based on the string itself and sent to the EEG recording computer. Strings were organized in such a way that their location within the exemplary MATLAB matrix would provide the necessary information for the stimulus trigger. At the end of the "inner" loop, the exemplar was presented, the parallel port was reset to zero, and the inter-trial interval was given. For example, audio stimuli were presented using an Advent Powered Partners AV570 speaker, and visual stimuli were presented using a Sony Trinitron GDM-C520 monitor.

Figure 15:
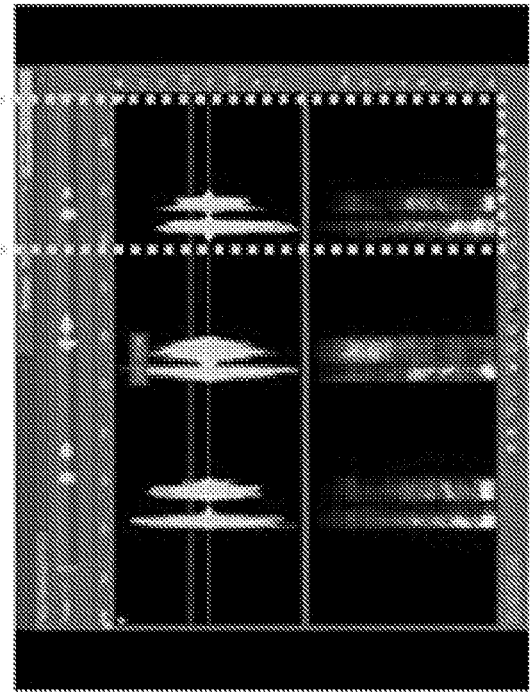
FIG. 15 shows diagrams of an exemplary sequence of presented auditory stimuli.

FIG. 15 shows diagrams of an exemplary sequence of presented auditory stimuli. The illustrative diagrams 1501 and 1502 of FIG. 15 portray audio waveforms and spectrograms of specific presented exemplars of strings of three words. For example, the exemplary sequence of presented auditory stimuli shown in diagram 1501 includes three consecutive English words including "Birthday", "Gifts", and "Happy", forming a contextually "Congruent" string. Also, for example, the exemplary sequence of presented auditory stimuli shown in diagram 1502 includes three consecutive English words including "Poison", "Danger", and "Happy", forming a contextually "Incongruent" string. In both examples shown in diagrams 1501 and 1502, the first two words establish a context, and the third is either coherent with that context congruent or Incongruent. In another sequencing example, another testing condition can also be presented, "Congruent Repetition", in which the second and third words in a string are exactly the same.

I.2.4. Exemplary Brain Waves (EEG) Recordings

In some implementations, a traditional EEG system with rigid electrodes was used to acquire brain waves. The exemplary EEG system included a BrainAmp DC 32-channel system; BrainVision Recorder; Fast n Easy 32-channel EEG recording cap size 56 cm; Fast n Easy 32-channel EEG recording cap size 58 cm; PCB Ribbon Cable for BrainCap-MR with 5 k resistors; and BrainCap MR Box 1.2.

I.2.5. Exemplary Pre-Processing Analysis Techniques

The exemplary analysis pre-processing techniques of the disclosed methods using an auditory stimuli paradigm can include techniques for processing the marker data. For example, after each recording session, the exemplary EEG recordings system produced three files: data file (.eeg), header file (.vhdr), and marker file (.vmrk). The marker files contained the event triggers for each stimulus onset. In these examples, because of output limitations within the parallel port, the exemplary Cogent 2000 log file was used to hold additional information regarding an exemplar's membership to a particular string. From there, the analysis pre-processing techniques includes a process (e.g., programmed using a MATLAB script) to integrate information from both the log file and exemplary EEG recordings system marker file and to alter the stimulus code within the marker file to represent the following information for each stimulus, e.g., the condition (congruent, incongruent, congruent with repetition), the position of the word/call ($1^{st}$, $2^{nd}$, $3^{rd}$), the gender of the speaker (in the case of English words), and the specific word/call (e.g., "happy", "birthday", "coo", "scream"). For example, a congruent English words string [birthday; gifts; happy] would be re-coded as [C1M_2; C2M_13; C3M_14]. In this example, the first digit represented condition ("C" for congruent in this example), the second digit represented position within the string (1st, 2nd, and 3rd), the third digit represented the gender of the speaker ("M" for male, "F" for female), and the digit following the underscore represented the specific word presented ("2" for birthday, "13" for gifts, and "14" for happy).

The exemplary analysis pre-processing techniques of the disclosed methods include techniques for general group statistical analysis. In the exemplary implementations described herein, a combination of MATLAB and Statsoft Statistica (version 8.0) software was used for statistical analyses. After data processing and analysis, the BrainVision Analyzer of the exemplary EEG recording system exported text files containing data values in regards to condition, subject, trial, electrode channel, peak latency, peak voltage, and mean voltage amplitude. The exported text files were loaded into a computer implemented program (e.g., a MATLAB program) to sort and organize the data in a more accessible format. Specifically, for example, the exemplary computer implemented program allows one to more easily select data by column, e.g., using MATLAB's variable editor. After selecting, data were copied and pasted into Statistica data spreadsheets. In some implementations, for example, repeated measures ANOVAs were performed on each spreadsheet, e.g., comparing the effect of condition, namely congruent, incongruent, and congruent with repetition for each species for both English words and rhesus macaque calls. For human subjects, for example, each spreadsheet was specific to the following: 1) experiment: English words or rhesus calls; 2) component: N400 or N800; 3) electrode channels: Cz+Pz (electrode pool), Cz+Pz+Cp1+Cp2+P3 (electrode pool), Cz+Pz+Cp1+Cp2 (electrode pool), or Pz+Cp1+Cp2 (electrode pool). For these exemplary pooled electrodes analyses, for example, two-way repeated measures (e.g., factor 1: condition; factor 2: electrode channels) ANOVAs were performed. Likewise, for NHP subjects, for example, each spreadsheet was specific to the following: 1) experiment: English words or rhesus calls; 2) component: N400 or N800; 3) electrode channels: Cz+Pz (electrode pool), Cz+Pz+P1 (electrode pool), Cz+Pz+P1+Tp3+C1 (electrode pool), O1+O2 (electrode pool). For these exemplary pooled electrode analyses, two-way repeated measures (e.g., factor 1: condition; factor 2: electrode channels) ANOVAs were performed.

In some examples, also analyzed/looked at suppression were the effects between the first and third position words/calls across conditions. For human subjects, for example, each spreadsheet was specific to the following: 1) experiment: English words or rhesus calls; 2) component: N1, P2, N400, or N800; 3) electrode channels: Cz, or Cz+Pz (electrode pool). Likewise, for NHP subjects, for example, each spreadsheet was specific to the following: 1) experiment: English words or rhesus calls; 2) component: N1, P2, N400, or N800; 3) electrode channels: Cz, or Cz+Pz (electrode pool). For single electrode analyses, for example, two-way repeated measures (factor 1: position; factor 2: condition) ANOVAs were performed. For pooled electrodes analyses, for example, three-way repeated measures (e.g., factor 1: position; factor 2: electrode; factor 3: condition) ANOVAs were performed. For example, the subject number was used as a categorical predictor for both subject pools for both the congruency and suppression effects analyses. For example, statistical analysis of congruency comparisons (C3, I3, and CR3) reflected in the N400 ERP effect (between 352 and 452 ms) in electrodes Cz and Pz using our English words paradigm, revealed the following results: $F(2, 954)=5.5791$ and a P-value of 0.0039. For example, the post hoc Fisher Test produced the following P-values: C3 vs I3=0.008332 and CR3 vs I3=0.037043. This demonstrates that the exemplary method can be implemented to obtain statistically significant discriminations between the different congruency conditions.

Figure 16:
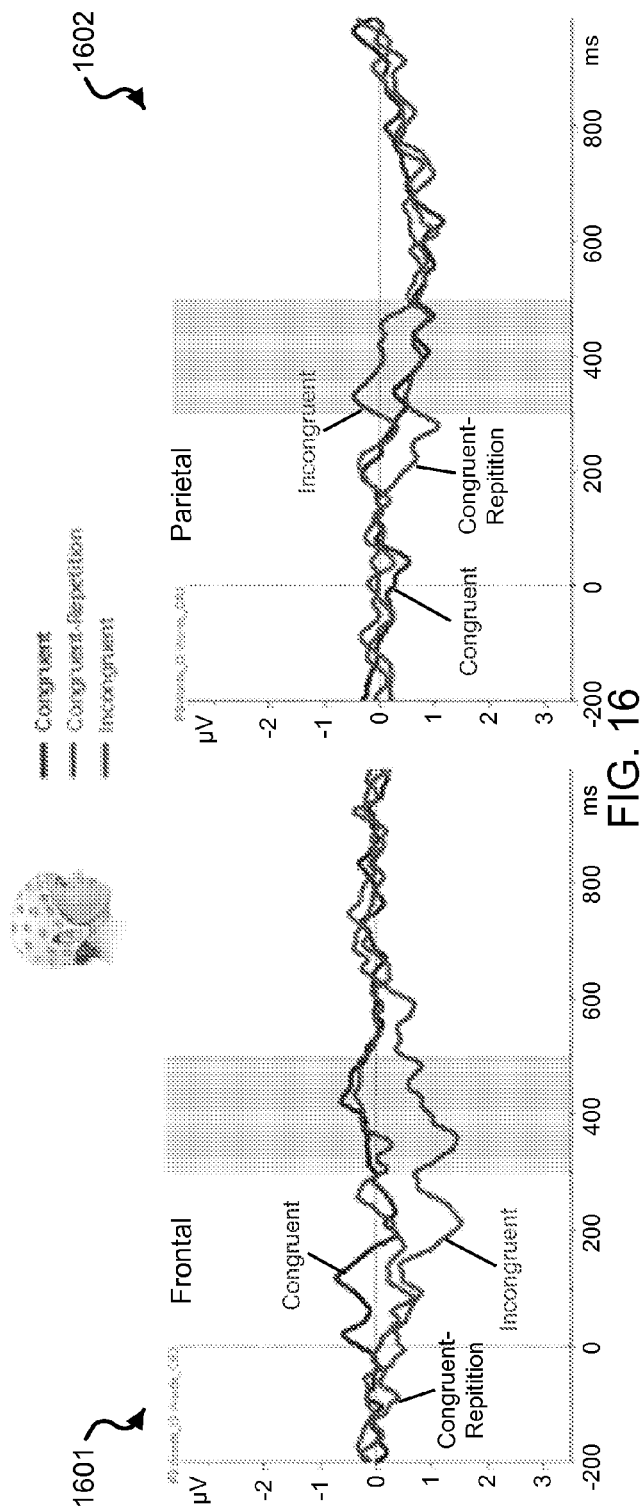
FIG. 16 shows data plots providing exemplary results from a group statistical analysis showing brain patterns of discrimination between contextual changes in auditory stimuli.

FIG. 16 shows data plots providing exemplary results from a group statistical analysis showing brain patterns of discrimination between contextual changes in auditory stimuli (e.g., using English words). In FIG. 16, plot 1601 and plot 1602 depict brain waveforms (e.g., ERPs) from a frontal and a parietal channel, respectively, (e.g., anterior and posterior anatomical localizations in the scalp, respectively) related to changes in semantic context.

In the example shown in FIG. 16, as in the case of the Visual N400, the Auditory N400 response is higher in amplitude when there is a semantic violation—in this case a violation of context in the "Incongruent" type of strings. In the exemplary implementations, we calculated the ERP to the third word of strings from each set and used the amplitude modulation of the N400 response as input data on the subsequent steps of the exemplary method, e.g., processes for analysis, guided classification algorithms, etc., to create a sensory and/or cognitive profile, e.g., including a State of Awareness Profile of the subject. The blue-shaded area(s) of the plots 1601 and 1602 indicate time interval for the effect of interest. In each plot, the red line represents the ERP for "Incongruent" strings, the blue line the ERP represents for "Congruent" strings, and the green line represents the ERP for "Congruent with Repetition" strings. This is an example of a group of awake/aware subjects, where it can be seen that the amplitude of the ERP response to contextually incongruent strings is higher than for the congruent one's. As in the previous example using the Visual N400, the described methodology is passive (e.g., the auditory stimuli are delivered by either a speaker or headphones and the subject is not required to show any overt response). The application of this exemplary implementation with the described method, based on the differential response to congruent and incongruent sequences, can evaluate the level of awareness (or non-awareness) of a given person, who is not being able to perform any kind of behavioral response, in some examples referred to as a State of Awareness Profile.

I.2.6. Exemplary Processing and Guided Classification Techniques (e.g., with Context Specific Parameters)

As in the exemplary implementations using the N400 with visual stimuli, the exemplary implementations using N400 with auditory stimuli included implementing processing techniques for correlating brain signals and cognitive states of an individual subject using a framework of classification methods that use the acquired physiological signals (e.g., neural signals from the EEG recordings) of an individual subject to provide an information set, e.g., including statistical information, about the conceptual knowledge and/or state of awareness of the subject. These exemplary processing techniques can also be applied to perform group analysis to identify conceptual knowledge, not just on a group, but also on a subject-by-subject basis, which can be beneficial for identifying how an individual categorizes information, e.g., explicitly identify or exploit individual differences.

In this example, auditory stimuli is used instead of visual stimuli, e.g., to illustrate that this methodology can be successfully applied on brain responses obtained by different sensory modalities, and in addition to illustrate an example where the final profile will be a Individual State of Awareness Profile (ISAP) instead of an IKEP. As such, in this exemplary case, the differences are exploited in how one subject integrates information from a sequence of sounds that are either contextually "Congruent" or contextually "Incongruent". For example, in order for the brain to produce a modulation of its neural response correlated to the congruency of the broadcasted auditory strings of words, the subject must not only hear each word but, moreover, understanding its meaning, establish a contextual correlation between the first two words presented and then compare that contextual correlation to the meaning of the third word to either produce a brain signal modulation consistent with a congruent or incongruent string. In other words, the subject hearing the sounds is not enough, he/she needs to be cognitively active understanding and correlating the words he/she is hearing. Using the exemplary method, this can allow, by inference from this modulation, the creation of an individual profile that reflects a probability of awareness of the tested person, e.g., without any overt behavioral response from him/her. For these described exemplary analyses below using the auditory stimuli paradigm, the same auditory N400 data set was used presented in the previous section.

This serves as a specific demonstration of our framework with noteworthy performance to obtain an "Individual State of Awareness Profile" (ISAP) from a passive (non-behaving) person. Our general methodology is not specific to this approach; rather this section shows that our framework is capable of discriminating such information in a subject-by-subject basis.

The exemplary implementations of the disclosed processing and guided classification techniques using the auditory stimuli paradigm, as described below, provide examples using the same data sets as described in the previous sections that illustrate a state of awareness sensory-cognitive profile from a passive (e.g., non-behaving) person on a subject-by-subject basis.

For example, a description of the independent variables used in the exemplary auditory data set included:

Subject number s, between 1 and 25
Channel number e, between 1 and 31
Condition c, between 1 and 3 (1="I" for incongruent, 2="C" for congruent, 3="CR" for congruent repeat)
Trial number k, between 1 and 28
Time point of interest t within interval, between 1 and T. For example, let the interval be [352 ms, 452 ms]. Sampling rate was 250 Hz. Then, T=(0.452−0.352)* 250=25

As such, y[s,e,c,k,t] is a real number representing an EEG voltage. For any subject, we fix s to be a constant. For the purpose of the exemplary analyses in this section, we also fix an electrode location e to be a constant. As such, the starting point for further analysis in this section is y[c,k,t], a real number representing an EEG voltage.

I.2.6.1. Supervised Classifier with Training Data

As previously discussed, a supervised classifier can be used to explore how individuals organize and classify different items. Operating on completely conscious and aware individuals, the supervised classifier can first be "trained on" the individual, accounting for any natural variability specific to him/her by beginning with a well-established set of incongruent (I), and congruent (C) stimulus groups as explained above in the auditory section. These would be stimulus groups that have been carefully constructed to ensure that they unambiguously belong to I, or C categories.

Exemplary Implementation Procedure of Supervised Classifier

As in the visual stimuli example, to develop features of interest for classification, a condition "c" and a time point "t" are fixed to calculate the mean and standard deviation of y[c,k,t], over all trials "k". For example, a method for generation of the average over trials, for a specific time point "t", is described below. For example, this can be analogous to how an event-related potential plot is generated, except this is not averaged over subjects—it is specific to an individual subject.

Figure 17:
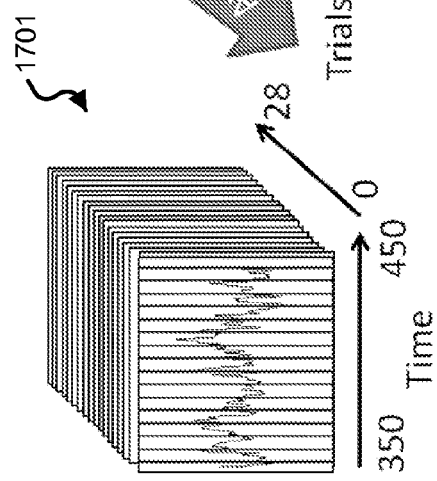
FIG. 17 shows a three dimensional plot showing EEG data on one axis representing the time window of 350 ms to 450 ms collected across multiple trials using auditory stimuli.

FIG. 17 shows a three dimensional plot 1701 showing EEG data on one axis representing the time window of 350 ms to 450 ms collected across multiple trials using auditory stimuli, the multiple trials shown in a perpendicular axis. The EEG for time point y[c,k,t] is averaged over all trials k to produce a y[c,t] average voltage for condition c at time point t within the 350 ms to 450 ms interval.

Figures 18A, 18B:
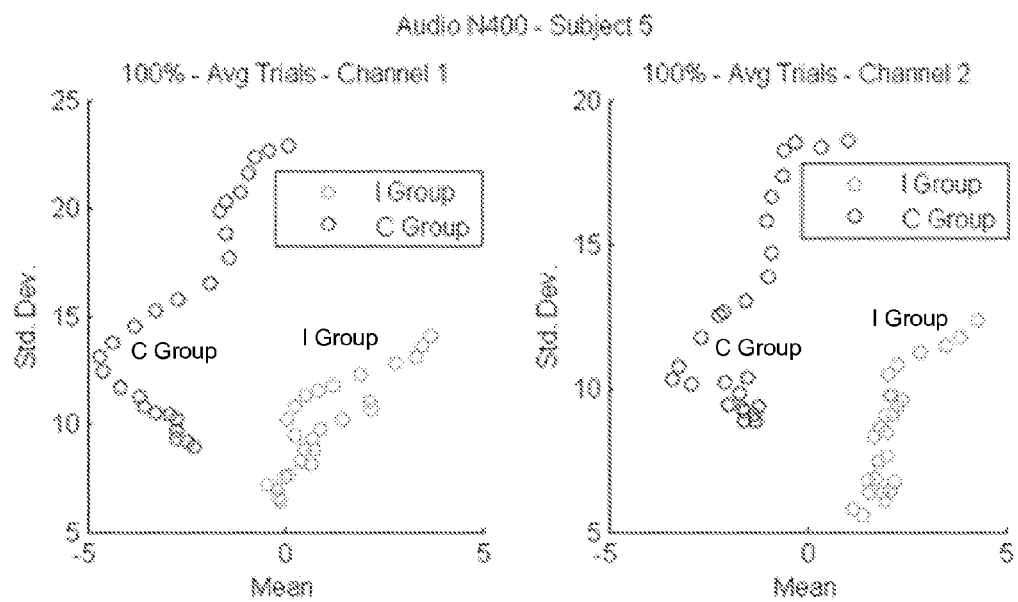
FIGS. 18A and 18B show data plots showing the means and standard deviations of an individual exemplary subject from two exemplary electrode channels under two different auditory stimulus conditions.

An analogous calculation was implemented to determine the standard deviation of y[c,k,t] over trials k, for a fixed c and t. For two individual channels (FP1 (channel 1) and FP2 (channel 2)), it is shown in FIGS. 18A and 18B how the most basic features of mean and variance co-vary with condition "C" as compared to condition "I". For example, each blue and green circle represents an "average, std" feature for a specific time point "c". Blue represents condition "C" and green represents condition "I".

FIG. 18A shows a feature plot showing the means and standard deviations of an individual subject (e.g., subject 5) from the FP1 (channel 1) electrode under two different stimulus conditions, "I" and "C". FIG. 18B shows a feature plot showing the means and standard deviations of an individual subject (e.g., subject 5) from the FP2 (channel 2) electrode under two different stimulus conditions, "I" and "C". As shown in the plots of FIGS. 18A and 18B, the features have pronounced clustering which can lead to classification methods with high accuracy. For example, the accuracy with 5-fold cross-validation was 100% for both channel FP1s and FP2.

For example, it is noted that these features cluster in disjoint groups for the different conditions. These features served as inputs to an exemplary support vector machine classification algorithm implemented on a computer system including the MATLAB statistical toolbox. For example, in the exemplary implementations, we performed 1 out of 5, five-fold cross-validation. For example, the frontal electrodes FP1 and FP2 demonstrate extremely high classification accuracy, which is noted that this was achieved in this exemplary implementation using simple features and a kernel from MATLAB. The exemplary method can be configured to extract this information at an individual subject level.

Exemplary Accuracy Control for the Classifier

In some of the figures described below, exemplary summary statistics of the performance of the support vector machine are shown, e.g., across multiple subjects and channels. In each figure, the x-axis shows different channels, and the y-axis pertains to box plots for that channel, varied across the different subjects. The exemplary classification procedures used the exemplary acquired neural data from individual subjects, e.g., in which the analyzed data is represented in the exemplary summary statistics of the performance, across multiple subject and multiple channels. In each figure, each box-plot represents a five-number summary of the data points. For example, the bottom and top of the box are always the 25th and 75th percentile (the lower and upper quartiles, respectively); the band near the middle of the box is always the 50th percentile (the median); the "whiskers" represent the one standard deviation below and above the mean of the data; and the red "+" marks represent outliers. Below each box plot is a sample table providing the median accuracy.

Figure 19:
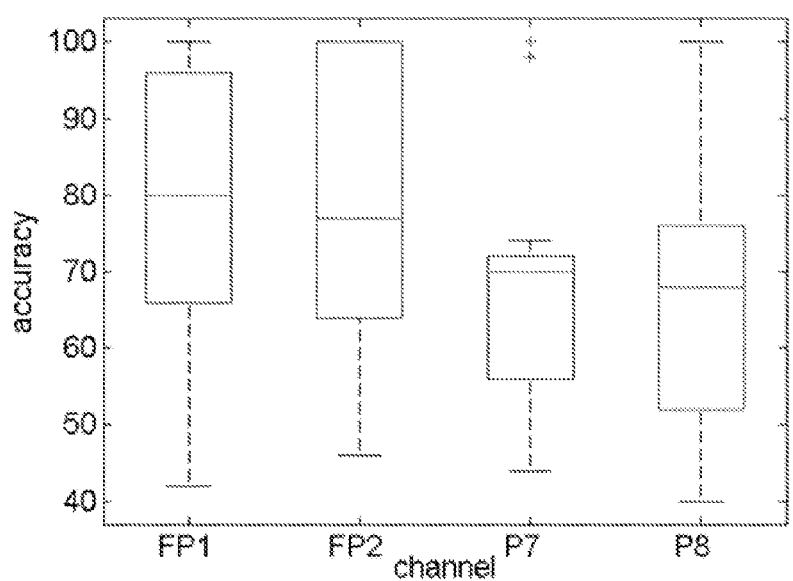
FIG. 19 shows a data plot and corresponding table depicting the exemplary performance of the subject-supervised classifier for the auditory stimulus paradigm.

FIG. 19 shows a plot and corresponding table depicting the performance of the subject-supervised classifier for the auditory stimulus paradigm in an exemplary implementation. For each individual channel (e.g., column of the plot), summary statistic information is provided about how the classifier performed for each subject. The box plot of FIG. 19 shows exemplary results representing the classifier accuracy after five-fold cross validation, per electrode position. The table of FIG. 19 lists median accuracy across subjects, when using the exemplary FP1, FP2, P7, or P8 electrodes.

It is noted, for example, that frontal electrodes FP1 and FP2, e.g., which can be used in many applications, demonstrate extremely high classification accuracy. In other examples, more sophisticated approaches can provide even higher classification accuracies, across a larger range of subjects.

Exemplary Cognitive and/or Sensory Profile: Individual State of Awareness Profile (ISAP)

Figure 20:
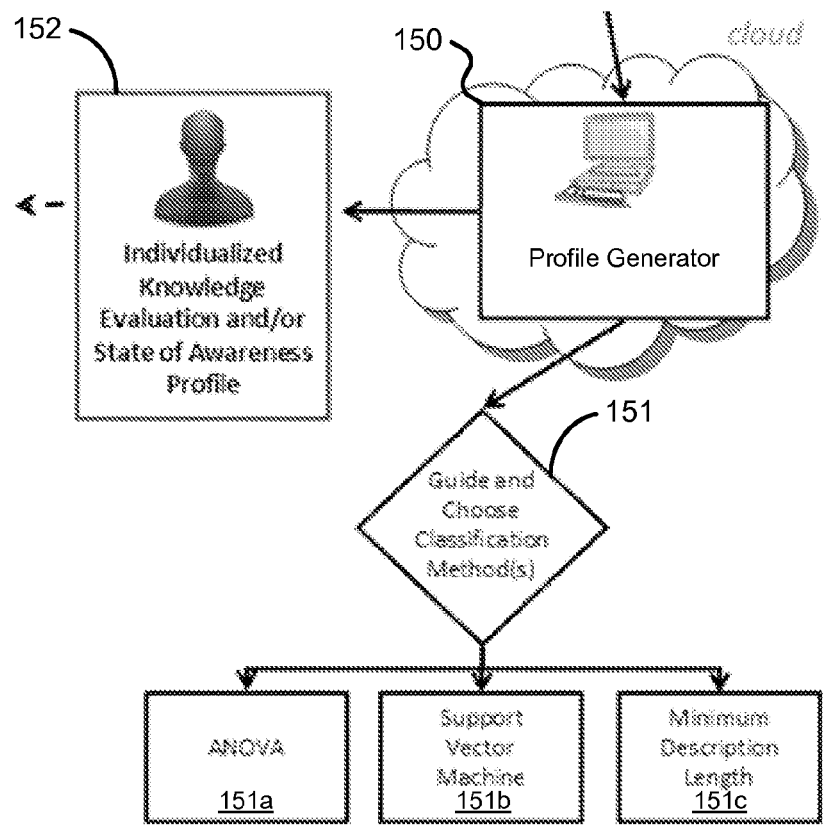
FIG. 20 shows an illustrative diagram depicting an exemplary implementation of the guided classification algorithms and their subsequent summary statistics to provide an individualized knowledge and/or awareness profile.

After providing stimuli to the subject, acquiring physiological data from the subject, and determining statistical information, as described above, the next step in the exemplary technique includes creating a profile of individual knowledge and/or of state of awareness. In this example, a ISAP is selected. FIG. 20 shows an illustrative diagram depicting an exemplary implementation of the guided classification algorithms and their subsequent summary statistics to provide as an individualized knowledge profile. For example, the exemplary knowledge evaluation and/or state of awareness profile can provide concise summary information about the user's brain response to specific stimuli.

In this example, the individual profile was calculated for the exemplary subject 5 within the context of "knowledge evaluation" with a supervised classifier. Specifically, for example, the features for group I (green circles) and group C (blue circles), as shown in FIGS. 18A and 18B, are identified.

Figure 21:
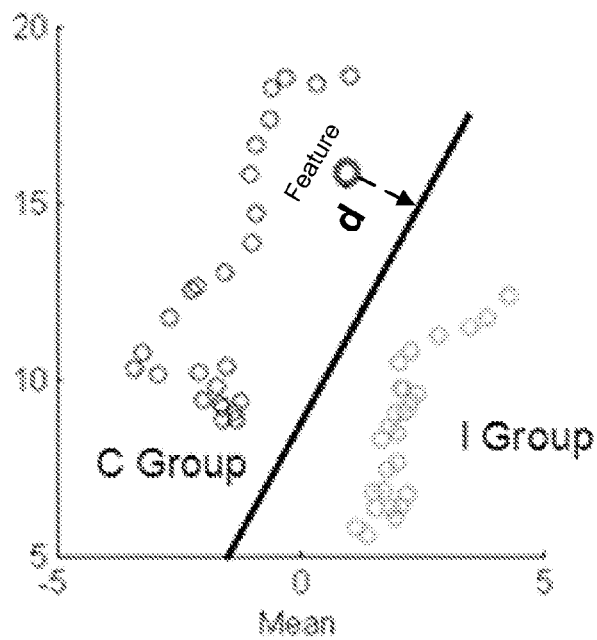
FIG. 21 shows exemplary features for the supervised classifier pertaining to an exemplary electrode channel from an exemplary subject.

FIG. 21 shows features for the supervised classifier pertaining to the exemplary channel FP2 from subject 5. A supporting hyperplane (e.g., black bold line) serves as the decision boundary. For example, any feature to be tested (e.g. the red circle in FIG. 21) will be classified as blue (in this case, C) if on one side of the boundary, and it will be classified as green (in this case I) for the other. The distance "d" to the boundary can serve as a proxy to provide statistical confidence in the classification. The larger the distance is to the boundary, the more confident the classification.

When testing a subject, these features are constructed. If the feature of interest (in this case, the red circle) lies on one side of the decision boundary, we declare "I", and otherwise we declare "C". Along with a hard decision, we also specify "soft" information that suggests how confident we are in the declaration. The shortest distance between the red point and any point on the decision boundary can serve as the input to a function that specifies the ISAP. More specifically, for example, we can declare, Awareness/Knowledge Probability=$(2-e^{-d})/2$.

For example, if the distance to the boundary is 0, then the discrimination probability is ½, namely chance (e.g., the subject does not have a reliable knowledge of discriminating features between the two tested conditions, or in other words, the subject cannot discriminate items between one and the other). On the other hand, for example, if the distance to the boundary is very large, then the knowledge probability tends to 1, as expected (e.g., the subject knows each of the presented categories and how to distinguish them). As such, the exemplary statistical signal processing framework can additionally provide soft decisions, for example: $P_{sc}$=P(same category)=0.8, $P_{dc}$=P(different category)=0.2).

Figure 22:
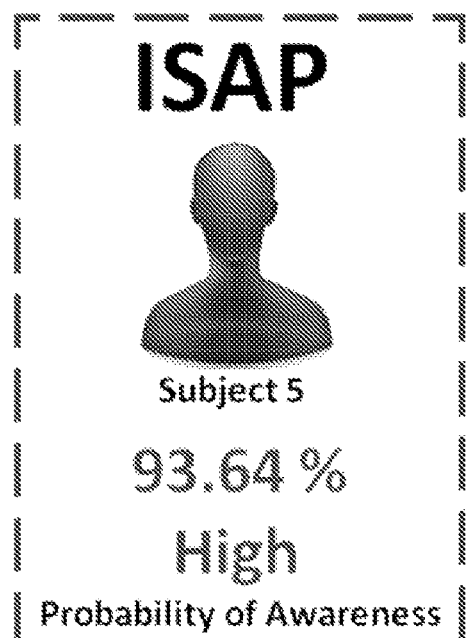
FIG. 22 shows a diagram of an example Individual State of Awareness Profile (ISAP) for the subject.

So for this example, using the same auditory presentation data set as described in the previously, the exemplary ISAP can be determined as follows. Using the exemplary subject (subject 5) as in FIG. 21, suppose that we trained the classifier with the blue and green labels, and now the features for the red dot are obtained and we would like to classify this as "I" or "C". Note that the feature for red circle is the ordered pair (e.g., 1, 16.5). The closest point to the boundary is (3,16). As such, the distance between these two points is 2.06, and the subsequent ISAP for this subject (e.g., subject 5) is $(2-e^{-2.06})/2$=93.64%. FIG. 22 shows a diagram of this exemplary quantitative data for the Individual State of Awareness Profile for the exemplary subject 5.

I.2.6.2. Exemplary Unsupervised Classifier with Likelihood Ratio Tests

In examples using the "unsupervised" classifier, the technique does not use any training data to train the classifier. Rather, the classifier takes in a batch of data and then specifies a decision about the likelihood of the brain categorizing information from word strings with different congruency in the same manner, or differently.

Exemplary Implementation Procedure of Unsupervised Classifier

The exemplary procedure for the unsupervised classifier in exemplary implementations using auditory stimuli presented to the subject was implemented in the same manner as described in previous section for the exemplary visual stimuli implementations.

Exemplary Results

Figure 23:
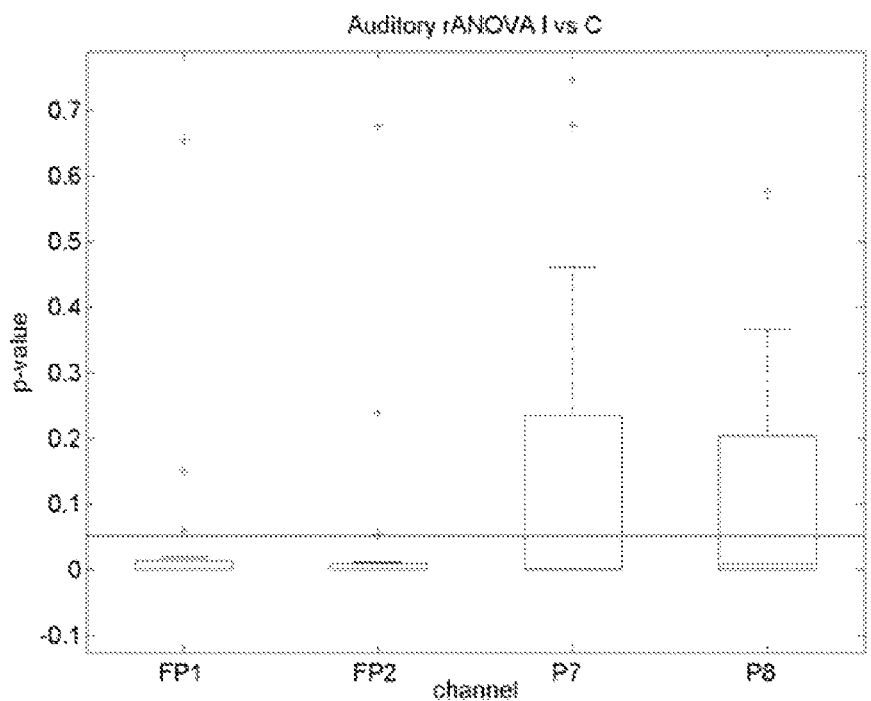
FIG. 23 shows a data plot and corresponding data table for an exemplary rANOVA analysis of I vs C using auditory stimuli.
Figures 24, 25:
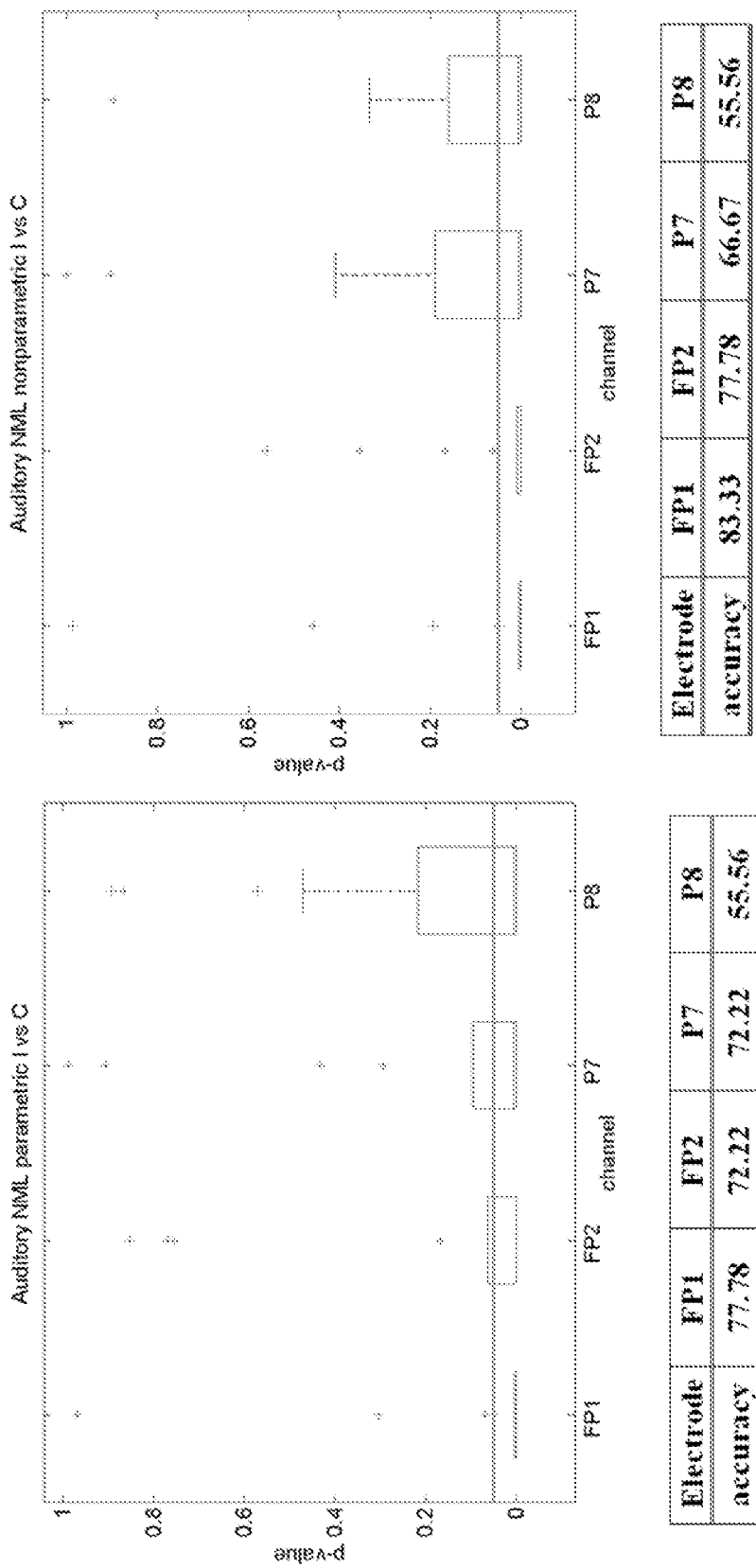
FIG. 24 shows a data plot and corresponding data table for an exemplary NML parametric analysis of I vs C using auditory stimuli.
FIG. 25 shows a data plot and corresponding data table for an exemplary NML nonparametric analysis of I vs C using auditory stimuli.

For each of the exemplary auditory stimuli paradigms presented to subjects, the exemplary performance of the different test statistics and methods of calculating p-values are shown in FIGS. 23-25. FIG. 23 shows a data plot and corresponding data table for an exemplary rANOVA analysis of I vs C using auditory stimuli. FIG. 24 shows a data plot and corresponding data table for an exemplary NML parametric analysis of I vs C using auditory stimuli. FIG. 25 shows a data plot and corresponding data table for an exemplary NML nonparametric analysis of I vs C using auditory stimuli.

In FIGS. 23-25, a box-plot of the p-values of the classifier is provided for specific electrode locations of interest, e.g., FP1, FP2, P7, and P8. The box plot provides the median (red line), standard deviation (width), and outlier information. The green horizontal line across each data plot corresponds to the threshold of the p-value being 0.05. All subjects with p-values below are thus classified correctly, and those above are classified incorrectly. Along with each box-plot, there is also a succinct, corresponding table describing the overall fraction of correct classifications (with p-value threshold at 0.05), over all subjects.

In FIGS. 23-25, the nomenclature is as follows:

"I vs C" denotes that d[t]=y[1,t]−y[2,t]: t=1:T, where y[1,t] pertains to the incongruent "I" auditory stimulus and y[2,t] pertains to the congruent "C" auditory stimulus. "NML" is succinct for the normalized maximum likelihood method of calculating a test statistic, section T.A, but where the test statistics g(d), is now given by g(d)=2cS$_{24}$(v), where $$v = \frac{\sqrt{25}\,\bar{d}}{s} \text{ and } c = \frac{\sqrt{25}\,|\bar{d}|}{s}.$$

"parametric" represents the parametric method of estimating a p-value, described in section P.A by performing Monte-Carlo estimation of the p-value, where the input to the test-statistic was drawn according to a Normal distribution with mean and variance estimated from the samples.

"nonparametric" represents the non-parametric method, P.B, of estimating a p-value.

"rANOVA" represents a test statistic and p-value calculation paradigm using a standard repeated measures ANOVA methodology, method P.A.1.

These exemplary analyses were performed individually and then averaged for a group dataset that included 20 subjects. It is noted, in these exemplary implementations, that for channels FP1 and FP2 (which are frontal and don't require gelling of hair), these exemplary classification methods exemplified accuracy uniformly in the 70-100% range. These exemplary results suggests that a system with only frontal electrodes can elicit high performance. The disclosed method does not need to always include acquiring frontal activity.

Exemplary Cognitive and/or Sensory Profile: Group State of Awareness Profile (GSAP) and Individual State of Awareness Profile (ISAP)

Using this last example of an unsupervised classifier embodiment, and selecting the frontal electrode FP1 to illustrate this profile, the final product of the exemplary implementation of the method can be in the form of an Individual State of Awareness Profile (ISAP) or in the form of Group State of Awareness Profile (GSAP).

Figure 26:
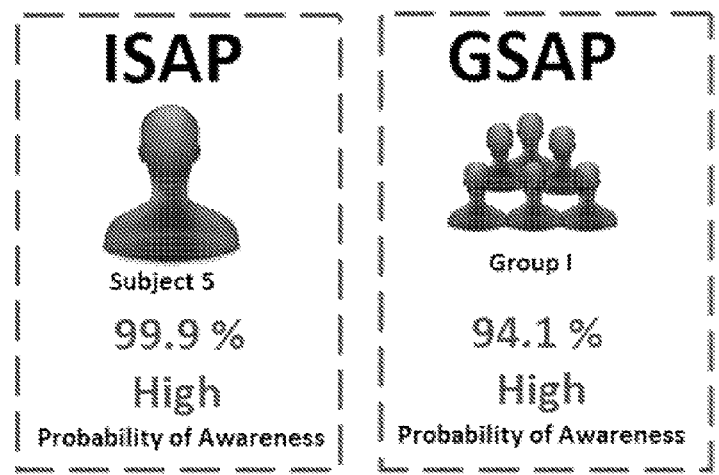
FIG. 26 shows diagrams of examples of Individual State of Awareness Profile for an individual subject and Group State of Awareness Profile for a group based subject.

For example, we identify the p-value for any subject and perform 100%-p-value, using the nonparametric likelihood ratio test (as in FIG. 25) as a measure of discrimination in tested categories. In the individual case, for the exemplary subject 5, the ISAP was 99.9%. At the group level (e.g., group 1), the median GSAP level was 94.1%. These exemplary results are shown in FIG. 26. FIG. 26 shows diagrams of examples of Individual State of Awareness Profile for an individual subject and Group State of Awareness Profile for a group based subject.

II. P300

The P300 is a brain endogenous response characterized by a positive-going electrical response between 300 and 800 ms, with a central-parietal maxima scalp distribution. The P300 is inversely correlated with an item's subjective probability of occurrence. For example, the P300 has been used in visual target detection tasks, where the target elicits higher amplitude P300s than the other items.

In the exemplary implementations described herein using the P300, an arbitrary visual cue (e.g., green circle) was created, and the tested subjects were instructed to associate it with a notion of "reward". The brain responses to this "reward" stimulus was subsequently analyzed. The exemplary illustrations of the disclosed methods using P300 illustrates the broad applicability of the methods across various EEG recording techniques. For example, the method is applied to assess cognitive and/or sensory profiles using brain data (e.g., EEG signals) recorded using a traditional rigid electrodes EEG system, as well as with EEG data acquired using wearable, flexible epidermal electronic sensors (EES).

In one example of an EES device, the device includes ultrathin silicon islands interconnected by serpentine-like wires that all rest on a biologically inert flexible polymer. The EES can sense a variety of signal modalities, e.g., including, but not limited to, temperature, strain, optics, and electrophysiology (e.g., EEG, electrocardiogram (ECG), and electromyogram (EMG) signals), and in some implementations, process the detected signals using a processing unit configured on the device. In some examples, the processing unit can be configured with transistors, capacitors, resistors, inductors, and other circuit elements, etc. In some implementations, for example, the processing unit of the EES device can include a processor and a memory unit. The EES device can be configured to have a thickness no thicker than a human hair. The EES device can be structured to include a flexible and stretchable substrate that is mechanically matched to the skin, in which the sensor components and processing unit components can be configured on or within the substrate. In some implementations, the EES device can include a transmitter unit to transmit the measured/detected information of activity, e.g., including physiological activity produced by the heart, skeletal muscles (e.g., such as throat muscle activity during speech or eye blinks) and the brain, e.g., detecting for instance alpha rhythms produced when subjects have their eyes closed.

II.1. P300 with a Visual and/or Auditory Stimuli Paradigm

II.1.1. Exemplary Stimuli

In one example implementation, examined were the brain responses using the P300 brain marker in response to colored images in a target detection task across multiple electroencephalography (EEG) techniques. For example, two brain recording techniques were implemented: a traditional rigid electrodes EEG system (e.g., the Brain Products system, as described in the previous section) and an EES device. Moreover neural responses to a feeling/notion of "reward" were also examined. Both ERPs (P300 and "reward") were each elicited by a correlated visual stimulus. For example, the stimuli were comprised of multiple image categories, e.g., including animals; cars; faces; flowers; houses; random objects; motorcycles; airplanes; and buildings. The exemplary pool of stimuli was obtained from various resources. After obtaining the stimuli pool, each exemplar's relative luminance was controlled using a computer implemented method (e.g., programmed with a MATLAB script). For example, the computer implemented method was implemented to first load in a color image, and calculate its relative luminance using the following exemplary formula, where Y, R, G, and B represent relative luminance, red gun values, green gun values, and blue gun values, respectively:

$$Y = 0.2126R + 0.7152G + 0.0722B \tag{1}$$

For example, the desired relative luminance was set to be a value equal to 120. After the script measured the initial relative luminance of each image, it either added or subtracted RGB values to every pixel within the image in order to achieve an average relative luminance of 120. Images were then saved at 100% quality.

After controlling for luminance, another computer implemented process (e.g., programmed using a MATLAB script) was used to place a centrally positioned fixation dot on each stimulus exemplar. For example, this helped the subject to maintain fixation and minimize any frequent eye saccades. This exemplary process first measured the dimensions of an uploaded image. It used these measurements to calculate the center of the image and subsequently create a fixation dot using the standard equation of a circle. Pixels within a seven pixels length radius around the center were altered by changing the pixels' red gun to 255, the green gun to 0, and the blue gun to 0.

Lastly, the visual stimuli for the fixation dot and an arbitrary visual cue for "reward" were created. For example, for the fixation dot, a computer implemented process (e.g., programmed using a MATLAB script) was used to create a grey background image (e.g., red gun equal to 150; green gun equal to 150; blue gun equal to 150) with a height and width of 350 pixels. Then, the exemplary script ran a nested for-loop using the standard equation of a circle to alter pixels within a seven pixels length radius to red, e.g., by changing the image's red gun to 255, the green gun to 0, and the blue gun to 0. For the "reward", imaging software was used to create a green circle (e.g., red gun equal to 0; green gun equal to 255; blue gun equal to 0) on a 350×350 pixels grey background (e.g., red gun equal to 150; green gun equal to 150; blue gun equal to 150) background.

II.1.2. Subject Preparation for EEG Recording

To prepare the exemplary subjects for EEG recording, each subject was seated in a chair in a recording chamber to begin an EEG capping process. Each subject underwent each of the two EEG recording techniques (e.g., the rigid electrodes (Brain Products) modality and the flexible, wearable, portable electronics (e.g., exemplary EES device) modality).

For the exemplary implementations using the rigid electrode modality, this process involved placing a traditional EEG cap on the subject's head and securing it with an elastic chin strap. In some examples, either a 56 cm or a 58 cm diameter cap was used, based on the estimated size of the subject's head. Next, Signa electrode gel (e.g., from Parker Laboratories) was injected using a curved, plastic syringe under each of the cap's electrodes to create a conductive bridge between the electrode itself and the subject's scalp. Also, for example, wooden Q-tips were used to massage the gel in order to build a stronger conductance by lowering the impedance. For example, use of this technique lowered the impedance levels to <5 kΩ for each electrode, e.g., including the ground and reference.

For the exemplary implementations using the exemplary EES device, the subject's forehead was first cleaned using an alcohol swab and sterile gauze. After allowing the alcohol to dry, an exemplary EES device was placed on the subject's forehead, with the EES' ACF cables aimed toward the subject's right hand side. The subject was instructed to tilt his/her head back as the exemplary EES device was wet with tap water, e.g., using a curved, plastic syringe. At the same time, the subject used a paper towel to cover their eyes from the water. For example, a moist finger can be used to gently rub the EES until it adheres and is flush with the forehead. Afterward, in these examples, a Nexcare No Sting Liquid Bandage was used to more firmly bond the EES to the forehead. While allowing the Liquid Bandage to dry, the EES' DIN cables were taped to the subject's head using masking tape. For example, this prevented the cables from falling into the subject's field of view and also prevented the cables from pulling on the EES itself. Also for example, additional measure were taken to prevent pulling by clipping the DIN cables to the subject's shirt collar.

Before starting the exemplary implementation using EEG recordings, subjects were given an instructions document to read. For example, this document described the general organization of the experimental paradigm and what they would be viewing, namely targets, distractors, a fixation dot and a blue square. It was also explained that in each presentation block, the target would change. For example, in block 1, the task was to count how many times they saw an image with one or more human faces. In block 2, the task was to count how many times they saw an image with one or more cars. In block 3, the task was to count how many times they saw an image with one or more animals. The subjects were instructed to regard all other photographs as distractors and not count them. After each presentation block, the subjects were asked to report how many targets they saw. For example, the blue square indicated reward. The subject subjects were seated in front of the presentation monitor and asked to just maintain visual fixation on a red, central fixation dot throughout the duration of the experiment and restrict their motor movements as much as possible to prevent motion artifacts in the neurophysiological data. Afterwards, the recording room's lights were then dimmed, and the stimulation process and EEG recordings began.

II.1.3. Exemplary Stimuli Presentation Process

The exemplary stimulus presentation paradigm that was used in this example stimuli presentation process was programmed using Cogent 2000, and included presenting visual stimuli serially with brief presentation durations. For example, the pool of stimuli, not including the fixation dot and green circle, was divided into two groups, one for each of the two recording techniques. Each technique included 900 stimuli, for a total of 1800 stimuli across recording techniques. For example, within a technique, the 900 stimuli, including targets and distractors, each presented for 100 ms, were divided into three presentation blocks. The blue square stimulus presentation lasted 1000 ms and was shown 30 times within each presentation block. The fixation dot was visible during every target trial, distractor trial, and inter-stimulus interval (ISI).

For example, in block 1, targets were human faces. In block 2, targets were cars. In block 3, targets were animals. In addition to randomizing the order of the recording techniques, we also randomized the order of the presentation blocks within each technique. Presentation blocks were never repeated consecutively (e.g., block 1, block 2, block 3, block 3, block 2, block 1, block 3, block 2) across techniques. Because the subject was instructed to count how many times he saw a particular target, we varied the correct number of targets for each block. In block 1 (target: faces), there were 56 targets and 244 distractors. In block 2 (target: cars), there were 62 targets and 238 distractors. In block 3 (target: animals), there were 60 targets and 240 distractors. Distractors were composed of all of the non-target object categories. For example, in block 1 (target: faces), the distractors included cars, animals, flowers, houses, etc. The MATLAB code began by prompting the experimenter to enter the subject's initials and choose which block to present. Depending on the chosen block number, the script calculated which object category would be target, the number of targets, and the number of distractors. Afterward, it randomized the order of stimulus presentation using the MATLAB randperm( ) function. It ran the randperm( ) function twenty times to better randomize the presentation sequence. Then, it created inter-stimulus intervals (ISI) for each trial using the randi( ) function. The inter-stimulus intervals ranged from 500 ms to 600 ms. In addition to configuring the display, sound card, and parallel port, a log file was configured and initialized within Cogent 2000. This log file was used to create a history of every trial regarding its stimulus type (target, distractor and blue square). Subsequently, the stimuli were loaded into memory buffers. The aforementioned steps were executed prior to stimulus presentation in order to reduce computational load and increase latency precision. The stimulus presentation included using a for-loop that iterated down the pre-determined presentation order. For example, based on the value of the current stimulus in the presentation order, the computer implemented process calculated its stimulus type and sent the appropriate information regarding its stimulus type to the log file and parallel port, whose trigger was sent to the EEG recording computer. Then, the program presented the ISI. At the end of each presentation, the parallel port was reset to zero to prepare for the next trial.

Figure 27:
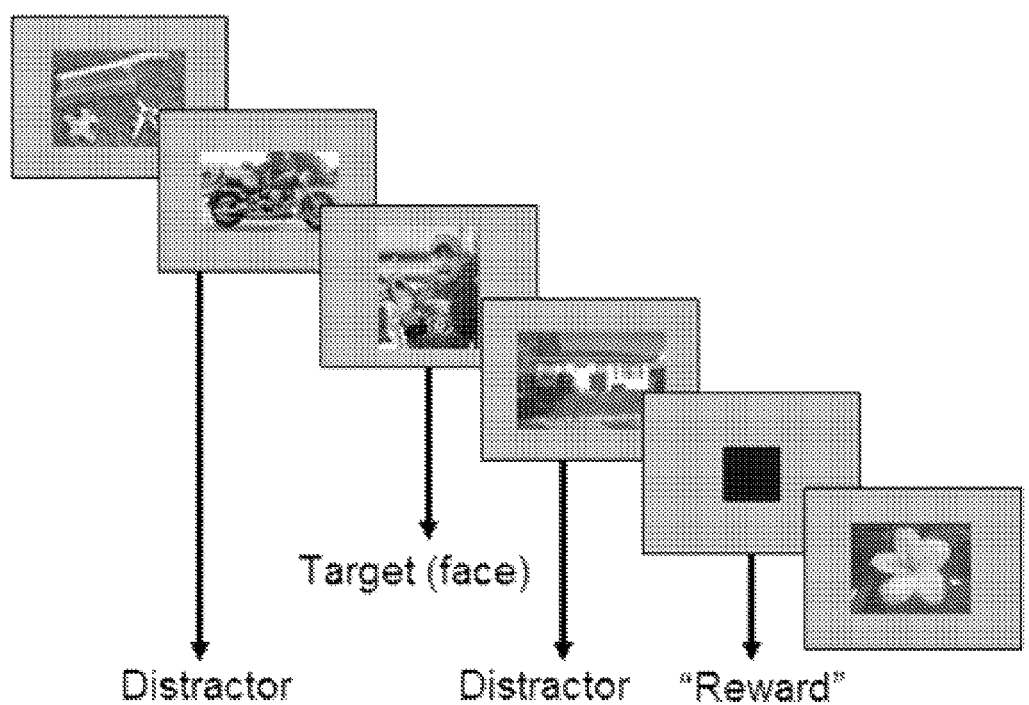
FIG. 27 shows a diagram of an exemplary sequence of presented visual stimuli.

FIG. 27 shows a diagram of an exemplary sequence of presented visual stimuli. This diagram portrays images of specific presented exemplars and the pre-programmed pseudo-randomized order of presentation Having the adequate stimuli presentation structure for each solution is an intrinsic and important part of the exemplary method. In this example, the relevant aspect is the distinction between the images that represent pre-determined "Targets" versus all other images (labeled as "Distractors") and versus the blue-square previously associated with an indication of "Reward". The adequate stimuli structure with the specific content of images of interest as targets embedded in a sequence of other images and the described specialized subsequent analysis are important in the exemplary method to how to use relevant brain markers, e.g., in this exemplary case, the P300 and the "reward" elicited ERPs, to evaluate and determine individual knowledge, levels of attention and preferences to specific items, creating an Individual Knowledge/Preference Profile.

For example, in some applications, this profile is then evaluated by a posterior matching algorithm to guide and/or adjust brain-machine interface controlling an adaptive change of the subsequent stimulation. This can be used, for example, in assisted-learning applications or preference triage applications, e.g., where after determining a person knowledge or preference profile, the brain-machine interface can adjust the following stimulation by re-enforcing the type of information where the student showed deficient learning in the first case, or by adjusting to following presented items to a personal set of preferences in the latter.

II.1.4. Exemplary Brain Waves (EEG) Recordings

In some implementations, a traditional EEG system with rigid electrodes was used to acquire brain waves. The exemplary EEG system included a BrainAmp DC 32-channel system; BrainVision Recorder; Fast n Easy 32-channel EEG recording cap size 56 cm; Fast n Easy 32-channel EEG recording cap size 58 cm; PCB Ribbon Cable for BrainCap-MR with 5 k resistors; and BrainCap MR Box 1.2. The exemplary EES sensors cables were connected to this same EEG system.

II.1.5. Exemplary Pre-Processing Analysis Techniques

The exemplary analysis pre-processing techniques of the disclosed methods using a visual stimuli paradigm can include techniques for processing the marker data. For example, after each recording session, the exemplary EEG recordings system produced three files: data file (.eeg), header file (.vhdr), and marker file (.vmrk). The marker files contained the event triggers for each stimulus onset. In this example, because of output limitations within the parallel port, the Cogent 2000 log file was used to hold more readable information regarding an exemplar's stimulus type (e.g., target, distractor or green circle). From there, a process (e.g., programmed using a MATLAB script) to replace the event triggers in the marker file (.vmrk) with the event codes from the log file in a one-to-one replacement. For example, the first marker in the .vmrk file was replaced by the first marker in the log file; the second marker in the .vmrk file was replaced by the second marker in the log file, etc.

The exemplary analysis pre-processing techniques of the disclosed methods include techniques for general individual statistical analysis. In the exemplary implementations described herein, a combination of MATLAB and Statsoft Statistica (version 8.0) software was used for statistical analyses. After data processing and analysis, the BrainVision Analyzer of the exemplary EEG recording system exported text files containing data values in regards to condition, subject, trial, electrode channel, and mean voltage amplitude. For example, for the 32 electrode EEG cap technique, the mean voltage amplitude was extracted for a frontal electrode (FP2) for the following time intervals of interest: Targets and Distractors—352 ms to 452 ms after stimulus onset; Reward stimuli—452 ms to 552 ms after stimulus onset. For the EES technique frontal electrodes, the same parameters were used. These data were written to text files by BrainVision Analyzer of the exemplary EEG recording system and subsequently loaded into a computer implemented program (e.g., a MATLAB program) to sort and organize the data in a more accessible format. Specifically, for example, the exemplary computer implemented program allows one to more easily select data by column, e.g., using MATLAB's variable editor. After selecting, data were copied and pasted into Statistica data spreadsheets.

For example, one-way (factor 1: condition) repeated measures ANOVAs were performed on each Statistica spreadsheet for the comparison between distractors and targets for each of the EEG recording techniques. For example, each spreadsheet was specific to the following: (1) EEG techniques: rigid electrodes EEG cap or EES electrodes; (2) comparison: distractors vs. targets. For the reward condition, a T-test comparing the reward's extracted mean amplitude values against zero was performed. For example, each spreadsheet was specific to the following: (1) EEG techniques: rigid electrodes EEG cap or EES electrodes; (2) comparison: distractors vs. targets. For the comparison between distractors and targets using the Fp2 electrode from the Brain Products EEG cap, a significant effect was found: with $F(1, 140)=12.184$ and a p-value of 0.00064. For the comparison between distractors and targets using the EES' recording electrode, a significant effect was found: with $F(1, 148)=17.307$ and a p-value of 0.00005. For the comparison between reward and a zero constant from the Fp2 electrode from the Brain Products EEG cap, a significant effect was found: with a mean of 218.180138571428, a standard deviation of 895.427245848706, an N sample size of 89, a standard error of 34.6498548937238, a T-value of −3.13915892165244, degrees of freedom of 88, and a p-value of 0.00230642892515112. For the comparison between reward and a zero constant from the EES' recording electrode, a significant effect was found: with a mean of 218.180138571428, a standard deviation of 895.427245848706, an N sample size of 70, a standard error of 107.024026181588, a T-value of 2.03860895871402, degrees of freedom of 69, and a p-value of 0.0453228914525858.

I.1.6. Exemplary Implementations Across Different EEG Sensing Technologies

As described in section II.1.2 Subject preparation for EEG recording, to demonstrate both the feasibility and maintained accuracy of the exemplary method across EEG recording technologies, the same paradigm was implemented using a traditional full EEG cap with rigid electrodes and an exemplary wearable, portable EEG sensor system, e.g., the epidermal electronics system with flexible electronics electrodes.

II.1.6.1. Rigid Electrodes EEG System

FIGS. 28A and 28B show images and data plots of exemplary results from implementation of the data acquisition and processing processes of the exemplary method using an exemplary rigid electrode EEG system, with individual (e.g., single subject) statistical analysis showing brain patterns of discrimination between "Target" and "Distractor" images and associated with a notion of "Reward". FIG. 28A shows an image depicting the individual subject wearing the rigid electrode EEG sensor cap 2800 of the EEG system. FIG. 28B shows a plot 2801 showing the exemplary ERP responses to "Targets" (red line) versus "Distractors" (black line) and a plot 2802 showing the ERP response to the blue square image associated with "Reward" (blue line), in which the exemplary data displayed in the plots 2801 and 2802 were determined from processing performed using available EEG analysis software (e.g., BrainVision Analyzer2). FIG. 28B shows a plot 2811 showing the exemplary ERP responses to "Targets" (red line) versus "Distractors" (black line) and a plot 2812 showing the ERP response to the blue square image associated with "Reward" (blue line), in which the exemplary data displayed in the plots 2811 and 2812 were determined from the same processing analyses using custom-designed code developed by us.

Notably, as depicted in FIG. 28B, by applying at least a portion of the exemplary method including at least part of the analyses processes, brain data can be acquired using the rigid electrode EEG cap and processed such that it reflects (in a statistically significant manner) individual responses to discriminating images of interest from other images, and visual cues associated with "reward". Subsequently, remaining processes of the exemplary method can be applied (e.g., the guided classification algorithms, etc.) can be implemented to produce an Individualized Knowledge Evaluation Profile. Also, for example, as shown in FIG. 28B, by using our exemplary custom-designed code, the same ERP calculation analysis can be performed, which obtained a comparable performance accuracy (e.g., comparable p-values) when using the rigid electrodes EEG system (e.g., Targets vs. Distractors: commercial software (p=0.00064) and our exemplary custom-designed analysis code (p=0.0000); Reward: commercial software (p=0.0023) and our analysis code (p=0.0144)).

II.1.6.2. Epidermal Electronics Sensors EEG System

FIGS. 29A and 29B show images and data plots of exemplary results from implementation of the data acquisition and processing processes of the exemplary method using an exemplary flexible epidermal electronics sensor device EEG system, with individual (e.g., single subject) statistical analysis showing brain patterns of discrimination between "Target" and "Distractor" images and associated with a notion of "Reward". FIG. 29A shows an image depicting the individual subject wearing the exemplary EES device 2900 of the EEG system. FIG. 29B shows a plot 2901 showing the exemplary ERP responses to "Targets" (red line) versus "Distractors" (black line) and a plot 2902 showing the ERP response to the blue square image associated with "Reward" (blue line), in which the exemplary data displayed in the plots 2901 and 2902 were determined from processing performed using available EEG analysis software (e.g., BrainVision Analyzer2). FIG. 29B shows a plot 2911 showing the exemplary ERP responses to "Targets" (red line) versus "Distractors" (black line) and a plot 2912 showing the ERP response to the blue square image associated with "Reward" (blue line), in which the exemplary data displayed in the plots 2911 and 2912 were determined from the same processing analyses using custom-designed code developed by us.

Notably, as depicted in FIG. 29B, by applying at least a portion of the exemplary method including at least part of the analyses processes, brain data can be acquired using the user-wearable EES device and processed such that it reflects (in a statistically significant manner) individual responses to discriminating images of interest from other images, and visual cues associated with "reward". Subsequently, remaining processes of the exemplary method can be applied (e.g., the guided classification algorithms, etc.) can be implemented to produce an Individualized Knowledge Evaluation Profile. Also, for example, as shown in FIG. 29B, by using our exemplary custom-designed code, the same ERP calculation analysis can be performed, which obtained a comparable performance accuracy (e.g., comparable p-values) when using the flexible, wearable electronics EEG system (e.g., Targets vs. Distractors: commercial software (p=0.0000) and our exemplary custom-designed analysis code (p=0.0000); Reward: commercial software (p=0.0453) and our analysis code (p=0.0002)).

II.1.6.3. Exemplary Processing and Guided Classification Techniques (e.g., with Context Specific Parameters)

In this section, the ability to develop classifiers for individual knowledge and reward evaluation is described. For example, in the exemplary implementations, each subject was provided a full EEG cap (e.g., for the rigid electrodes EEG system) as well as a wearable forehead-mounted EEG sensor device, as previously discussed. The exemplary P-values reported in the previous section were from an individual and thus directly applicable in this context. As such, the reward and distractor stimuli can be provided, and a P-value can be calculated using a t-test on the difference between target and distractor waveforms, e.g., as reported from electrode FP1 using a rigid or epidermal electronics system. For example, in such cases, 100%−P-value can be used as a measure for the individual knowledge evaluation profile (IKEP). For example, analogous methods are directly applicable for assessment of reward.

Figure 30:
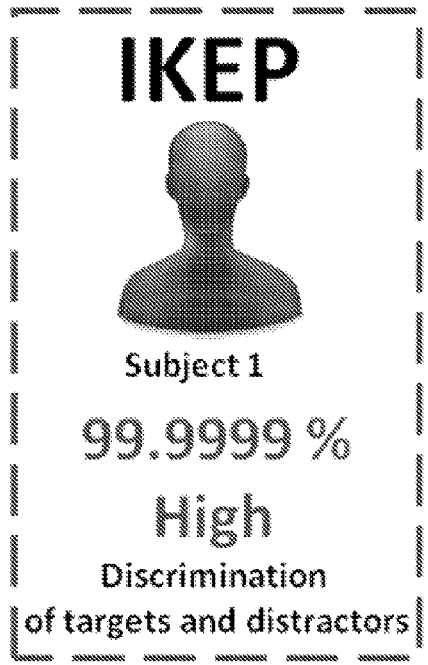
FIGS. 30-33 show diagrams depicting exemplary results of IKEP quantitative analyses using a rigid electrodes EEG system and a flexible epidermal electronics sensor EEG system.
Figure 31:
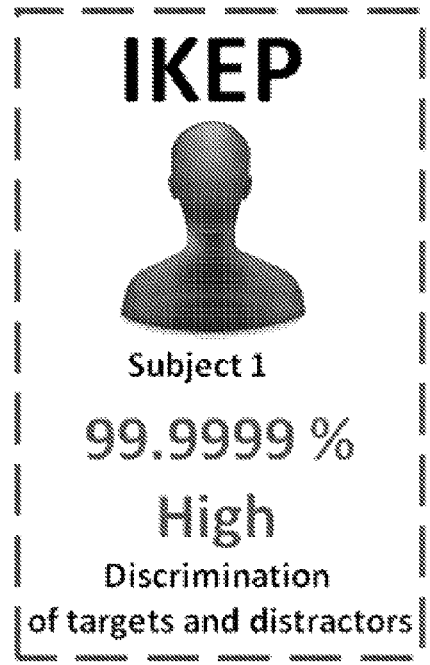
Figure 32:
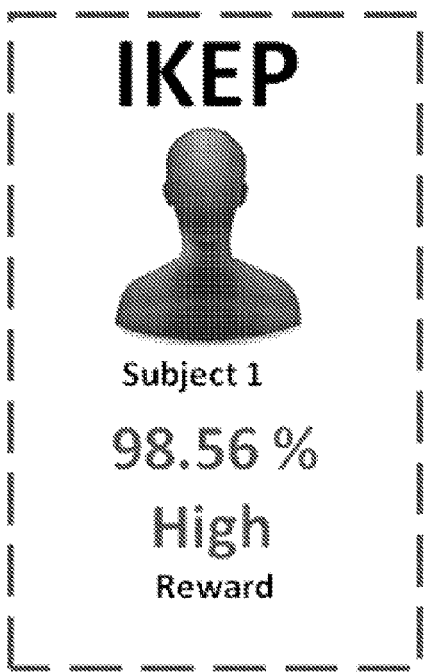
Figure 33:
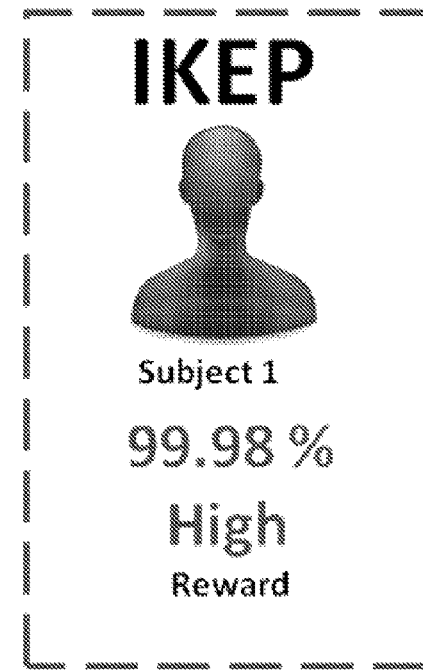

As such, using the p-values from the previous section, the exemplary results were determined in the following individualized knowledge evaluation profiles, as shown in the diagrams of FIGS. 30-33. FIG. 30 shows a diagram depicting the exemplary IKEP quantitative level for discrimination of targets and distractors of an exemplary subject (e.g., subject 1) using the rigid electrodes EEG system, FP1 electrode, for the P300 ERP, which was determined to be 99.9999%; High. FIG. 31 shows a diagram depicting the exemplary IKEP quantitative level for discrimination of targets and distractors of an exemplary subject (e.g., subject 1) using the epidermal electronics sensor device EEG system for frontal P300 ERP, which was determined to be 99.9999%; High. FIG. 32 shows a diagram depicting the exemplary IKEP quantitative level for reward of an exemplary subject (e.g., subject 1) using the rigid electrodes EEG system, FP1 electrode, which was determined to be 98.56%; High. FIG. 33 shows a diagram depicting the exemplary IKEP quantitative level for reward of an exemplary subject (e.g., subject 1) using the epidermal electronics sensor device EEG system, which was determined to be 99.98%; High.

Brain-Machine Interface

As shown previously in FIG. 1A, the system 100 includes a brain-machine interface module 160, which can actuate an interaction between a user and a machine. In one example, the brain-machine interface module 160 can provide a feedback delivery of a new stimulus or multiple stimuli to the stimulus presentation module 110 based on the cognitive and/or sensory profile of an individual subject or group subject (e.g., IKEP, ISAP, GKEP, GSAP) that has been generated from the profile generation module 150, e.g., from an on-going implementation of the system 100 or a previously generated profile by the system 100.

In this section, an exemplary framework is described that is generally applicable to a sequential experimental design, which is a sequential way to probe a user to extract meaning about his/her cognitive state. In an illustrative example, for instance, suppose a user has a specific point on a map that he/she is interested in zooming upon. Implementation of the sequential experimental design methods and systems can be used to partition the map into a plurality of sub-maps (e.g., 4 quadrants), such that an experiment is designed so that a neural and/or behavioral response will be statistically correlated to the sub-map (e.g., the quadrant) containing the point of interest. The system updates its knowledge on the point of interest, and optimizes the subsequent display of the map and/or quadrants. The system can be designed to minimize the number of experiments (e.g., probing stimuli) until the point of interest has been extracted (with high fidelity).

For example, in such settings, an experiment can be conducted to guess which of a class of hypotheses has occurred. After evidence has been collected, a subsequent experiment will be conducted. To rapidly reduce uncertainty about which hypothesis has occurred, the design of the second experiment typically should depend on the outcome (e.g., acquired information) of the first.

Within the context of the exemplary framework of the disclosed technology, the outcome of the previous experiment pertains to the individualized knowledge evaluation profile or state of awareness profile along with behavior information that has been constructed. Important to those profiles, for example, is that they encode a set of statistical beliefs about the likelihood of certain hypotheses as compared to others. Described is a framework to guide the subsequent stimulus presentation so that the system extracts information about the user/subject as efficiently as possible.

Figure 34A:
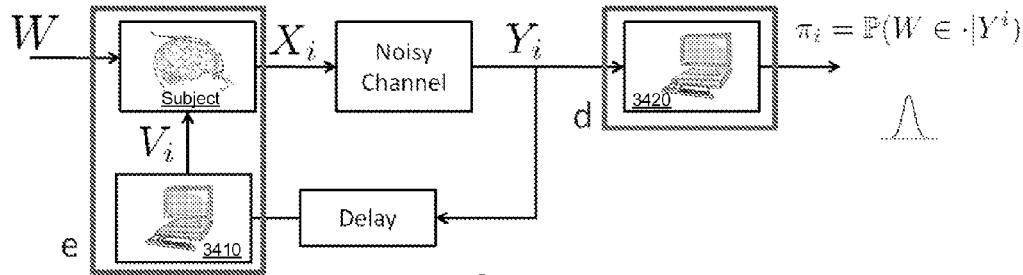
FIG. 34A shows a block diagram of an exemplary model for using a brain machine interface in the disclosed methods for refining cognitive and/or sensory profiles.

FIG. 34A shows a block diagram of an exemplary model for using a brain machine interface in the disclosed methods for refining the cognitive and/or sensory profiles. As shown in the block diagram, the index "i" pertains to the index of a current implementation being conducted. The index "i" and the feedback arrow (from right to left) denotes the sequential nature of the framework, and how previous experiments and statistical information about the brain affect what subsequent sensory stimuli will be. "W" represents the brain state of information (e.g., how a subject categorizes information). "$X_i$", represents the contextual brain state (e.g., memory triggered, categorization violation, or behavioral plan, etc.) that depends upon W and the current sensory stimulus $V_i$. A processing module 3420 (e.g., computer) updates its statistical information, given in terms of a probability distribution $\pi_i$ it maintains and updates. For example, after physiological and/or behavioral data is collected, a knowledge/awareness profile is generated, e.g., by the data processing module 3420, given by $\pi_i$. The knowledge/awareness profile ($\pi_i$) includes statistical information that is given to a decision-making engine 3410 that performs computations and identifies the next subsequent stimuli that form the basis of the subsequent experiment. As shown in the diagram, the stimulus (given by $V_i$) that is provided to the subject can interact with the subject's knowledge/awareness (given by W) to produce a subsequent brain response (given by $X_i$). This is observed across a noisy channel by a data processing module 3420 measuring and/or analyzing neural and/or behavioral signals (given by $Y_i$). The brain-machine interface can be implemented to specify the subsequent sensory stimulus $V_i$ so that information about W is extracted as efficiently as possible.

As such, the exemplary sequential experimental design includes procedures, so that after n experimental uses, the following are maximized: the mutual information (or equivalently, minimized the uncertainty), $I(W;Y^n)$, between knowledge/awareness (given by W), and the acquired neural and/or behavioral signals (given by $Y_1 \ldots Y_n$):

$$\frac{1}{n} I(W; Y^n) \leq C. \tag{2}$$

The amount of information that can be extracted per experiment is upper bounded by the channel capacity of the noisy channel between the contextual brain state X and the neural and/or behavioral recordings Y. As such, the normalized mutual information is bounded as above. Provided herein is a sequential sensory stimulus paradigm to adapt the subsequent experimental design to force the previous inequality to be equality. For example, sufficient conditions for this are to 'hand the decoder what is missing', meaning that the subsequent contextual brain state $X_i$ should be statistically independent of all previous neural recordings $Y_1 \ldots Y_{i-1}$. The core objective of many sequential experimental design paradigms is to adaptively design stimuli paradigms so that the aforementioned inequality indeed is equality. Throughout the rest of this section, any methodology that results in equality above is termed "optimal".

The disclosed technology includes methods to adaptively design stimuli paradigms that optimally extract information. For example, we provide an explicit efficient algorithm in a technique that provably converges to the optimal solution, when the latent information of interest is in an arbitrary dimension. The exemplary approach gives rise to a sequential methodology that can be efficiently implemented on a variety of hardware implementations (e.g., including, a cell phone, tablet, desktop and/or laptop computer processors, among others) in real time.

Figure 34B:
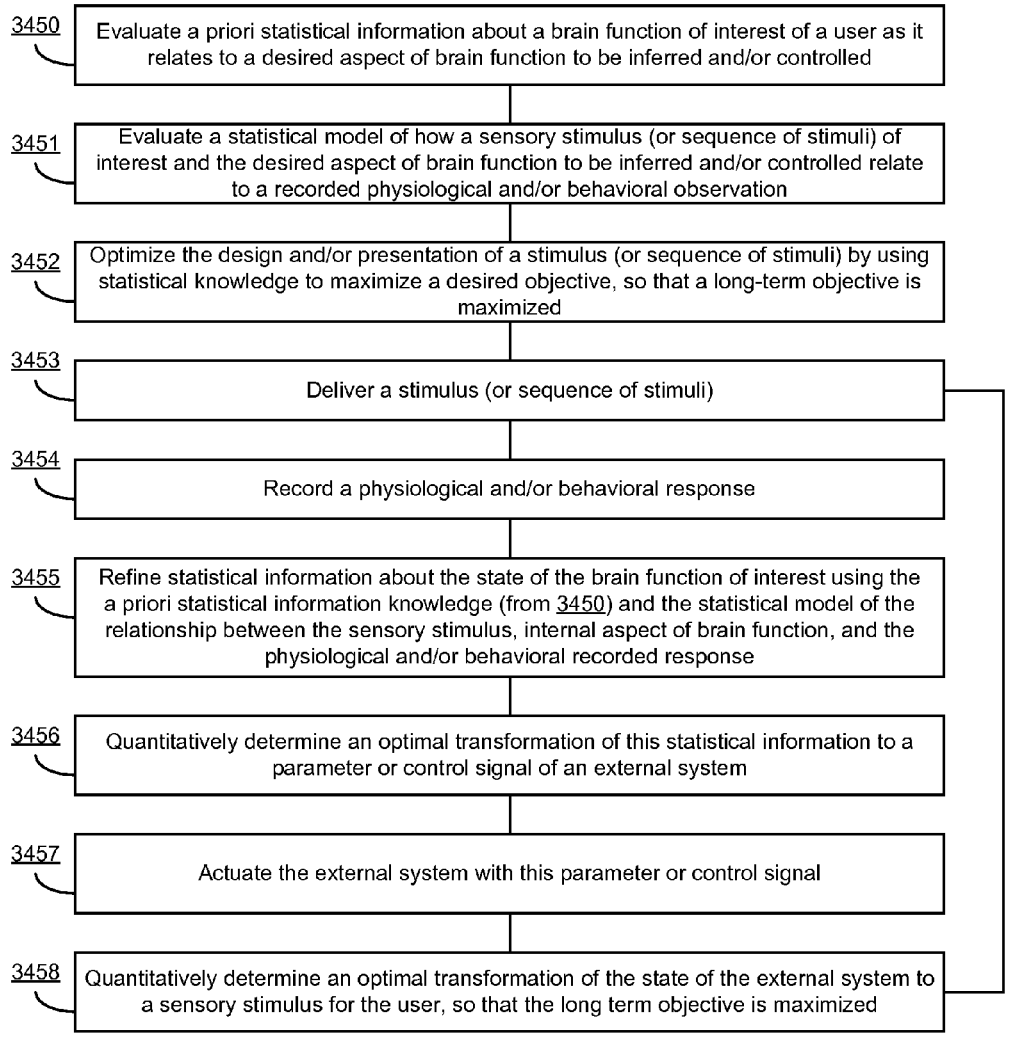
FIG. 34B shows a process diagram of an exemplary method to adaptively design stimuli paradigms that optimally extract desired information.

FIG. 34B shows a process diagram of an exemplary method to adaptively design stimuli paradigms that optimally extract desired information. For example, implementation of the method shown in FIG. 34B can provide a manner in which statistical knowledge about an aspect of brain function is sequentially estimated and/or controlled to achieve a desired objective, in real time. The method can include a process 3450 to evaluate a priori statistical information about an aspect of brain function of interest of a user (e.g., from previous uses with this user, such as a known clinical status of this user, or group knowledge about other users who share a similarity with this individual, such as others with a particular neurological deficit or pathology) as it relates to the aspect of brain function that is desired to be inferred and/or controlled. The method can include a process 3451 to evaluate a statistical model of how (1) a sensory stimulus (or sequence of stimuli) of interest and (2) the desired aspect of brain function to be inferred/controlled relate to a (3) recorded physiological and/or behavioral observation. The method can include a process 3452 to optimize the design and/or presentation of a stimulus (or sequence of stimuli), e.g., visual, auditory, somatasensory, gustatory, etc., by using a computational method that uses this statistical knowledge to maximize a desired objective, so that a long term objective is maximized. The method can include a process 3453 to deliver the stimulus (or sequence of stimuli) to the user. The method can include a process 3454 to record a physiological and/or behavioral response to the presented stimulus (or sequence of stimuli) from the user. The method can include a process 3455 to refine statistical information about the state of brain function of interest using a priori statistical knowledge specified in the process 3450 and the statistical model of the relationship between the (1) sensory stimulus of interest, the (2) internal aspect of brain function, and (3) the recorded physiological and/or behavioral response. The method can include a process 3456 to quantitatively determine an optimal transformation of this statistical information to a parameter or control signal of an external device, e.g., such as in illustrative examples like determining and/or controlling a position of cursor on a computer screen, torque dynamics of a robotic system, or a color map of pixels on a computer screen. The method can include a process 3457 to actuate the external device with this parameter or control signal that was optimized in the process 3456. The method can include a process 3458 to quantitatively determine an optimal transformation of the state of the external system to a sensory stimulus for the user, so that a long term objective is maximized. For example, an illustrative example can include mapping the torque dynamics of a robotic system to sounds displayed back to the user). The method can include repeating the method at the process 3453. In some examples, maximization of long term objectives can include minimizing the sum of errors between a desired trajectory in a subject's mind and the true trajectory of the exemplary external system (e.g., the robotic system). In some examples, maximization of long term objectives can include minimizing the number of times the recursive loop performed in the method that are iterated until the statistical information about the state of brain of interest has sufficiently high fidelity. The described method can be generally applied across a wide scope of applications for optimizing and refining statistical knowledge about various the states of the brain to learn about or effectuate.

In some approaches, when the latent information of interest, W, can be represented as a point on the unit interval (e.g., a [0,1] line), the procedure of "probabilistic bisection" can be used to develop "zooming-in" at a rate that is theoretically optimal and maximizes mutual information. This framework can be used for brain-computer interfaces to specify sentences and smooth paths.

Figure 35:
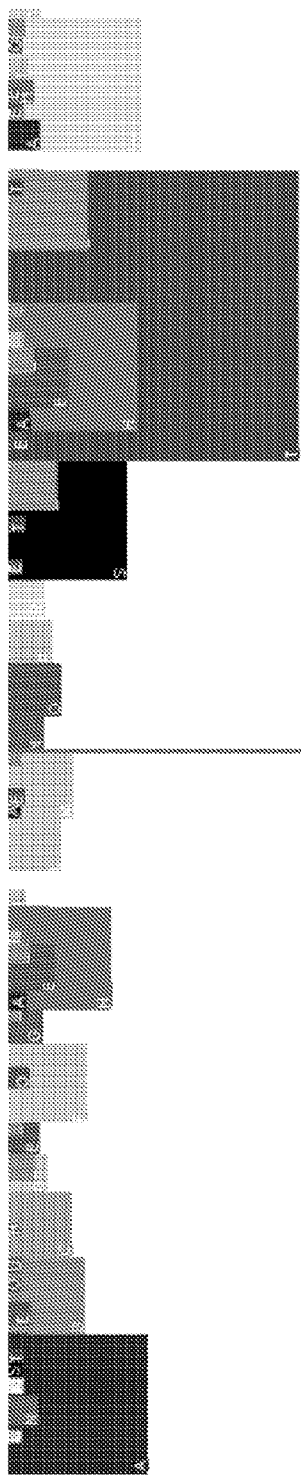
FIG. 35 shows a mapping of the unit interval [0,1] line to the set of all possible character sequences.

FIG. 35 shows an exemplary mapping of the unit interval [0,1] line to the set of all possible character sequences. As shown in the mapping diagram, for instance, the set of all sentences that begin with "t" take up a significant amount of space. The amount of space that is used is proportional to the likelihood of that character appearing. Note that the sequence "th" lies within the interval for "t". In this sense, for example, this is analogous to some systems that change visual displays based upon data compression and the statistics of language. However, one key difference is that this methodology described here sequentially updates itself not only taking into account the statistics of language, but also the fact that signals are being received across a noisy channel. In this example case, the user identifies where the target W of interest lies on the current display. If it is to the left of the red vertical line, he/she imagines squeezing the left hand, otherwise right. The system acquires neural signals and updates its posterior belief $\pi_i$. An exemplary system of the disclosed technology takes this information and uses it to "zoom in" on things that are more likely, zoom out on those that are less likely, and guarantee that it is probabilistically zooming in on the target sentence W as fast as possible.

It is noted that in FIG. 35, each character in the English alphabet pertains to a non-overlapping interval of the [0,1] line, arranged in increasing order from A to Z. Moreover, characters that are more likely have larger width. Within any character (e.g., T), the English alphabet is again placed in increasing order. Within this interval, the width of any character is proportional to the likelihood of seeing that character given the first letter is T. This was specified based upon a statistical model of the English alphabet. In this example, the latent brain state W pertains to a sequence of characters that comprise a sentence, e.g., "THE BLACK CAT JUMPED OVER THE LAZY DOG". The subject combines its latent brain state (or intent) and compares where that current display $V_i$ is located, in comparison to a vertical red bar. If it lies on one side, then the subject provides a binary input (e.g. imagining squeezing the left hand, as compared to the right) and the system acquires neural signals which are a "noisy" version of that input. The system updates its posterior belief about the likelihood of all possible sentences given the neural signals it has acquired. With this, it implements probabilistic bisection, which simply re-draws all possible sentences by iterating them through a map pertaining to the cumulative distribution function of the posterior distribution.

Figure 36:
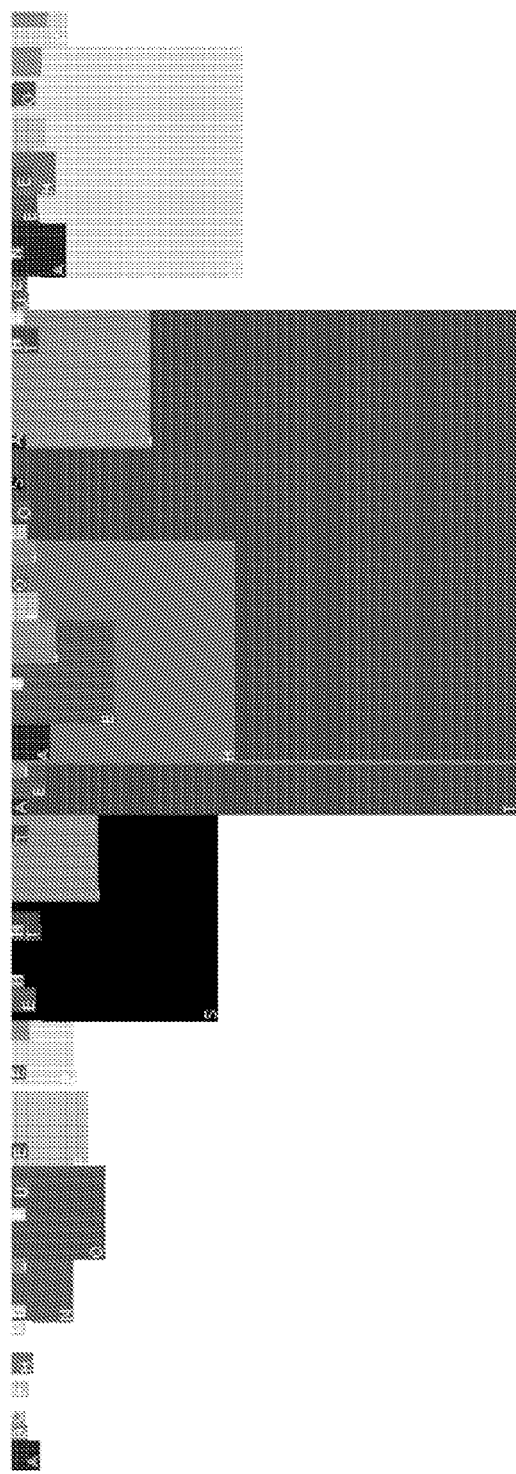
FIG. 36 shows a mapping after computation of an exemplary optimal map, e.g., in which a system applies it and re-draws all possible sentences.

FIG. 36 shows a mapping after computation of an exemplary optimal map, e.g., in which the system applies it and re-draws all possible sentences. In this case, W pertains to the sentence "The black cat jumped over the lazy dog". Note that sentences beginning with "The . . . " are significantly zoomed in. As shown in FIG. 36, after application of this map, sentences beginning with "T" are zoomed in on, and others are zoomed out on. Although there is inherent noise, the system is still implementing a "bisection-like" approach and ultimately can "zoom in" on the sentence W of choice.

Figure 37:
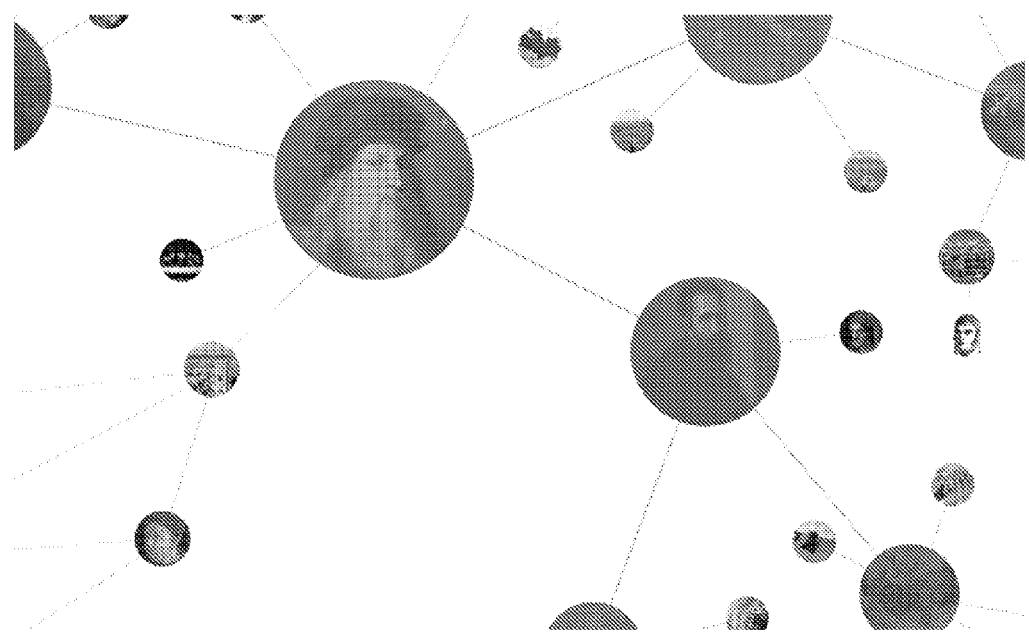
FIG. 37 shows an illustrative diagram of an example for representing the individual knowledge or awareness (W) as a graph, e.g., reflecting categorization and relationships

In general, for some approaches, e.g., particularly when attempting to identify W pertaining to individual knowledge or awareness, it is not always natural to embed W into a 1-dimensional space. Indeed, many conceptual categorization tools and databases use graphs, e.g., which inherently have dimensions of two or more. For example, some relationship database systems are two-dimensional systems to identify relationships between words to adequately and efficiently perform search (e.g., "bell" could be referring to Alexander Graham Bell, or a bell at elementary school). FIG. 37 shows an illustrative diagram of an example for representing the individual knowledge or awareness W as a graph, e.g., reflecting categorization and relationships. Important to consider is that W cannot be naturally represented as a point on the [0,1] line; rather, it must be represented in a higher-dimensional space that has a graphical nature. In such settings, there is not a closed form expression for the sequential experimental design to re-query experiments. For example, a problem arises in that how does one develop a mapping that "zooms in" on the desired latent variable of interest for dimensions greater than 1, for example, which are of particular relevance to the disclosed methods involving extracting state of knowledge information.

The disclosed systems and methods can provide a solution framework for sequential querying to "hone in" on a point of uncertainty by sequentially querying a system that provides responses that we acquire noisily. For example, what is of particular interested is when W is not on the [0,1] line (for which there is a closed-form optimal solution). In these more general cases, computational algorithms can be implemented, e.g., yet a simple formula describing the solution in general does not in general exist. In order to maximize mutual information, it is important that the next brain response $X_i$ be statistically independent of the neural signals acquired so far ($Y_1 \ldots Y_{i-1}$). For example, there are no known existing extensions to systematically provide experimental design paradigms guaranteeing this in situations where W is not in one dimension.

One exemplary application demonstrative of this framework is as follows. The uncertain knowledge is abstracted as a point W that lies in two dimensions, pertaining to a location of interest (e.g., downtown France and the Eiffel tower). A sequence of sub-images of the globe are randomly shown. On experiment i, if the visual stimulus contains the Eiffel tower, then an "ah-ha" moment arises as a brain state, modeled as $X_i=1$; otherwise, on experiment i, $X_i=0$. For example, an "ah-ha" moment results in a P300 event-related potential being triggered as a "target" in the neural activity $Y_i$; otherwise a "distractor" will occur in the neural activity. The statistics of $Y_i$ pertaining to when $X_i=0$ are different than when $X_i=1$, particularly within the time domain of 300 ms, as demonstrated by the P300 event-related potential. The exemplary experimental design paradigm of the disclosed technology takes the output neural activity $Y_1, \ldots, Y_{i-1}$ and develops a probability distribution or belief on which points on the map are targets, and which are distractors. The exemplary framework of the disclosed technology identifies the subsequent images to display, some of which are zoomed in to query more, and others that are zoomed out because they are likely not targets. It does this mapping optimally, and more so it can be done efficiently. An example of this idea, pertaining to sub-images and a point on a picture in two dimensions is shown in FIG. 38.

Figure 38:
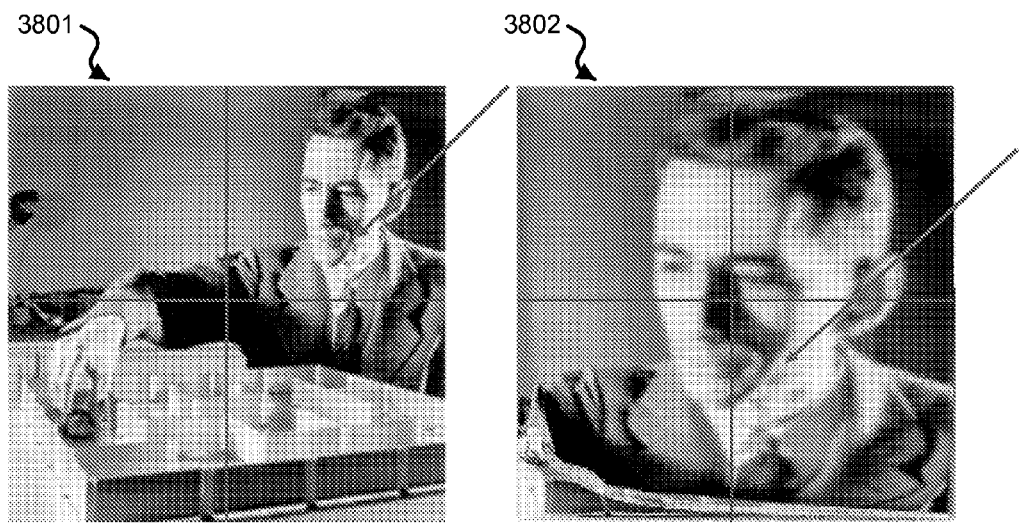
FIG. 38 shows exemplary images depicting an exemplary situation where the internal knowledge W is a point in two dimensions, e.g., reflecting a point in a picture.

FIG. 38 shows two exemplary images 3801 and 3802 as an example situation where the internal knowledge W is a point in two dimensions, e.g., reflecting a point in a picture (indicated on the images 3801 and 3802 where the blue arrow points). In the image 3801, a four sub-images are displayed, with boundaries given by the red vertical and horizontal lines. A sequence of these sub-images is displayed. When a sub-image is displayed containing the point of interest, it triggers an "ah-ha" internal brain state ($X_i=1$), they trigger an event-related potential in the EEG; otherwise $X_i=0$. In the image 3802, the exemplary system integrates the neural signals acquired from the previous sequence of images and re-presents a sequence of sub-images so that on the subsequent experiment, sub-images with a higher likelihood of containing individual knowledge (W) are more zoomed in on, and others are zoomed out on. This is demonstrated in image 3802 of FIG. 38 where the head is zoomed in upon and other parts of the original image are zoomed out upon. This "zooming in" is information-theoretically optimal; it maximizes mutual information I(W; $Y_1, \ldots Y_n$) and is guaranteed to probabilistically "zoom in" on individual knowledge (W) as efficiently as possible.

The exemplary techniques of the disclosed technology can be implemented to optimally perform this sequential experimental design, and having low complexity. For example, the challenge of zooming in on knowledge as efficiently as possible can be solved with the disclosed techniques of optimal transport. One core equation about mapping the current belief "p" to a subsequent belief of interest "q", is to find a map "S" for which if the individual knowledge W had distribution p, and Z=S(W), then Z would be drawn according to q.

$$p(u) = \underbrace{q(S(u))|\det J_S(u)|}_{\text{Jacobian Equation}}. \tag{3}$$

Equation (3) shows a Jacobian equation of how distributions (e.g., statistically descriptions or likelihoods) are shaped by the map S. In general, finding a solution to such an equation is non-convex and challenging (e.g., NP hard).

As an example, this relates to the "zooming in" picture by associating a pixel color to every possible point on the image 3801 of FIG. 38. If point u (e.g., specified in two dimensions) had a specific pixel color c on the image 3801, then point S(u) has that same specific pixel color c on the image 3802. This has the effect of "zooming in" on certain parts of the image, and zooming out on others. It is demonstrated here that by specifying a specific distribution p and q, mutual information can be maximized (e.g., zooming in on the point of interest in the image occurring as efficiently as possible) by applying this procedure and finding a solution S(u) to the above Jacobian equation. Here, p represents a uniform distribution over the possible W values, and q represents the posterior distribution after experiment i, $\pi_i$.

Also, for example, under appropriate assumptions about the noisy channel model p(y|x), finding a solution to the above Jacobian equation (and thus a solution the problem of experimental design to maximize mutual information) is computationally efficient. For example, if the neural likelihood p(y|x) is log-concave in x, then finding optimal map is "easy" (i.e., a convex optimization problem).

The assumption of log-concavity is applicable, for example, for all channel models where x is finite (e.g., of most interest to the aforementioned applications in this patent document). Moreover, many continuous input statistical models of p(y|x), such as Gaussian, Poisson, logistic, and all exponential families, also exhibit this exemplary property.

An exemplary technique pertaining to the computationally efficient convex optimization problem is as follows:

$$(P4)F^* = \underset{F \in \mathbb{R}^{d \times K}: FJ_A(X_1)>0, \ldots, FJ_A(X_N)>0}{\operatorname{argmax}} V_4(F),$$

-continued $$V_4(F) \triangleq \frac{1}{N} \sum_{i=1}^{N} \tilde{T}(F, X_i)$$

$$\tilde{T}(F, x) \triangleq \log f_{Y|X}(y|FA(x)) + \log f_X(FA(x)) + \log \det(FJ_A(x)) - \log f_X(x).$$

where $X_1, X_2, \ldots, X_N$ are drawn i.i.d. from $P_X$.

For example, using the described techniques of optimal transport, the exemplary problem P4 can yield a map S that satisfies the Jacobian equation, e.g., by implementing a computer implemented method of the disclosed technology (e.g., programmed in MATLAB script, e.g., using an exemplary CVX convex optimization software add-on). The diagram 3802 shows an example result of an exemplary implementation of this computer implemented method, e.g., showing a simulation of "zooming in" on intent pertaining to identifying one point of interest through a noisy channel.

For example, the disclosed framework, as described in this section, is applicable to an arbitrary problem in Bayesian inference. When certain assumptions (e.g., log-concavity—applicable to most statistical models) apply, the described techniques can be implemented to "zoom in" on features of interest in a computationally efficient manner. The implications for the described sequential experimental design and brain-machine interfaces are quite broad, as evidenced by these examples.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A system for providing a cognitive or sensory assessment, comprising:
   a sensor device interfaced to a subject to detect physiological signals exhibited by the subject before, during, and after a presentation of a sequence of stimuli to the subject, the sequence of stimuli based on a cognitive-sensory profile category from among one or more of a cognitive performance profile, a sensory performance profile, or a cognitive and sensory performance profile;

a data processing system in communication with the sensor device and structured to include one or more memory units and one or more processors configured to process the physiological signals to generate an information set including one or more quantitative values associated with the cognitive-sensory profile category, wherein the data processing system includes:

a local computer located proximate and in communication with the sensor device to receive the detected physiological signals from the sensor device, the local computer configured to conduct initial processing of the detected physiological signals to produce initial physiological signal data, and a remote computer in communication with the local computer via a communication network or link to receive the initial physiological signal data from the local computer and to process the initial physiological signal data to generate the information set including the one or more quantitative values associated with the cognitive-sensory profile category, wherein the initial physiological signal data includes a time interval associated with the detected physiological signals based on presented stimuli and the cognitive-sensory profile category, and wherein the remote computer is configured to:
group the initial physiological signal data corresponding to the time interval into one or more grouped data sets, and
provide a statistical measure of a relationship across or within the grouped data sets to generate the one or more quantitative values;

a stimulus delivery device at a location of the subject and configured to produce the sequence of stimuli that is presented to the subject, wherein the stimuli includes at least one of a visual, auditory, olfactory, tactile, or gustatory stimulating medium; and a stimulus presentation computer in communication with the remote computer and the stimulus delivery device, the stimulus presentation computer configured to modify the sequence of stimuli based at least in part on the information set during presentation of the sequence of stimuli to the subject and produce a modified sequence of stimuli that is individualized with respect to the subject, and to cause the stimulus delivery device to present the modified sequence of stimuli to the subject, wherein the information set is generated by the data processing system without requiring a behavioral response by the subject to the sequence of stimuli.

2. The system as in claim 1, wherein the stimulus delivery device includes a display screen to generate a sequence of images.

3. The system as in claim 1, wherein the stimulus delivery device includes a speaker to generate a sequence of sounds.

4. The system as in claim 1, wherein the stimulus delivery device includes an actuator to generate a sequence of at least one of olfactory, tactile, or gustatory stimuli.

5. The system as in claim 1, wherein the data processing system is configured to produce a machine procedure based on the generated information set, and wherein the machine procedure produced by the data processing system causes the stimulus delivery device to modify the sequence of stimuli for a next presentation to the subject.

6. The system as in claim 1, wherein one or both of the stimulus delivery device and the stimulus presentation computer includes a desktop computer, a laptop computer, or a mobile communications device including a smartphone or tablet.

7. The system as in claim 1, wherein the local computer includes a mobile communications device including a smartphone or tablet.

8. The system as in claim 1, wherein the data processing system is configured to produce a machine procedure based on the generated information set, and wherein the machine procedure actuates another device or system to perform a function derived from information contained within the generated information set.

9. The system as in claim 1, wherein the one or more quantitative values includes a quantitative score depicting a level of one or both of cognitive and sensory performance based on at least one of the subject's attention, memory, learning ability, confabulation characteristics, pattern integration ability, semantic integration ability, target detection ability, emotional valence, preference, or awareness, and wherein the quantitative score depicts the level at a particular time.

10. The system as in claim 1, wherein the sensor device includes a flexible substrate, sensor electrodes on the flexible substrate, and a transmitter unit in electrical communication with the electrodes and on the flexible substrate, wherein the sensor device is configured as one or more wearable patches worn on the subject's scalp to record electroencephalogram (EEG) signals and transmit the recorded EEG signals to at least one of the data processing system or a remote computer system.

11. The system as in claim 1, wherein the sensor device includes electrodes attachable to the subject to receive electrical signals from the subject.

12. The system as in claim 1, wherein the local computer is configured to produce the initial physiological signal data as individual data specific to the subject, and the remote computer is configured to process the initial physiological signal data to produce the information set that is individualized to the subject.

13. The system as in claim 1, wherein the remote computer is configured to access physiological signal data of other subjects in one or more groups of subjects and use the physiological signal data of other subjects in processing of the initial physiological signal data to produce the information set that is individualized to the subject.

14. The system as in claim 13, wherein the data processing system includes a brain-machine interface module configured to convert the information set that is individualized to the subject into adaptive change or adjustment that is used by the stimulus presentation computer to modify the sequence of stimuli during the presentation to the subject in producing the modified sequence of stimuli that is individualized with respect to the subject.

15. The system as in claim 1, wherein the data processing system includes a brain-machine interface module configured to convert the information set that is individualized to the subject into adaptive change or adjustment that is used by the stimulus presentation computer to modify the sequence of stimuli during the presentation to the subject in producing the modified sequence of stimuli that is individualized with respect to the subject.

16. A system for providing a cognitive or sensory assessment, comprising:
a sensor device interfaced to a subject to detect physiological signals exhibited by the subject before, during, and after a presentation of a sequence of stimuli to the subject, the sequence of stimuli based on a cognitive-sensory profile category from among one or more of a cognitive performance profile, a sensory performance profile, or a cognitive and sensory performance profile;

a data processing system in communication with the sensor device and structured to include one or more memory units and one or more processors configured to process the physiological signals as physiological data to generate an information set including one or more quantitative values associated with the cognitive-sensory profile category;

a stimulus delivery device at a location of the subject and configured to produce the sequence of stimuli that is presented to the subject, wherein the stimuli includes at least one of a visual, auditory, olfactory, tactile, or gustatory stimulating medium; and a stimulus presentation computer in communication with the stimulus delivery device and the data processing system to receive data associated with or derived from the information set and to modify the sequence of stimuli based at least in part on the received data to produce a modified sequence of stimuli that is individualized with respect to the subject, the stimulus presentation computer operable to cause the stimulus delivery device to present the modified sequence of stimuli during the presentation of the sequence of stimuli to the subject, wherein, to process the physiological data to generate the information set, the data processing system is configured to:
identify a time interval for each of the detected physiological signals based on the presented stimuli and the cognitive-sensory profile category,
group the physiological data corresponding to the time interval into one or more grouped data sets, and
provide a statistical measure of a relationship across or within the grouped data sets to generate the one or more quantitative values for the cognitive-sensory profile category, wherein the information set is generated by the data processing system without requiring a behavioral response by the subject to the sequence of stimuli.

17. The system as in claim 16, wherein the data processing system, the stimulus delivery device, and the stimulus presentation computer are configured in a mobile communications device including a smartphone or tablet.

* * * * *